US011908589B2

(12) United States Patent
Takahata et al.

(10) Patent No.: US 11,908,589 B2
(45) Date of Patent: Feb. 20, 2024

(54) METHOD OF SUPPORTING INTERPRETATION OF GENETIC INFORMATION BY MEDICAL SPECIALIST, INFORMATION MANAGEMENT SYSTEM, AND INTEGRATED DATA MANAGEMENT DEVICE

(71) Applicant: SYSMEX CORPORATION, Kobe (JP)

(72) Inventors: Takayuki Takahata, Kobe (JP); Tatsuru Wakimoto, Kobe (JP); Yusaku Matsuo, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 249 days.

(21) Appl. No.: 16/810,973

(22) Filed: Mar. 6, 2020

(65) Prior Publication Data

US 2020/0286634 A1 Sep. 10, 2020

(30) Foreign Application Priority Data

Mar. 7, 2019 (JP) ................................ 2019-041671

(51) Int. Cl.
*G16H 10/40* (2018.01)
*G16H 10/60* (2018.01)
(Continued)

(52) U.S. Cl.
CPC ............. *G16H 80/00* (2018.01); *A61B 5/742* (2013.01); *G06F 9/542* (2013.01);
(Continued)

(58) Field of Classification Search
CPC ........ G16H 80/00; G16H 10/40; A61B 5/742; G06F 9/542; G06Q 10/1095
(Continued)

(56) References Cited

U.S. PATENT DOCUMENTS

| | | | | |
|---|---|---|---|---|
| 7,810,045 | B2 * | 10/2010 | Weber | G16H 10/60 715/792 |
| 8,972,845 | B2 * | 3/2015 | Wu | G06F 16/93 707/738 |

(Continued)

FOREIGN PATENT DOCUMENTS

| | | | |
|---|---|---|---|
| CN | 1381119 | A | 11/2002 |
| CN | 101414325 | A | 4/2009 |

(Continued)

OTHER PUBLICATIONS

Shumpei Ishikawa, "The State of the Judgement of the Gene Panel Used in the Country", Working Group on Requirements for Designation of Cancer Treatment Center Hospital, Sub-working Group on Requirements for Designation as a Cancer Genome Center Hospital, Oct. 4, 2017, Ministry of Health, Labour and Welfare, Japan, Internet search on Aug. 7, 2020, retrieved from <URL: https://www.mhlw.go.jp/stf/shingi2/0000179778.html>; Cited in the JPOA issued on Sep. 23, 2020 in a counterpart Japanese patent application.

(Continued)

*Primary Examiner* — Tauqir Hussain
(74) *Attorney, Agent, or Firm* — METROLEX IP LAW GROUP, PLLC

(57) ABSTRACT

A method of supporting an expert meeting of medical specialists to interpret genetic information, may include: accepting a test request for genetic information on a patient; extracting test progress information that is stored in association with the accepted test request and indicates progress of a test for the test request, and schedule information on a schedule of the expert meeting to interpret the genetic information obtained in the test for the test request; and displaying the extracted test progress information and the
(Continued)

extracted schedule information on terminal devices of the medical specialists.

23 Claims, 39 Drawing Sheets

(51) Int. Cl.
*A61B 5/00* (2006.01)
*G06F 9/54* (2006.01)
*G06Q 10/1093* (2023.01)
*G16H 80/00* (2018.01)

(52) U.S. Cl.
CPC ......... *G06Q 10/1095* (2013.01); *G16H 10/40* (2018.01); *G16H 10/60* (2018.01)

(58) Field of Classification Search
USPC .......................................................... 709/204
See application file for complete search history.

(56) References Cited

U.S. PATENT DOCUMENTS 9,633,373 B2 * 4/2017 Jung ..................... H04W 12/08
9,870,451 B1 * 1/2018 Patel ....................... H04L 67/10
9,996,672 B2 * 6/2018 Lo .......................... G16H 10/60
10,642,958 B1 * 5/2020 Perlin ................. G06F 16/9535
10,665,348 B1 * 5/2020 Krayer ................... G16H 50/30
10,785,562 B1 * 9/2020 Weekly ................... G10L 15/22
10,796,795 B1 * 10/2020 Bullington ............. G16H 80/00
10,832,823 B1 * 11/2020 Lippoff ................... H04L 67/52
10,854,330 B1 * 12/2020 Bullington .......... G06F 16/2457
11,107,575 B1 * 8/2021 Bullington ......... G06Q 10/1095
2001/0039502 A1 * 11/2001 Case ...................... G16H 40/67 705/2
2003/0179223 A1 * 9/2003 Ying ..................... G06F 3/0488 715/702
2003/0191772 A1 10/2003 Schaumann et al.
2005/0055240 A1 3/2005 Walsh et al.
2005/0265533 A1 * 12/2005 White ..................... H04L 65/80 709/204
2005/0276477 A1 * 12/2005 Lin ......................... G06T 11/60 382/173
2006/0036536 A1 * 2/2006 Williams ............. G06Q 20/102 705/40
2006/0271400 A1 * 11/2006 Clements ............... G16H 10/60 600/301
2009/0138285 A1 * 5/2009 Denberg ................ G16H 10/60 707/E17.014
2009/0156906 A1 * 6/2009 Liebman ................ G16H 50/50 600/300
2009/0259489 A1 10/2009 Kimura et al.
2009/0313044 A1 * 12/2009 Haque .................... G16H 10/60 705/2
2010/0250270 A1 * 9/2010 Naji ....................... G16H 70/20 709/201
2011/0099006 A1 * 4/2011 Sundararaman .... H04L 12/1831 704/235
2012/0016685 A1 * 1/2012 Ryan ...................... G16H 10/20 715/764
2013/0103423 A1 4/2013 Kim
2014/0006055 A1 * 1/2014 Seraly .................... G06Q 10/10 705/3
2014/0081667 A1 * 3/2014 Joao ....................... G16H 40/63 705/3
2014/0297320 A1 * 10/2014 Jiwani .................... G16H 10/60 705/3
2014/0298206 A1 10/2014 Kurosawa
2014/0365396 A1 12/2014 Kumar et al.
2015/0019242 A1 * 1/2015 Murata .................. G16H 20/10 705/2
2015/0310183 A1 * 10/2015 Madhavan ............. G16H 40/67 705/2
2015/0331997 A1 * 11/2015 Joao ....................... G16H 10/60 705/3
2016/0203277 A1 * 7/2016 Okabe .................... G16H 40/20 705/2
2016/0203286 A1 * 7/2016 Okabe .................... G16H 30/20 705/2
2016/0224195 A1 * 8/2016 Okabe ................... G06F 3/0482
2017/0068789 A1 3/2017 Dalton et al.
2017/0076046 A1 * 3/2017 Barnes .................. G06F 16/951
2017/0116384 A1 * 4/2017 Ghani .................... G16H 70/20
2017/0228511 A1 * 8/2017 Kobneck ................ G16H 10/20
2018/0060482 A1 3/2018 Nadauld et al.
2018/0358122 A1 * 12/2018 Raghotham Venkat ..................... G16H 40/20
2019/0392922 A1 * 12/2019 Bader .................... G16H 20/40
2020/0019946 A1 * 1/2020 Walker ................... G06Q 20/14
2020/0066386 A1 * 2/2020 Katz ...................... G16H 20/10
2020/0075142 A1 * 3/2020 Kano ..................... G16H 20/00
2020/0087709 A1 * 3/2020 Bracht ................. C12Q 1/6818
2020/0090132 A1 * 3/2020 Bender ................. G06F 16/337
2020/0104961 A1 * 4/2020 Romeo ................ G06Q 10/087
2020/0160984 A1 * 5/2020 Vegas Santiago ..... G16H 10/60
2020/0160985 A1 * 5/2020 Kusuma ................. G16H 30/40
2020/0160986 A1 * 5/2020 Vegas Santiago ....... G06N 5/01
2020/0227157 A1 * 7/2020 Vincent ................. G06F 3/0485
2020/0257697 A1 * 8/2020 Bhabesh ............. G06F 16/1824
2020/0310611 A1 * 10/2020 Vincent .................. G09G 5/393
2020/0310612 A1 * 10/2020 Vincent ................... G06F 16/54
2020/0342981 A1 * 10/2020 Kaufman ........... G06Q 10/1095
2021/0225499 A1 * 7/2021 Takayama .............. G16H 40/20
2021/0272682 A1 * 9/2021 Hebrard ................. G16H 30/00
2021/0319860 A1 * 10/2021 Ahmed .................. G16H 80/00
2021/0319902 A1 * 10/2021 Ahmed .................. G16H 80/00
2022/0051787 A1 * 2/2022 Sugai ..................... A61B 5/746

FOREIGN PATENT DOCUMENTS

CN 102299946 A 12/2011
CN 103337047 A 10/2013
CN 103813035 A 5/2014
CN 204331789 U 5/2015
CN 106047998 A 10/2016
CN 106454203 A 2/2017
CN 106650256 A 5/2017
CN 107615397 A 1/2018
CN 108062982 A 5/2018
CN 108269619 A 7/2018
CN 108538402 A 9/2018
JP 2004-344314 A 12/2004
JP 2005-190314 A 7/2005
JP 2007-65827 A 3/2007
JP 2007065827 A * 3/2007
JP 2009-193157 A 8/2009
JP 2009193157 A * 8/2009
JP 2012-84008 A 4/2012
JP 2017-182237 A 10/2017
JP 2018-533123 A 11/2018
WO 2005/059802 A2 6/2005
WO 2014/074001 A2 5/2014
WO 2014/074001 A3 5/2014
WO 2017/115140 A1 7/2017
WO 2017115140 A1 7/2017

OTHER PUBLICATIONS

The Office Action (JPOA) dated Sep. 23, 2020 in a counterpart Japanese patent application.
The extended European search report (EESR) dated Jun. 22, 2020 in a counterpart European patent application.
The Communication pursuant to Article 94 (3) EPC dated Aug. 18, 2023 in a related European patent application.
EPOA dated Aug. 18, 2023 in a counterpart patent application No. EP 20161441.
The Communication pursuant to Article 94 (3) EPC dated Sep. 25, 2023 in a related European patent application.
Japanese Office Action dated Aug. 2, 2022 in a related Japanese patent application No. 2021-079919.

(56) References Cited

OTHER PUBLICATIONS

Japanese Office Action dated Aug. 2, 2022 in a related Japanese patent application No. 2021-079920.
Japanese Office Action dated Aug. 2, 2022 in a related Japanese patent application No. 2021-079921.
A Chinese Office Action dated Sep. 26, 2023 in a related Chinese patent application.
Chinese Office Action dated Oct. 21, 2023 in a counterpart Chinese patent application.
Chinese Office Action dated Oct. 21, 2023 in a related Chinese patent application.

* cited by examiner

38

| USE ID | LOGIN PASSWORD |
|---|---|
| ... | ... |
| U05 | passxyz |
| ... | ... |

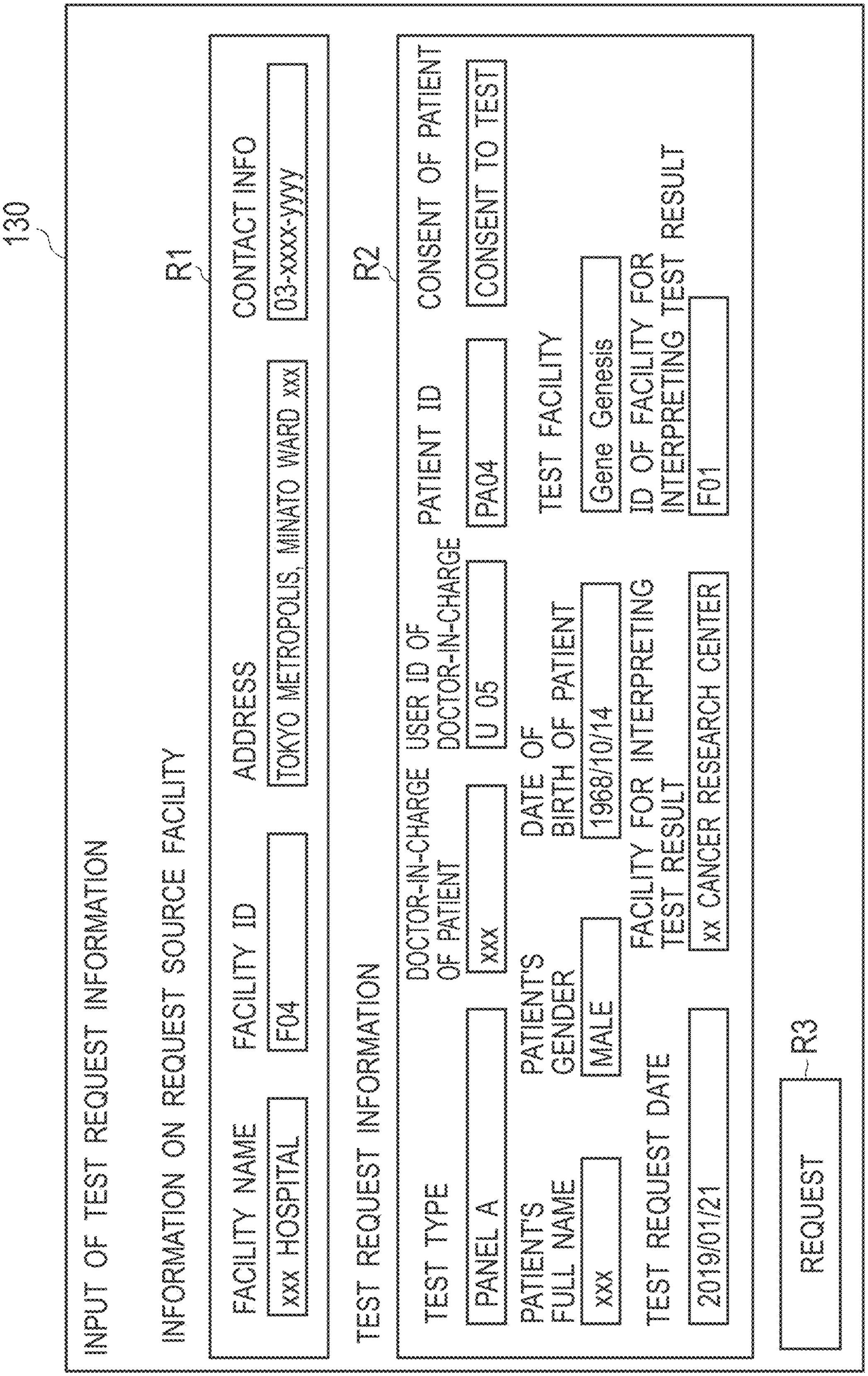

FIG. 7

INPUT OF TEST REQUEST INFORMATION — 130

INFORMATION ON REQUEST SOURCE FACILITY — R1

| FACILITY NAME | FACILITY ID | ADDRESS | CONTACT INFO |
|---|---|---|---|
| xxx HOSPITAL | F04 | TOKYO METROPOLIS, MINATO WARD xxx | 03-xxxx-yyyy |

TEST REQUEST INFORMATION — R2

| TEST TYPE | DOCTOR-IN-CHARGE OF PATIENT | USER ID OF DOCTOR-IN-CHARGE | PATIENT ID | CONSENT OF PATIENT |
|---|---|---|---|---|
| PANEL A | xxx | U 05 | PA04 | CONSENT TO TEST |

| PATIENT'S FULL NAME | PATIENT'S GENDER | DATE OF BIRTH OF PATIENT | TEST FACILITY |
|---|---|---|---|
| xxx | MALE | 1968/10/14 | Gene Genesis |

| TEST REQUEST DATE | FACILITY FOR INTERPRETING TEST RESULT | ID OF FACILITY FOR INTERPRETING TEST RESULT |
|---|---|---|
| 2019/01/21 | xx CANCER RESEARCH CENTER | F01 |

REQUEST — R3

| FACILITY ID | FACILITY NAME |
|---|---|
| F01 | xx CANCER RESEARCH CENTER |
| ... | ... |
| F04 | xxx HOSPITAL |
| F05 | yyy MEDICAL CENTER |
| ... | ... |

| GENE PANEL ID | GENE PANEL NAME |
|---|---|
| ... | ... |
| P015 | PANEL A |
| P016 | PANEL B |
| ... | ... |

| USER ID | FULL NAME OF MEDICAL SPECIALIST | LOGIN INFORMATION | SPECIALTY | CONTACT INFORMATION | ROLE ID |
|---|---|---|---|---|---|
| ... | ... | ... | ... | ... | ... |
| U05 | xxx | ... | ... | ... | R01 |
| U06 | yyyy | ... | ... | ... | ... |
| ... | ... | ... | ... | ... | ... |

24

| TEST FACILITY ID | TEST FACILITY NAME |
|---|---|
| ... | ... |
| R06 | Gene Genesis |
| R07 | yy TEST CENTER |
| ... | ... |

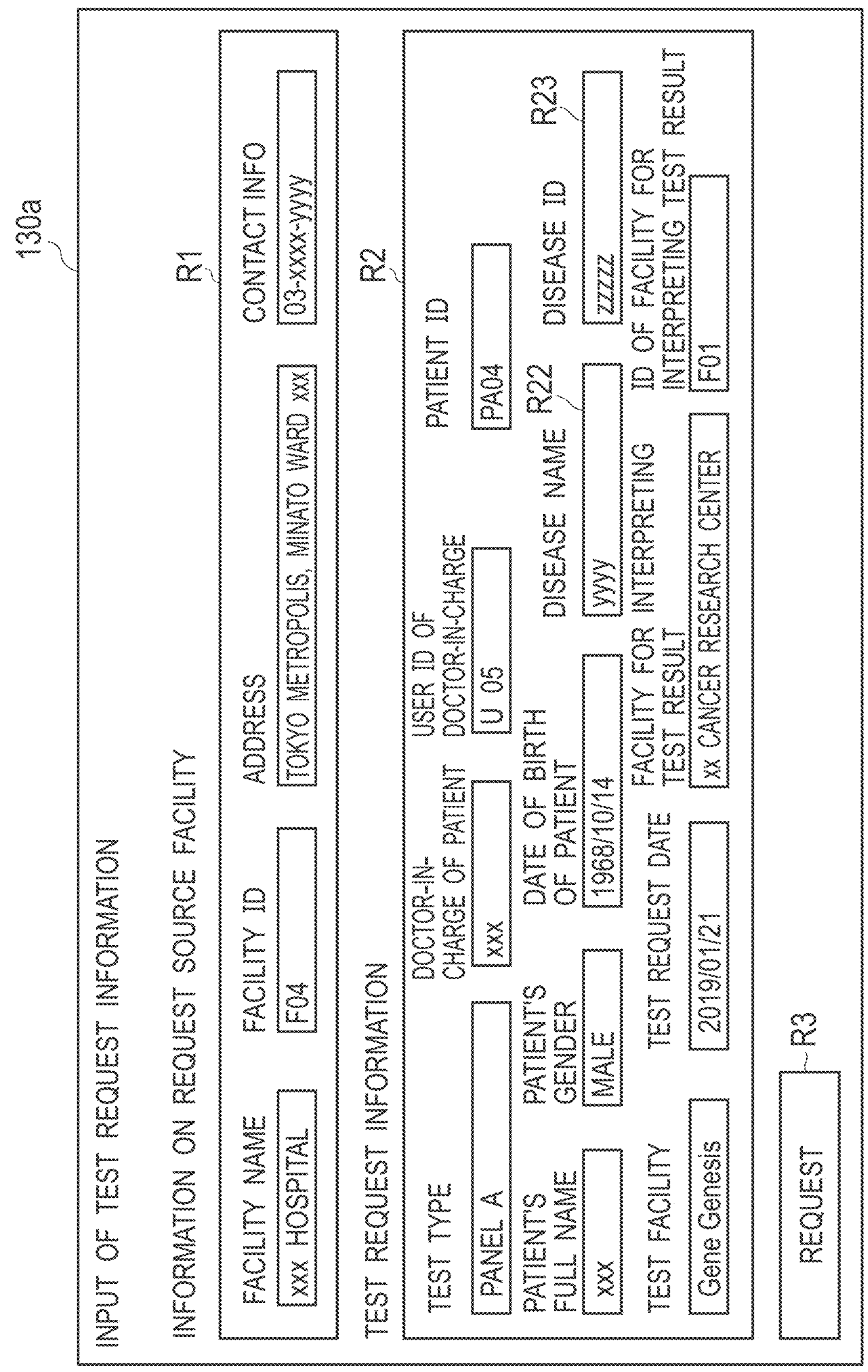

FIG. 13

INPUT OF TEST REQUEST INFORMATION

INFORMATION ON REQUEST SOURCE FACILITY — R1

| FACILITY NAME | FACILITY ID | ADDRESS | CONTACT INFO |
|---|---|---|---|
| xxx HOSPITAL | F04 | TOKYO METROPOLIS, MINATO WARD xxx | 03-xxxx-yyyy |

TEST REQUEST INFORMATION — R2

| TEST TYPE | DOCTOR-IN-CHARGE OF PATIENT | USER ID OF DOCTOR-IN-CHARGE | PATIENT ID |
|---|---|---|---|
| PANEL A | xxx | U_05 | PA04 — R22 |

| PATIENT'S FULL NAME | PATIENT'S GENDER | DATE OF BIRTH OF PATIENT | DISEASE NAME | DISEASE ID |
|---|---|---|---|---|
| xxx | MALE | 1968/10/14 | yyyy | zzzzz — R23 |

| TEST FACILITY | TEST REQUEST DATE | FACILITY FOR INTERPRETING TEST RESULT | ID OF FACILITY FOR INTERPRETING TEST RESULT |
|---|---|---|---|
| Gene Genesis | 2019/01/21 | xx CANCER RESEARCH CENTER | F01 |

[REQUEST] — R3

| PATIENT ID | SAMPLE ID | TEST REQUEST ID | GENE PANEL ID | PATIENT'S FULL NAME | PATIENT'S GENDER | DATE OF BIRTH OF PATIENT | CONSENT OF PATIENT | TEST REQUEST DATE | USER ID OF MEDICAL SPECIALIST | FULL NAME OF MEDICAL SPECIALIST | GROUP ID | PROGRESS OF TEST | CLINICAL INFORMATION | TEST RESULT | FACILITY FOR EXPERT MEETING | DATE AND TIME OF EXPERT MEETING |
|---|---|---|---|---|---|---|---|---|---|---|---|---|---|---|---|---|
| PA01 | SA01 | T01 | ... | TANAKA ICHIRO | MALE | 1977/ 04/14 | ... | 2018/ 10/10 | U01 | ... | ... | ... | ... | ... | ... | ... |
| PA02 | SA02 | T02 | ... | xxxxx | MALE | 1960/ 01/20 | ... | 2018/ 10/11 | ... | ... | ... | ... | ... | ... | ... | ... |
| PA03 | SA03 | T03 | ... | yyyyy | FEMALE | 1963/ 01/04 | ... | 2018/ 12/10 | ... | ... | ... | ... | ... | ... | ... | ... |
| PA04 | SA04 | T04 | P015 | xxx | MALE | 1968/ 10/14 | ... | 2019/ 01/21 | U05 | XXX | G01 | PRETREATMENT INCOMPLETE | ... | ... | XX CANCER RESEARCH CENTER | ... |
| ... | ... | ... | ... | ... | ... | ... | ... | ... | ... | ... | ... | ... | ... | ... | ... | ... |

| GROUP ID | FACILITY ID | USER ID OF USER CONSTITUTING GROUP |
|---|---|---|
| G01 | F01 | U01, U02, U03, U04, U05, ··· |
| G02 | F01 | U01, U04, U06, U10, U11, ··· |
| G03 | F02 | U03, U08, U12, U13, U15, ··· |
| G04 | F02 | U18, U19, U20, U21, U22, ··· |
| G05 | F03 | U21, U22, U23, U24, U25, ··· |
| ··· | ··· | ··· |

| GROUP ID | FACILITY ID | DATE AND TIME OF EXPERT MEETING | ALLOWABLE PATIENT COUNT |
|---|---|---|---|
| G01 | F01 | 2018/11/30, 1:00pm - 5:00pm | 4 |
| ··· | ··· | ··· | ··· |
| G02 | F01 | 2018/11/28, 1:00pm - 5:00pm | 4 |
| ··· | ··· | ··· | ··· |
| G03 | F02 | 2018/12/04, 3:00pm - 6:00pm | 3 |
| ··· | ··· | ··· | ··· |

| INTEGRATED ID | PATIENT ID | TEST REQUEST ID |
|---|---|---|
| oXy796K | PA01 | T01 |
| 7FKZqbP | PA02 | T02 |
| ··· | ··· | ··· |

| INTEGRATED ID | PATIENT ID | FACILITY ID | TEST REQUEST ID |
|---|---|---|---|
| ... | ... | ... | ... |
| MyiYAm2 | PA04 | F01 | T04 |
| ... | ... | ... | ... |

| DATA ID | DATA TYPE ID | GENDER | AGE | DISEASE ID | DISEASE STATUS | TREATMENT HISTORY | ... |
|---|---|---|---|---|---|---|---|
| P01 | PA | MALE | 52 YRS | LUNG | ... | ... | ... |
| P02 | PA | FEMALE | 49 YRS | LUNG | ... | ... | ... |
| P03 | PA | FEMALE | 81 YRS | COLON | ... | ... | ... |
| ... | ... | ... | ... | ... | ... | ... | ... |

| DISEASE NAME | DISEASE ID |
|---|---|
| LUNG CANCER | LUNG |
| LARGE INTESTINE CANCER | COLON |
| ... | ... |

| DATA ID | DATA TYPE ID | SAMPLE COLLECTION DATE | COLLECTION SITE | LINK TO PATHOLOGICAL IMAGE | PATHOLOGIST OPINION | ... |
|---|---|---|---|---|---|---|
| IM01 | IM | YYYY/MM/DD | ... | Image 01 | ... | ... |
| IM02 | IM | YYYY/MM/DD | ... | Image 02 | ... | ... |
| IM03 | IM | YYYY/MM/DD | ... | Image 03 | ... | ... |
| ... | ... | ... | ... | ... | ... | ... |

| DATA ID | DATA TYPE ID | LINK TO REPORT | DETECTED MUTATION | THERAPEUTIC AGENT INFORMATION | GENE PANEL ID | DISEASE ID | SAMPLE QUALITY | DNA AMOUNT | ... |
|---|---|---|---|---|---|---|---|---|---|
| N01 | TEST | Report 01 | EGFR T790M | MEDICAMENT A | PType01 | LUNG | ... | ... | ... |
| | | | BRAF V600E | MEDICAMENT B | | | | | |
| N02 | TEST | ... | ... | ... | PType01 | LUNG | ... | ... | ... |
| N03 | TEST | ... | ... | ... | PType01 | COLON | ... | ... | ... |
| ... | ... | ... | ... | ... | ... | ... | ... | ... | ... |

| DATA ID | DATA TYPE ID | TYPE | LINK TO INFORMATION | LINK TO DATA | TEXT INFORMATION | ... |
|---|---|---|---|---|---|---|
| A01 | ANN | MUTATION | https:// xxx. yyy. com | Data A01 | ... | ... |
| A02 | ANN | THERAPEUTIC AGENT | ... | ... | ... | ... |
| A03 | ANN | THERAPEUTIC AGENT (CLINICAL TRIAL) | ... | ... | ... | ... |
| ... | ... | ... | ... | ... | ... | ... |

| ROLE ID | ROLE NAME |
|---|---|
| R01 | DOCTOR-IN-CHARGE |
| R02 | PATHOLOGIST |
| R03 | CANCER PHARMACOTHERAPY SPECIALIST |
| R04 | BIOINFORMATICS EXPERT |
| R05 | GENETIC COUNSELOR |
| R06 | MOLECULAR GENETICS RESEARCHER |
| R07 | GENETIC MEDICINE SPECIALIST |
| R08 | CLINICAL LABORATORY TECHNICIAN AT TEST FACILITY |
| R09 | EMPLOYEE AT TRANSPORTATION ESTABLISHMENT |
| ... | ... |

| ROLE ID | DATA TYPE ID OF DATA PERMITTED TO BE ACCESSED | ... |
|---|---|---|
| R01 | PA, IM, TEST, ANN | ... |
| R02 | PA, IM, TEST, ANN | ... |
| ... | ... | ... |
| R08 | TEST, ANN | ... |
| ... | ... | ... |

LIST OF TEST REQUESTS

| REQUEST DATE | TEST REQUEST ID | PREPARATION STATUS OF SAMPLE | TEST REQUEST SOURCE | TEST FACILITY |
|---|---|---|---|---|
| 2018/12/14 | PA10 | SAMPLE PREPARATION COMPLETED | xxx HOSPITAL | TEST FACILITY X |
| 2018/12/26 | PA05 | PREPARING SAMPLE | yyy HOSPITAL | TEST FACILITY Y |
| | ... | | | |

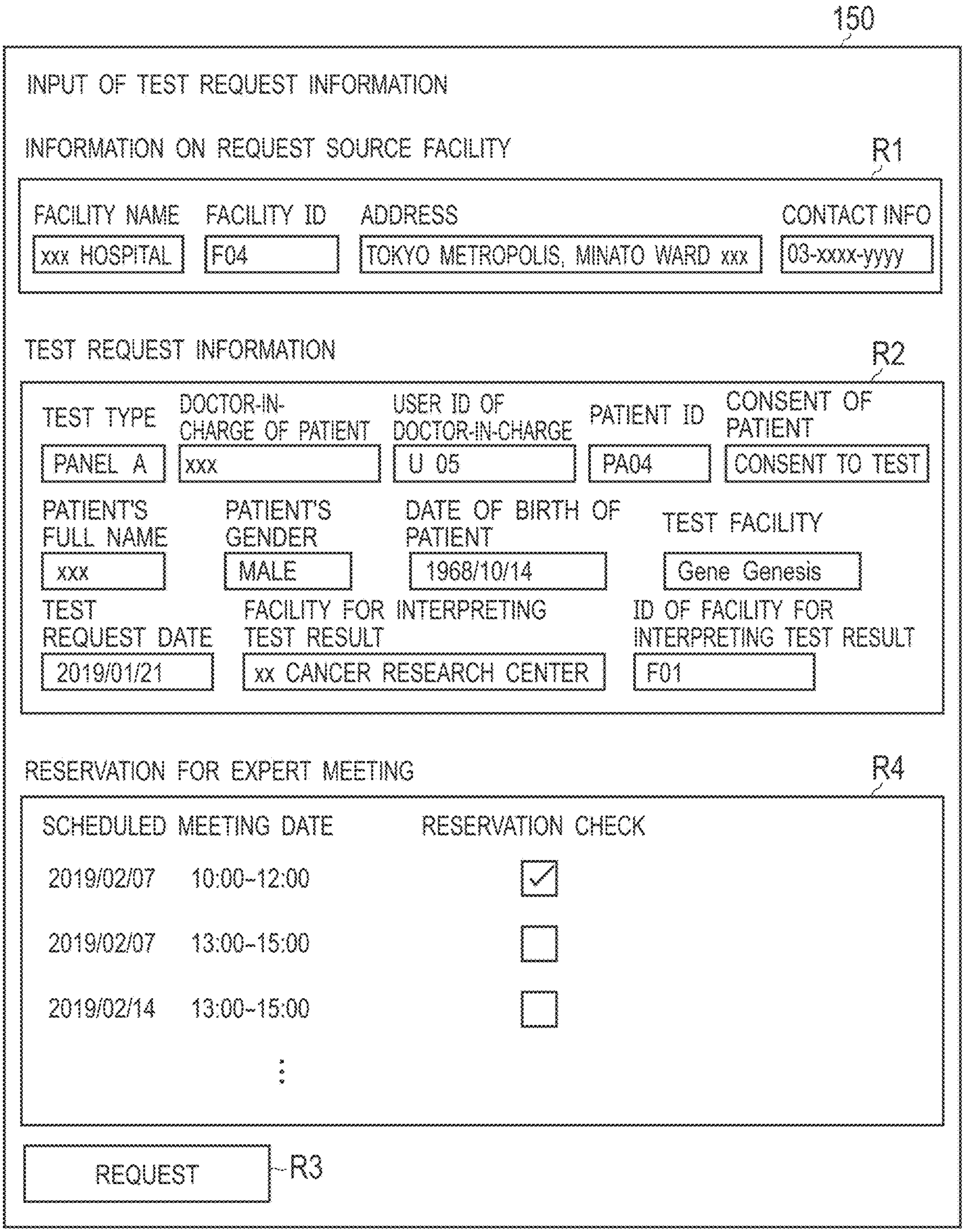

FIG. 29

```
INPUT OF TEST REQUEST INFORMATION

INFORMATION ON REQUEST SOURCE FACILITY                                    R1

  FACILITY NAME    FACILITY ID   ADDRESS                         CONTACT INFO
  [xxx HOSPITAL]   [F04]         [TOKYO METROPOLIS, MINATO WARD xxx]  [03-xxxx-yyyy]

TEST REQUEST INFORMATION                                                   R2

  TEST TYPE   DOCTOR-IN-        USER ID OF          PATIENT ID   CONSENT OF
              CHARGE OF PATIENT DOCTOR-IN-CHARGE                 PATIENT
  [PANEL A]   [xxx]             [U 05]              [PA04]       [CONSENT TO TEST]

  PATIENT'S       PATIENT'S      DATE OF BIRTH OF    TEST FACILITY
  FULL NAME       GENDER         PATIENT
  [xxx]           [MALE]         [1968/10/14]        [Gene Genesis]

  TEST            FACILITY FOR INTERPRETING          ID OF FACILITY FOR
  REQUEST DATE    TEST RESULT                        INTERPRETING TEST RESULT
  [2019/01/21]    [xx CANCER RESEARCH CENTER]        [F01]

RESERVATION FOR EXPERT MEETING                                             R4

  SCHEDULED MEETING DATE        RESERVATION CHECK

  2019/02/07   10:00~12:00              [✓]

  2019/02/07   13:00~15:00              [ ]

  2019/02/14   13:00~15:00              [ ]

                     ⋮

  [ REQUEST ]  —R3
```

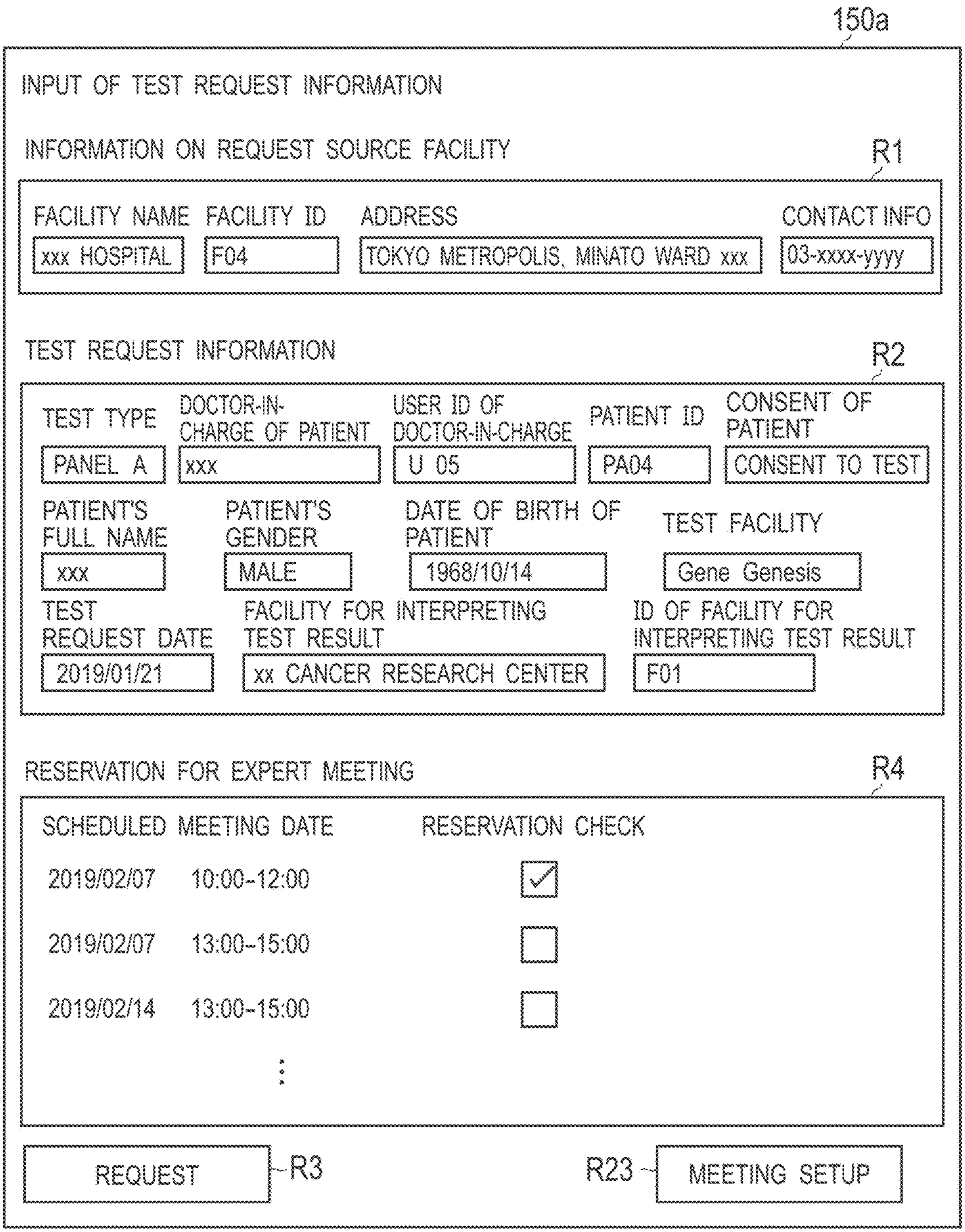

INPUT OF TEST REQUEST INFORMATION

INFORMATION ON REQUEST SOURCE FACILITY — R1

| FACILITY NAME | FACILITY ID | ADDRESS | CONTACT INFO |
|---|---|---|---|
| xxx HOSPITAL | F04 | TOKYO METROPOLIS, MINATO WARD xxx | 03-xxxx-yyyy |

TEST REQUEST INFORMATION — R2

| TEST TYPE | DOCTOR-IN-CHARGE OF PATIENT | USER ID OF DOCTOR-IN-CHARGE | PATIENT ID | CONSENT OF PATIENT |
|---|---|---|---|---|
| PANEL A | xxx | U 05 | PA04 | CONSENT TO TEST |

| PATIENT'S FULL NAME | PATIENT'S GENDER | DATE OF BIRTH OF PATIENT | TEST FACILITY |
|---|---|---|---|
| xxx | MALE | 1968/10/14 | Gene Genesis |

| TEST REQUEST DATE | FACILITY FOR INTERPRETING TEST RESULT | ID OF FACILITY FOR INTERPRETING TEST RESULT |
|---|---|---|
| 2019/01/21 | xx CANCER RESEARCH CENTER | F01 |

RESERVATION FOR EXPERT MEETING — R4

| SCHEDULED MEETING DATE | | RESERVATION CHECK |
|---|---|---|
| 2019/02/07 | 10:00–12:00 | ☑ |
| 2019/02/07 | 13:00–15:00 | ☐ |
| 2019/02/14 | 13:00–15:00 | ☐ |
| ⋮ | | |

REQUEST — R3         R23 — MEETING SETUP

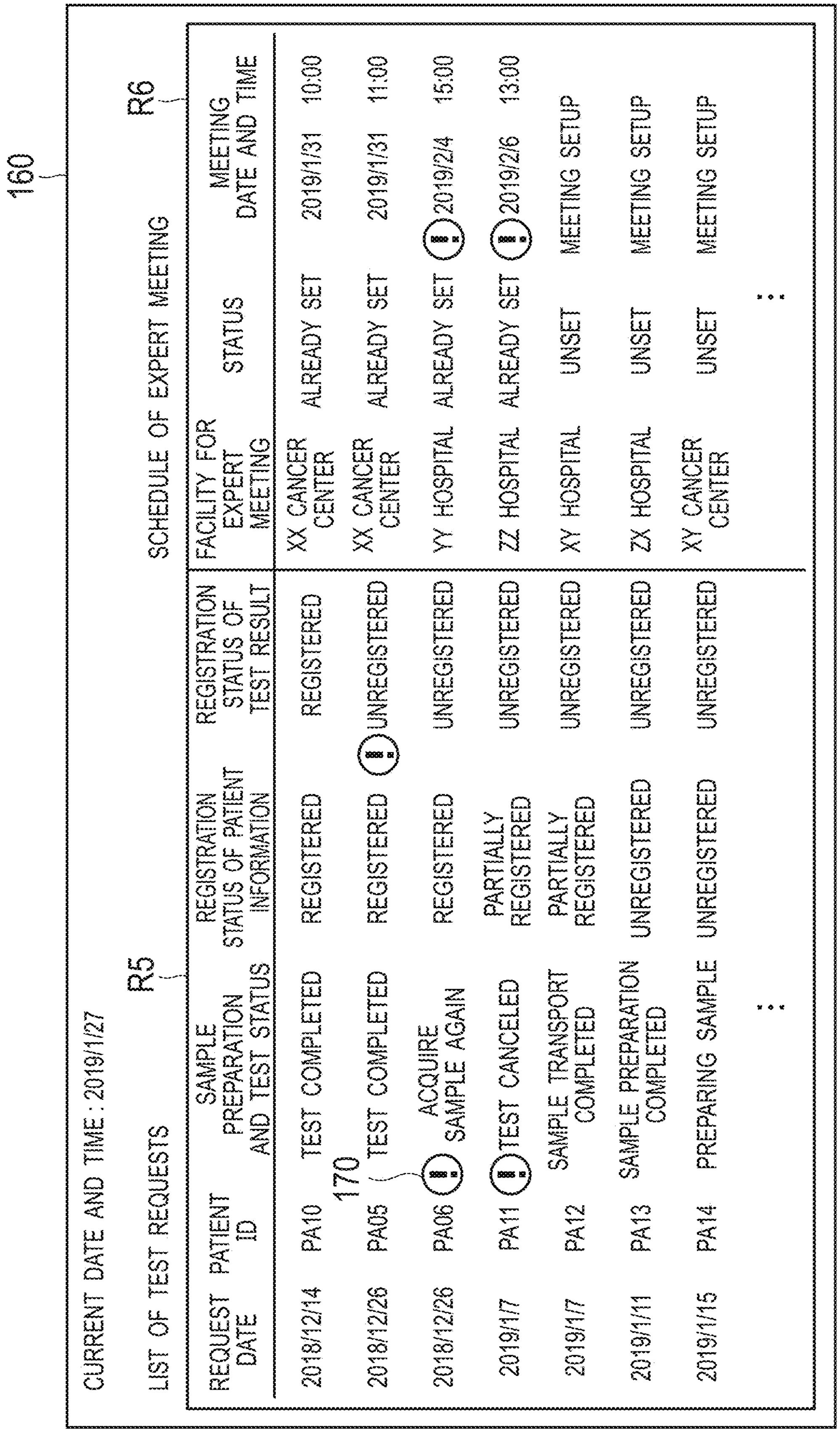

FIG. 33

CURRENT DATE AND TIME: 2019/1/27

LIST OF TEST REQUESTS    R5                                                                          R6

| REQUEST DATE | PATIENT ID | SAMPLE PREPARATION AND TEST STATUS | REGISTRATION STATUS OF PATIENT INFORMATION | REGISTRATION STATUS OF TEST RESULT | FACILITY FOR EXPERT MEETING | STATUS | MEETING DATE AND TIME |
|---|---|---|---|---|---|---|---|
| 2018/12/14 | PA10 | TEST COMPLETED | REGISTERED | REGISTERED | XX CANCER CENTER | ALREADY SET | 2019/1/31 10:00 |
| 2018/12/26 | PA05 | TEST COMPLETED | REGISTERED | ⊙ UNREGISTERED | XX CANCER CENTER | ALREADY SET | 2019/1/31 11:00 |
| 2018/12/26 | PA06 | ⊙ ACQUIRE SAMPLE AGAIN | REGISTERED | UNREGISTERED | YY HOSPITAL | ALREADY SET | ⊙ 2019/2/4 15:00 |
| 2019/1/7 | PA11 | ⊙ TEST CANCELED | PARTIALLY REGISTERED | UNREGISTERED | ZZ HOSPITAL | ALREADY SET | ⊙ 2019/2/6 13:00 |
| 2019/1/7 | PA12 | SAMPLE TRANSPORT COMPLETED | PARTIALLY REGISTERED | UNREGISTERED | XY HOSPITAL | UNSET | MEETING SETUP |
| 2019/1/11 | PA13 | SAMPLE PREPARATION COMPLETED | UNREGISTERED | UNREGISTERED | ZX HOSPITAL | UNSET | MEETING SETUP |
| 2019/1/15 | PA14 | PREPARING SAMPLE | UNREGISTERED | UNREGISTERED | XY CANCER CENTER | UNSET | MEETING SETUP |
| ... | | | | | ... | | |

SCHEDULE OF EXPERT MEETING 160
170

OPERATION AND MANAGEMENT OF EXPERT MEETING

RESERVATION LIST OF EXPERT MEETING — R7

| SCHEDULED MEETING DATE | | SELECT |
|---|---|---|
| 2019/01/07 | 10:00–12:00 | ● |
| 2019/01/07 | 13:00–15:00 | ○ |
| 2019/01/14 | 13:00–15:00 | ○ |
| ... | | |

EXPERTS INTENDING TO PARTICIPATE — R8

| FULL NAME | ROLE | SPECIALTY | SELECT |
|---|---|---|---|
| XXXX | GENETIC COUNSELOR | — | ☑ |
| YYYY | BIOINFORMATICIAN | — | ☐ |
| ZZZZ | PHARMACOTHERAPY SPECIALIST | LUNG CANCER | ☑ |
| ... | | | |

180

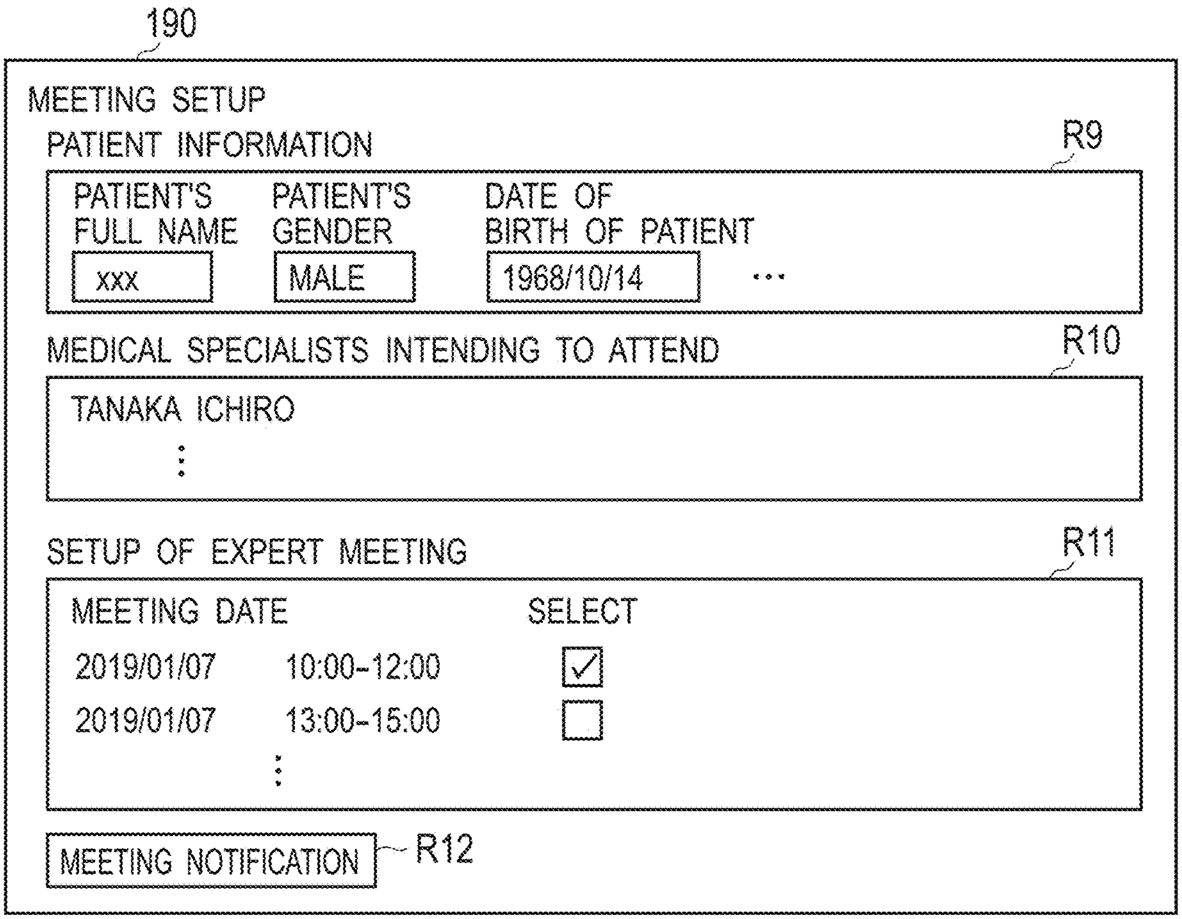

FIG. 37

```
                                                                    190
┌─────────────────────────────────────────────────────────────────────┐
│ MEETING SETUP                                                       │
│  PATIENT INFORMATION                                        R9      │
│  ┌───────────────────────────────────────────────────────────────┐  │
│  │ PATIENT'S    PATIENT'S   DATE OF                              │  │
│  │ FULL NAME    GENDER      BIRTH OF PATIENT                     │  │
│  │ [xxx]        [MALE]      [1968/10/14]    ...                  │  │
│  └───────────────────────────────────────────────────────────────┘  │
│                                                                     │
│  MEDICAL SPECIALISTS INTENDING TO ATTEND                    R10     │
│  ┌───────────────────────────────────────────────────────────────┐  │
│  │ TANAKA ICHIRO                                                 │  │
│  │       :                                                       │  │
│  └───────────────────────────────────────────────────────────────┘  │
│                                                                     │
│  SETUP OF EXPERT MEETING                                    R11     │
│  ┌───────────────────────────────────────────────────────────────┐  │
│  │ MEETING DATE              SELECT                              │  │
│  │ 2019/01/07   10:00-12:00    ☑                                 │  │
│  │ 2019/01/07   13:00-15:00    ☐                                 │  │
│  │       :                                                       │  │
│  └───────────────────────────────────────────────────────────────┘  │
│  [MEETING NOTIFICATION]─R12                                         │
└─────────────────────────────────────────────────────────────────────┘
```

| PATIENT ID | TEST REQUEST ID | TEST RESULT | PATIENT'S FULL NAME | GENDER | NAME OF FACILITY FOR EXPERT MEETING | DATE AND TIME OF EXPERT MEETING | RELATED INFORMATION |
|---|---|---|---|---|---|---|---|
| PA01 | T01 | ... | TANAKA ICHIRO | MALE | ... | 2019/2/10 2 : 00pm | DISPLAY RELATED INFORMATION |
| PA02 | T02 | ... | xxxxx | MALE | ... | 2019/4/14 1 : 00pm | DISPLAY RELATED INFORMATION |
| PA03 | T03 | ... | yyyyy | FEMALE | ... | 2019/5/15 10 : 00am | DISPLAY RELATED INFORMATION |
| PA04 | T04 | ... | XXX | MALE | XX CANCER RESEARCH CENTER | ... | DISPLAY RELATED INFORMATION |
| ... | ... | ... | ... | ... | ... | ... | DISPLAY RELATED INFORMATION |

| | GROUP | MEETING DATE |
|---|---|---|
| ☑ | XX HOSPITAL GROUP A | 2019/2/10 |
| ☐ | XX HOSPITAL GROUP B | 2019/4/14 |
| ☐ | YY HOSPITAL GROUP A | 2019/5/15 |
| | ... | ... |

| PATIENT ID | TEST REQUEST ID | PATIENT'S FULL NAME | GENDER | RELATED INFORMATION |
|---|---|---|---|---|
| PA01 | T01 | TANAKA ICHIRO | MALE | DISPLAY RELATED INFORMATION |
| PA03 | T03 | yyyyy | FEMALE | DISPLAY RELATED INFORMATION |

| MUTATION | MUTATION ID |
|---|---|
| ... | ... |
| EGFR T790M | aaa |
| BRAF V600E | bbb |
| ... | ... |

| THERAPEUTIC AGENT | MEDICAMENT ID |
|---|---|
| ... | ... |
| MEDICAMENT A | AAA |
| MEDICAMENT B | BBB |
| ... | ... |

METHOD OF SUPPORTING INTERPRETATION OF GENETIC INFORMATION BY MEDICAL SPECIALIST, INFORMATION MANAGEMENT SYSTEM, AND INTEGRATED DATA MANAGEMENT DEVICE

CROSS REFERENCE TO RELATED APPLICATIONS

This application claims priority from to prior Japanese Patent Application No. 2019-041671 filed with the Japan Patent Office on Mar. 7, 2019, the entire contents of which are incorporated herein by reference.

BACKGROUND

The disclosure relates to a method of supporting interpretation of genetic information, and so on.

In recent years, genetic tests for testing mutations in specific genes have been performed for purposes, e.g. to confirm the presence or absence of genetic diseases and the effectiveness of medicaments. Particularly in cancer treatment, research has been promoted on cancer genomic medicine involving: examining each patient by a gene panel test capable of comprehensively examining many genes at once to find a mutation using a next-generation sequencer or the like; and determining a treatment policy suitable for the patient based on the results.

Here, the patients' electronic medical records, pathological images, and various test results of the gene panel tests, which are helpful in determining a treatment policy suitable for each patient, are managed by different systems in a medical facility. Japanese Patent Application Publication No. 2018-533123 ("Patent Document 1") discloses an informatic platform that aggregates electronic medical records, pathological images, and results of tests (e.g. gene panel tests), distributed in a medical facility, and supports the determination of a patient's treatment policy.

In a case of determining a treatment policy for each patient based on a result of a gene panel test, it is important to hold an expert meeting by a group of experts capable of medical interpretation, and to determine an optimal treatment policy for the patient by the multiple experts. This expert meeting is also called an "expert panel." An expert meeting is held with the participation of multiple experts, such as an attending physician, pathologist, bioinformatics expert, genetic counselor, molecular genetics researcher, and clinical laboratory technician at a test facility. The expert meeting determines the treatment policy for each patient by comprehensively discussing: clinical information from the medical facility, such as electronic medical records and pathological images of the patient; information from the test facility, such as the test result of the gene panel test; the genetic backgrounds of the patient; the latest academic knowledge; and the like. In addition to multiple experts who belong to either a medical facility or a test facility, experts who do not belong to a specific facility may participate in the expert meeting.

In order to hold an expert meeting, it is necessary to provide information necessary to determine a treatment policy to experts belonging to different facilities and to coordinate the schedule of the expert meeting such that the experts can participate. With the spread of genomic medicine in the future, the number of expert meetings held is expected to increase significantly. A great deal of labor may be required in order to coordinate the schedule of the expert meeting among the experts to participate in the expert meeting, and to provide each expert with correct and appropriate information that will be referred to in the expert meeting.

One or more aspects aim to support an expert meeting in which experts belonging to different facilities participate.

SUMMARY

According to one or more aspects, a method of supporting an expert meeting of medical specialists to interpret genetic information, may include: accepting a test request for genetic information on a patient; extracting test progress information that is stored in association with the accepted test request and indicates progress of a test for the test request, and schedule information on a schedule of the expert meeting to interpret the genetic information obtained in the test for the test request; and displaying the extracted test progress information and the extracted schedule information on terminal devices of the medical specialists.

According to one or more aspects, an information management system that supports an expert meeting of medical specialists to interpret genetic information, may include: a terminal device including a display unit; and an integrated data management device including a controller and a memory. The controller of the integrated data management device may be configured to: accept a test request for genetic information on a patient; extract, from the memory, test progress information that is stored in association with the accepted test request and indicates progress of a test for the test request, and schedule information on a schedule of the expert meeting to interpret the genetic information obtained in the test for the test request; and display, on the display unit of the terminal device, the extracted test progress information and the extracted schedule information.

According to one or more aspects, an integrated data management device that supports an expert meeting of medical specialists to interpret genetic information, may include: a controller; and a memory. The controller may be configured to: accept a test request for genetic information on a patient; extract, from the memory, test progress information that is stored in association with the accepted test request and indicates progress of a test for the test request, and schedule information on a schedule of the expert meeting to interpret the genetic information obtained in the test for the test request; and transmit information to display the extracted test progress information and the extracted schedule information on terminal devices of the medical specialists.

BRIEF DESCRIPTION OF DRAWINGS

FIG. 7 is a diagram illustrating an example of a GUI displayed on a terminal device for inputting test request information;

FIG. 8 is a diagram illustrating an example of a facility table;

FIG. 9 is a diagram illustrating an example of a gene panel table;

FIG. 10 is a diagram illustrating an example of a user registration table;

FIG. 13 is a diagram illustrating an example of a GUI including entry fields for a patient's disease name and disease ID;

FIG. 14 is a diagram illustrating an example of a master table;

FIG. 17 is a diagram illustrating an example of a group table;

FIG. 18 is a diagram illustrating an example of a schedule table;

FIG. 19 is a diagram illustrating an example of an integrated ID table;

FIG. 20 is a diagram illustrating another example of an integrated ID table;

FIG. 21 is a diagram illustrating an example of a patient information table;

FIG. 22 is a diagram illustrating an example of a disease table;

FIG. 23 is a diagram illustrating an example of a pathological image table;

FIG. 24 is a diagram illustrating an example of a test result table;

FIG. 25 is a diagram illustrating an example of an annotation information table;

FIG. 26 is a diagram illustrating an example of a role table;

FIG. 27 is a diagram illustrating an example of an access authority management table;

FIG. 28 is a diagram illustrating an example of a screen displayed when logging in to a data integration server from a terminal device at a transportation establishment;

FIG. 29 is a diagram illustrating an example of a GUI displayed on a terminal device in order to receive an input of a reservation for an expert meeting;

FIG. 30 is a diagram illustrating an example of a GUI displayed on a terminal device in order to receive an input of a reservation for an expert meeting;

FIG. 33 is an example of a GUI, including information on a list of test requests and a schedule of an expert meeting, displayed on a terminal device used by a medical specialist;

FIG. 37 is a diagram illustrating an example of a GUI displayed on a terminal device in order to receive settings on a schedule of an expert meeting;

FIG. 38 is a diagram illustrating an example of a GUI, including schedules of expert meetings and information on each expert meeting, displayed on a terminal device of a medical specialist;

FIG. 39 is a diagram illustrating an example of a GUI, including schedules of expert meetings and information on each expert meeting, displayed on a terminal device of a medical specialist;

FIG. 40 is a diagram illustrating an example of a GUI including information on each expert meeting on a terminal device of a medical specialist;

FIG. 48 is a diagram illustrating an example of a mutation table;

FIG. 49 is a diagram illustrating an example of a therapeutic agent table;

DETAILED DESCRIPTION

Figure 35:
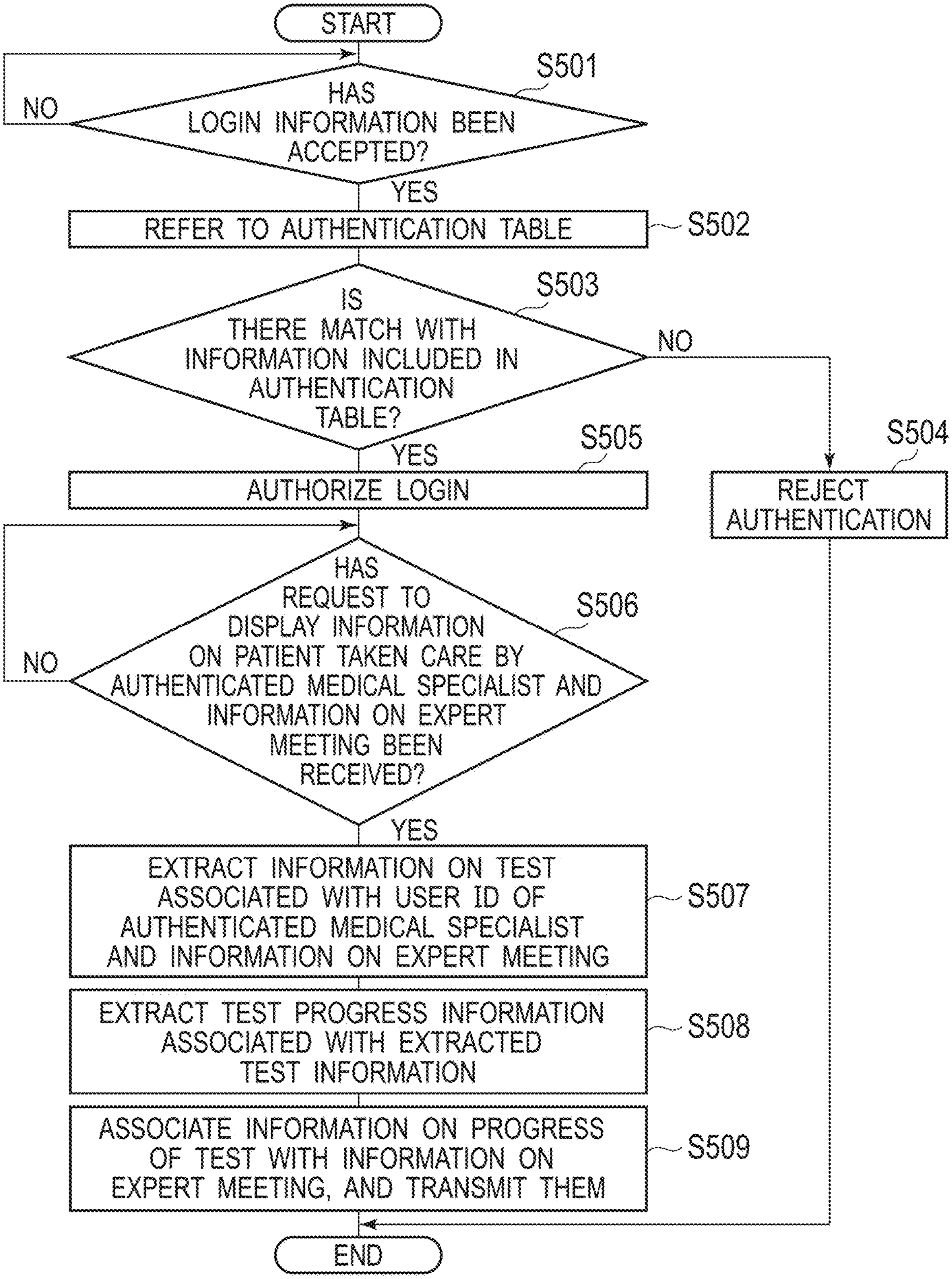
FIG. 35 is a diagram illustrating an example of a flow of the processing performed by a controller of an integrated data management device in order to display information, formed by associating information on the progress of a test with information on a schedule of an expert meeting, on a terminal device of a medical specialist.

With reference to FIG. 35, in order to solve the above problem, one or more aspects include a method of supporting an expert meeting of multiple medical specialists to interpret genetic information, including: accepting a test request for genetic information on a patient (S13 in FIG. 5); extracting test progress information that is stored in association with the accepted test request and indicates progress of a test for the test request, and schedule information on a schedule of the expert meeting to interpret the genetic information obtained in the test for the test request (S507 and S508); and displaying the extracted test progress information and schedule information on terminal devices of the medical specialists (S509).

Figure 2:
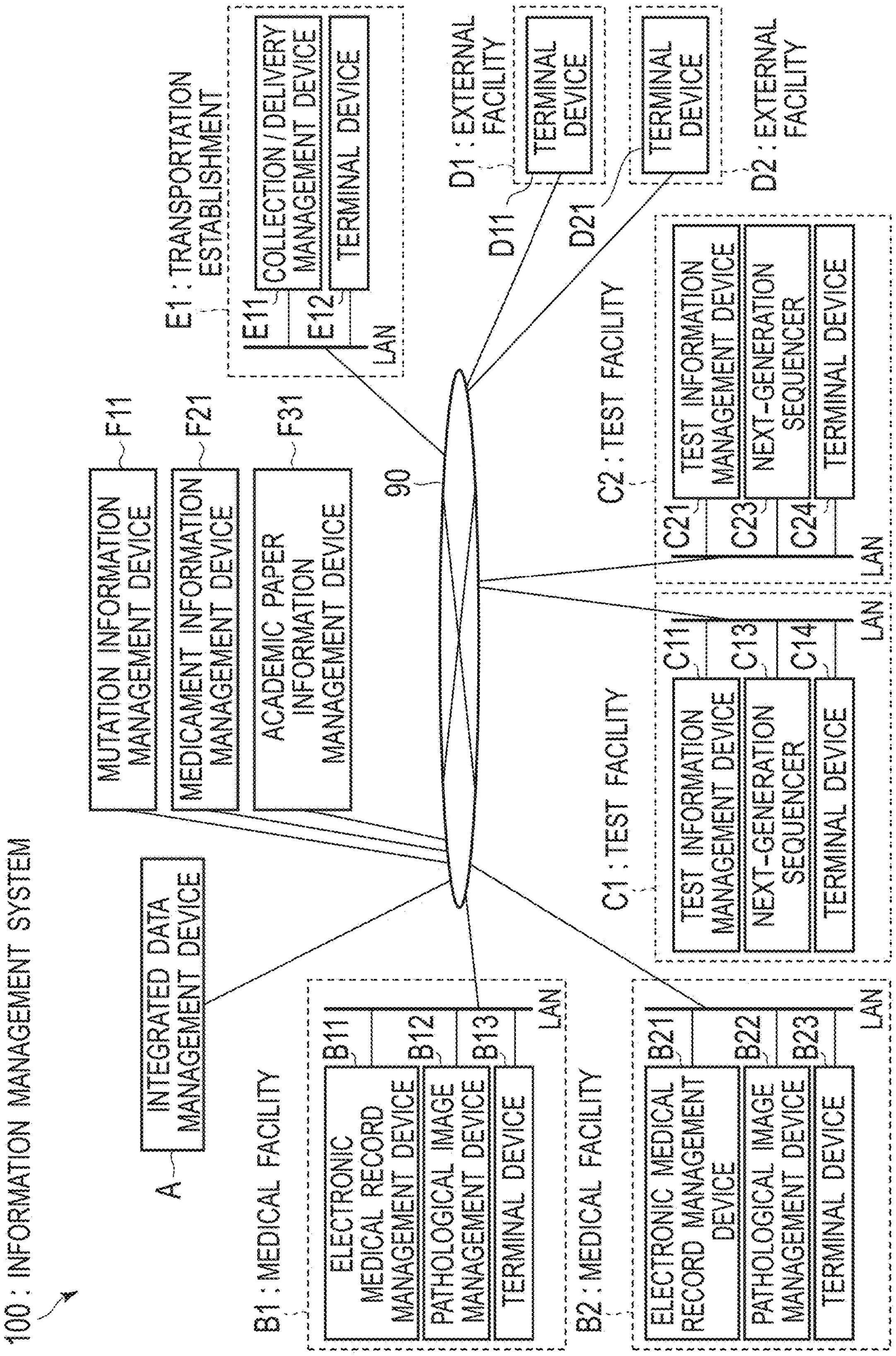
FIG. 2 is a diagram illustrating a configuration example of an information management system.
Figure 3:
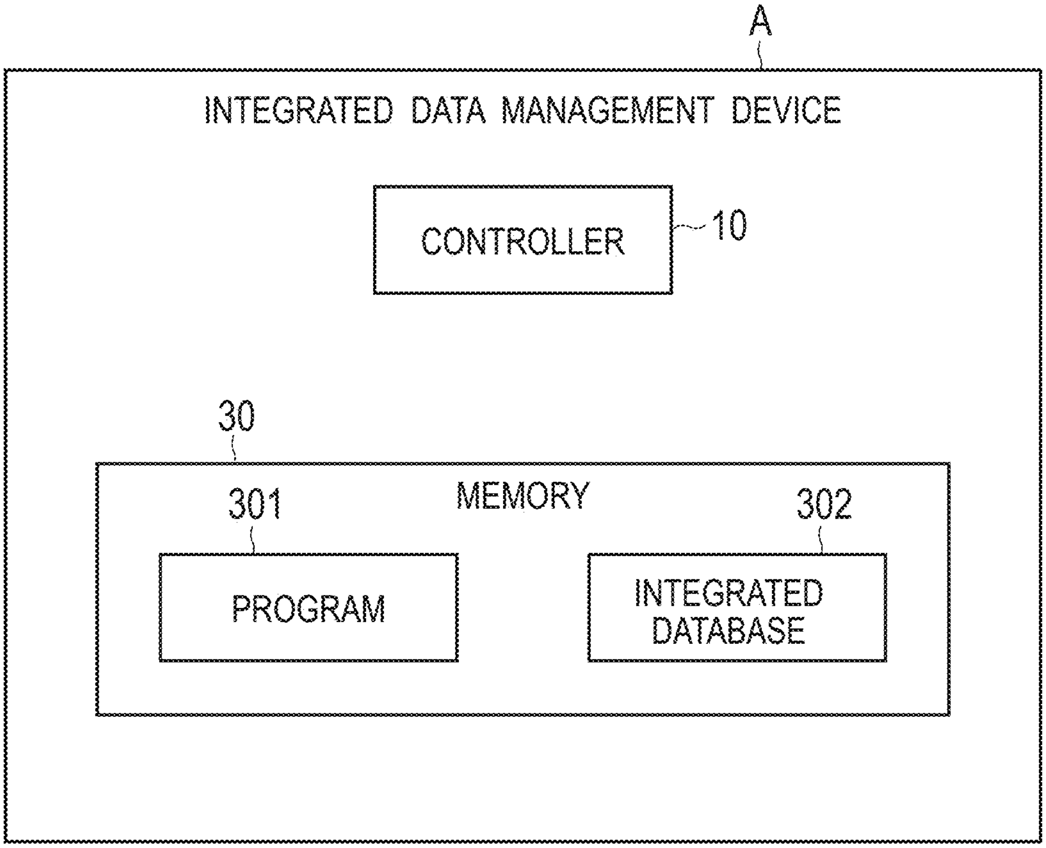
FIG. 3 is a block diagram illustrating a configuration example of an integrated data management device.

In addition, with reference to FIG. 2, one or more aspects include an information management system (100) that supports an expert meeting of multiple medical specialists to interpret genetic information, including: a terminal device (B13) including a display unit; and an integrated data management device (A) including a controller (10 in FIG. 3) and a memory (30 in FIG. 3). The controller (10 in FIG. 3) of the integrated data management device (A) accepts a test request for genetic information on a patient, extracts test progress information that is stored in association with the accepted test request and indicates progress of a test for the test request, and schedule information on a schedule of the expert meeting for interpretation of the genetic information obtained in the test for the test request, and displays the extracted test progress information and schedule information on the display unit of the terminal device (B13).

In addition, with reference to FIG. 3, one or more aspects include an integrated data management device (A) that supports an expert meeting of multiple medical specialists to interpret genetic information, including: a controller (10); and a memory (30). The controller (10) accepts a test request for genetic information on a patient, extracts test progress information that is stored in association with the accepted test request and indicates progress of a test for the test request, and schedule information on a schedule of the expert meeting for interpretation of the genetic information obtained in the test for the test request, and transmits information that causes terminal devices (B13 in FIG. 2) of the medical specialists to display the extracted test progress information and schedule information.

One or more aspects make it possible to support an expert meeting in which experts belonging to different facilities participate.

Hereinafter, an embodiment is described in detail.

(Genetic Test)

Figure 1:
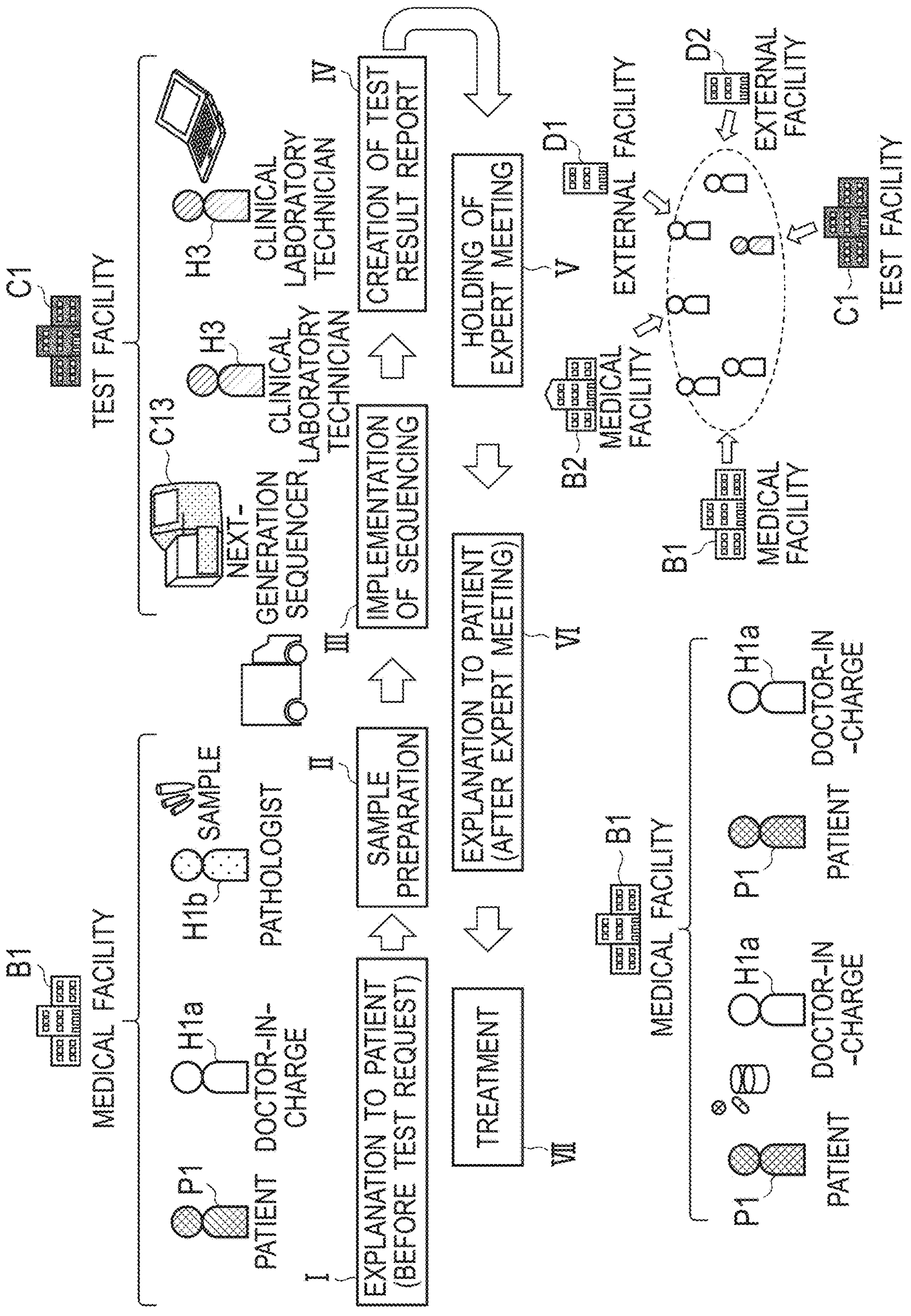
FIG. 1 is a diagram illustrating an example of a flow of a genetic test and treatment.

First, a genetic test is described with reference to FIG. 1. FIG. 1 is a diagram illustrating an example of the flow of a genetic test and treatment. Here, as an example of the genetic test, description is provided for the flow in the case of performing a gene panel test. The gene panel test is a test capable of comprehensively examining many genes at once to find a genetic mutation for each patient using a next-generation sequencer or the like.

<Step I: Explanation to Patient (Before Test Request)>

Step I is a step of explaining advantages and points of attention regarding the gene panel test from a doctor-in-charge H1*a*, who is a medical specialist, to a patient P1 in a medical facility B1. When the consent of the patient P1 to perform the gene panel test is obtained, the processing proceeds to step II.

<Step II: Sample Preparation>

Step II is a step in which a pathologist H1*b*, who is a medical specialist, prepares a sample to be subjected to a gene panel test in the medical facility B1. The sample is a pathological tissue sample that allows the extraction of a gene to be subjected to a gene panel test. The sample is, for example, FFPE (Formalin-Fixed Paraffin-Embedded) in which the pathological tissue of the patient P1 is embedded in formalin-fixed paraffin. When a pathological tissue sample is prepared for pathological diagnosis by the pathologist H1*b* prior to step II, this pathological tissue sample may be used for the gene panel test.

Note that, in the medical facility B1, a blood sample may be further collected from the patient P1 as a sample for extracting a wild-type gene to be compared when detecting a genetic mutation in a pathological tissue. In this case, multiple samples of FFPE sample and blood sample are provided for a single gene panel test.

The pathological tissue sample and blood sample of the patient P1 are transported from a medical facility to the test facility C1 that performs the gene panel test. Note that the transportation of the FFPE sample and blood sample of the patient P1 may be performed by a transportation company that handles transportation, or may be performed directly by the test facility C1 that has received a request for the gene panel test.

<Step III: Implementation of Sequencing>

Step III is a step in which, in the test facility C1 that has received the pathological tissue sample and blood sample of the patient P1, a clinical laboratory technician H3 who is a medical specialist performs pretreatment of extracting genes from the pathological tissue sample and blood sample, and causes the next-generation sequencer C13 to read the base sequences of the extracted genes.

<Step IV: Creation of Test Result Report>

Step IV is a step in which, in the test facility C1, the clinical laboratory technician H3 analyzes the base sequences read by the next-generation sequencer C13, specifies the presence or absence of a mutation in the base sequences, the position of the mutation, the type of the mutation, and the like, and creates a test result report.

The test result report includes information on a gene panel used for the test, information on a test result, and information on a quality evaluation index for evaluating the quality of the test. The information on the test result includes, for example, the presence or absence of a mutation in the base sequences, the position of the mutation, and the type of the mutation. In addition, the test result report may include medicament information and academic paper information on the mutation detected by the gene panel test.

Here, the "mutation" includes replacement, deletion, and insertion of a gene nucleotide as well as gene fusion and copy number variation. The "replacement" refers to a phenomenon where at least one base in a gene sequence becomes a different base. The "replacement" includes point mutations and single nucleotide polymorphisms. The "deletion" and "insertion" are also described as "InDel (Insertion and/or Deletion)." InDel is a phenomenon where at least one base is inserted and/or deleted in a gene sequence. The "gene fusion" refers to a phenomenon where a sequence on the 5' side of a gene and a sequence on the 3' end side of another gene are ligated by translocation of the chromosome or the like. The "copy number variation" means that the number of copies on the genome per cell differs between individuals. Specific examples thereof include VNTR (Variable Nucleotide of Tandem Repeat), STRP (Short Tandem Repeat Polymorphism), and gene amplification.

In addition, the "information on a quality evaluation index" is an index for evaluating whether or not the gene panel test has been properly performed. Examples thereof include the ratio of the read base sequences to the total base sequences contained in the gene to be analyzed, the depth of coverage of the read base sequences, and the presence or absence of a mutation detected in a standard gene contained in a quality control specimen. Here, the quality control specimen is a gene specimen containing a known mutation to be read in the sequencing of the next-generation sequencer C13.

<Step V: Holding of Expert Meeting>

Step V is a step in which multiple medical specialists, who are experts for medically interpreting the test result of the gene panel test, from medical facilities B1 and B2, test facilities C1 and C2, external facilities D1 and D2, and the like, participate in and hold an expert meeting. In the expert meeting, the multiple medical specialists discuss variously with reference to the test result report of the gene panel test, the clinical information on the patient P1, the genetic background of the patient P1, the latest academic knowledge, and the like, and determine a treatment policy expected to be effective for each patient. The "clinical information" on the patient P1 referred to at the expert meeting is, for example, an electronic medical record created in the medical facility B1 where the patient P1 is examined and a pathological image captured by the pathologist H1*b*.

Here, examples of the "medical specialists" who participate in the expert meeting include: (1) a doctor-in-charge H1*a*, a pathologist H1*b*, and a cancer pharmacotherapy specialist for the patient P1, who belong to the medical facility B1; (2) a clinical laboratory technician H3 who belongs to the test facility C1; and (3) a bioinformatics specialist, a genetic counselor, a molecular genetics researcher, and a genetic medicine specialist who belong to external facilities D1 and D2, such as research institutions and universities. That is, the multiple medical specialists belonging to different facilities and organizations may participate in the expert meeting. The expert meeting may be a meeting held at a certain medical facility B1 to which medical specialists come together, or may be in the form of a video meeting in which some or all medical specialists participate via a communication network.

<step VI: Explanation to Patient (After Holding of Expert Meeting)>

Step VI is a step in which, in the medical facility B1, the doctor-in-charge H1*a* explains to the patient P1 the treatment policy for the patient P1 determined by the discussion at the expert meeting. If the consent of the patient P1 is obtained, the processing proceeds to step VII.

<Step VII: Treatment>

Step VII is a step of performing treatment for the patient P1 in the medical facility B1 based on the treatment policy determined by the discussion at the expert meeting. In the case of performing a treatment requiring highly specialized knowledge and experience, the treatment may be performed in cooperation with another medical facility B2 having a system capable of smoothly performing the treatment, instead of the medical facility B1 where the patient P1 is examined.

In step V, in order to hold an expert meeting, it is necessary to collect various types of information referred to by multiple medical specialists without excess or deficiency and to provide each medical specialist in advance. However, for example, the clinical information of the patient P1, such as an electronic medical record and pathological image, is managed in the medical facility B1, and the test result of the gene panel test is managed in the test facility C1. For this reason, as preparation for an expert meeting, it is necessary to perform a labor-intensive work of obtaining information referred to in the expert meeting from multiple facilities and providing it to each medical specialist.

One or more aspects associate the test result of the request for a gene panel test of the patient P1 with the clinical information on the patient P1, and provide the associated test result and clinical information to the medical specialists. This makes it possible to support the preparation for an expert meeting.

<Configuration of Information Management System 100>

First, the structure of an information management system 100 according to one or more aspects is described with reference to FIG. 2. FIG. 2 is a diagram illustrating a configuration example of the information management system 100.

The information management system 100 includes an integrated data management device A and at least one terminal device B13, B23, C14, C24, D11, D21, and E12 installed in various facilities. The integrated data management device A and the terminal devices B13, B23, C14, C24, D11, D21, and E12 are communicably connected via a communication network 90.

The information management system 100 only needs to include the integrated data management device A and at least one of the multiple terminal devices B13, B23, C14, C24, D11, D21, or E12, such as at least one of: the multiple terminal devices B13; B23; C14; C24; D11; D21; and E12. The other devices installed in the medical facilities B1 and B2, the test facilities C1 and C2, the external facilities D1 and D2, and the transportation establishment E1 are not essential components. In addition, the details of the other devices installed in the medical facilities B1 and B2, the test facilities C1 and C2, the external facilities D1 and D2, and the transportation establishment E1 are described later.

[Integrated Data Management Device A]

The integrated data management device A is a computer that functions as a server. The integrated data management device A is communicably connected, via the communication network 90, to various equipment, such as terminal devices installed in the medical facilities B1 and B2, the test facilities C1 and C2, the external facilities D1 and D2, and the transportation establishment E1 as well as to a mutation information management device F11, a medicament information management device F21, and an academic paper information management device F31. Note that an embodiment illustrates an example in which the integrated data management device A is a cloud server, but is not limited to this.

FIG. 3 is a block diagram illustrating a configuration example of the integrated data management device A. The integrated data management device A includes a controller 10 that is a CPU (Central Processing Unit) and a memory 30. The memory 30 stores a program 301 used for the operation of the information management system 100, and an integrated database 302.

The function executed by the integrated data management device A is achieved by the controller 10 reading the program 301 stored in the memory 30 and developing and executing the program 301 in a RAM (Random Access Memory).

The integrated database 302 stores various tables and data used when the controller 10 executes various functions. The details of various tables and data stored in the integrated database 302 are described later.

[Medical Facilities B1 and B2]

Back to FIG. 2, the medical facilities B1 and B2 are medical institutions, such as hospitals to which medical specialists, such as the doctor-in-charge H1*a* of the patient P1, belong.

The medical facilities B1 and B2 may include a core base hospital having advanced functions that lead the field of cancer genomic medicine. In addition, the medical facilities B1 and B2 may include a collaborative base hospital that is a medical institution having a system capable of smoothly performing cancer treatment and the like in cooperation with a core base hospital. In the case of performing a gene panel test on the patient P1 at the collaborative base hospital, interpretation of test results of the patient P1 at the collaborative base hospital and determination of a treatment policy may be conducted at an expert meeting hosted by the core base hospital.

Note that the doctor-in-charge H1*a* and the pathologist H1*b* belonging to the medical facilities B1 and B2 may be medical specialists who participate in the expert meeting.

In the medical facilities B1 and B2, electronic medical record management devices B11 and B21, pathological image management devices B12 and B22, and terminal devices B13 and B23 are installed. In addition, a LAN (Local Area Network) is provided in each of the medical facilities B1 and B2. Hereinafter, a LAN in a medical facility is referred to as an "in-medical-facility LAN." The in-medical-facility LAN is communicably connected to the communication network 90. To the respective in-medical-facility LANs of the medical facilities B1 and B2, the electronic medical record management devices B11 and B21, the pathological image management devices B12 and B22, and the terminal devices B13 and B23 are communicably connected.

The electronic medical record management devices B11 and B21 are computers that function as a server for managing the electronic medical record information on patients at the medical facility B1. In addition, the pathological image management devices B12 and B22 are computers that function as a server for managing pathological images captured in the medical facility B1.

The terminal devices B13 and B23 are computer terminals used by medical specialists belonging to the medical facilities B1 and B2. The terminal devices B13 and B23 are, for example, personal computers, tablet terminals, smartphones, and the like. The terminal devices B13 and B23 include: a communication unit with other devices; an input unit, such as a keyboard and a microphone; a display unit, such as a monitor; an output unit, such as a speaker; and the like.

[Test Facilities C1 and C2]

The test facilities C1 and C2 are contract test organizations to which medical specialists belong, such as the clinical laboratory technician H3 who performs a gene panel test in response to a test request from the medical facilities B1 and B2 and creates a test result report.

When medical facilities B1 and B2 have a test room allowing a gene panel test, the gene panel test may be performed in the medical facilities B1 and B2. In this case, the medical facilities B1 and B2 also function as the test facilities C1 and C2.

Note that the clinical laboratory technician H3 belonging to the test facilities C1 and C2 may be a medical specialist who participates in the expert meeting.

In the test facilities C1 and C2, test information management devices C11 and C21, next-generation sequencers C13 and C23, and terminal devices C14 and C24 are installed. In addition, a LAN is provided in each of the test facilities C1 and C2. Hereinafter, a LAN in a test facility is referred to as an "in-test-facility LAN." The in-test-facility LAN is communicably connected to the communication network 90. To the respective in-test-facility LANs of the test facilities C1 and C2, the test information management devices C11 and C21, the next-generation sequencers C13 and C23, the test facilities C1 and C2, and the terminal devices C14 and C24 are communicably connected.

The test information management devices C11 and C21 are computers that function as a server for managing test information.

The next-generation sequencers C13 and C23 are various devices used for tests performed at the test facility C1, and are, for example, next-generation sequencers that can measure the base sequences of cleaved DNA fragments simultaneously in parallel.

The terminal devices C14 and C24 are computer terminals used by medical specialists belonging to the test facilities C1 and C2. The terminal devices C14 and C24 are, for example, personal computers, tablet terminals, smartphones, and the like. The terminal devices C14 and C24 include: for example, a communication unit with other devices; an input unit, such as a keyboard and a microphone; a display unit, such as a monitor; an output unit, such as a speaker; and the like.

[External Facilities D1 and D2]

The external facilities D1 and D2 are establishments and laboratories other than the medical facilities B1 and B2 and the test facilities C1 and C2 and to which experts belong. Examples of medical specialists belonging to the external facilities D1 and D2 include bioinformatics experts, genetic counselors, and molecular genetics researchers.

Note that the bioinformatics experts, the genetic counselors, and the molecular genetics researchers belonging to the external facilities D1 and D2 may be medical specialists who participate in the expert meeting.

In the external facilities D1 and D2, the terminal devices D11 and D21 are installed. In addition, a LAN is provided in each of the external facilities D1 and D2. Hereinafter, a LAN in an external facility is referred to as an "in-external-facility LAN." The in-external-facility LAN is communicably connected to the communication network 90. To the in-external-facility LANs of the external facilities D1 and D2, the terminal devices D11 and D21 are communicably connected.

The terminal devices D11 and D21 are computer terminals used by medical specialists belonging to the external facilities D1 and D2. The terminal devices D11 and D21 are, for example, personal computers, tablet terminals, smartphones, and the like. The terminal devices D11 and D21 include: a communication unit with other devices; an input unit, such as a keyboard and a microphone; a display unit, such as a monitor; an output unit, such as a speaker; and the like.

[Transportation Establishment E1]

The transportation establishment E1 is an establishment of a transportation company to which transporters belong.

The transporters carry samples from the medical facilities B1 and B2, as the test request sources or the test requester of the gene panel test, to the test facilities C1 and C2, as the test request destinations.

When the test facilities C1 and C2 have a sample transportation function, the transporters belonging to the test facilities C1 and C2 may receive samples from the medical facilities B1 and B2 and transport the samples to the test facilities C1 and C2. In this case, the test facilities C1 and C2 also function as the transportation establishment E1.

Note that, usually, transporters are not medical specialists and do not participate in expert meetings.

In the transportation establishment E1, a collection/delivery management device E11 and a terminal device E12 are installed. In addition, a LAN is provided in the transportation establishment E1. Hereinafter, a LAN in a transportation establishment is referred to as an "in-transportation-establishment LAN." The in-transportation-establishment LAN is communicably connected to the communication network 90. To the in-transportation-establishment LAN of the transportation establishment E1, the collection/delivery management device E11 and the terminal device E12 are communicably connected.

The collection/delivery management device E11 is a computer that functions as a server for managing collection/delivery of samples.

The terminal device E12 is a computer terminal used by transporters belonging to the transportation establishment E1. The terminal device E12 is communicably connected to the integrated data management device A and the like via the communication network 90. The terminal device E12 is, for example, a personal computer, a tablet terminal, a smartphone, and the like. The terminal device E12 includes: a communication unit with other devices; an input unit, such as a keyboard and a microphone; a display unit, such as a monitor; an output unit, such as a speaker; and the like. Note that the terminal device E12 may be connected to an RFID reader and a barcode reader for acquiring sample identification information.

[External Information Management Device]

The information management system 100 is communicably connected to an external information management device via the communication network 90. The external information management device is, for example, the mutation information management device F11, the medicament information management device F21, the academic paper information management device F31, or the like.

The mutation information management device F11, the medicament information management device F21, and the academic paper information management device F31 are computers that function as a server. The information managed by the mutation information management device F11, the medicament information management device F21, and the academic paper information management device F31 is used as annotation information to be given to the mutations identified by the gene panel test performed at the test facilities C1 and C2.

Examples of the information managed by the mutation information management device F11 include the COSMIC database (webpage, www.sanger.ac.uk/genetics/CGP/cosmic/), the ClinVar database (webpage, www.ncbi.nlm.nih.gov/clinvar/), and dbSNP (webpage, www.ncbi.nlm.nih.gov/SNP/).

Note that the information managed by the mutation information management device F11 may be a database including mutation frequency information for each race or animal type. Examples of databases having such information include HapMap Genome Browser release #28, Human Genetic Variation Browser (webpage, www.genome.med.kyoto-u.ac.jp/SnpDB/index.html), and 1000 Genomes (webpage, www.1000genomes.org/). From these databases, Japanese mutation frequency information and the like can be obtained, for example. Note that the mutation information is not limited to information on genetic mutation, but may include information on polymorphism and methylation.

Information managed by the medicament information management device F21 may include, for example, information on the composition, structural formula, usage, side effects, and the like of various approved medicaments, and information on clinical trials of unapproved medicaments.

The information managed by the academic paper information management device F31 may include, for example, information on bibliographic items, text data, and the like of academic papers related to diseases, mutations, and therapeutic agents submitted to scientific journals and the like.

[Security Measures]

Communication between the integrated data management device A and various devices in the medical facilities B1 and B2 preferably uses a VPN (Virtual Private Network). Similarly, it is desirable to use a VPN for communication between the integrated data management device A and various devices in the test facilities C1 and C2. The use of a VPN makes it possible to protect the clinical information on the patient P1 at the medical facilities B1 and B2, the test result, of the gene panel test of the patient P1 at the test facilities C1 and C2, and the like from threats of stealing and falsification by a third party.

In addition, the integrated data management device A is equipped with various APIs (application program interfaces). The integrated data management device A uses the APIs to provide the terminal devices B13, B23, C14, C24, D11, and D21 installed in various facilities with the clinical information on the patient P1 to be discussed at the expert meeting, the test result of the gene panel test, and the like.

Note that, for communication between the integrated data management device A and the terminal devices B13, B23, C14, C24, D11, and D21 installed in various facilities, it is desirable to use encrypted communication, such as SSL (Secure Socket Layer), as a security measure. Thereby, the clinical information on the patient P1 to be discussed in the expert meeting and the test result of the gene panel test can be safely provided to the medical specialists.

(Flow of Genetic Test Using Information Management System 100)

Figure 4:
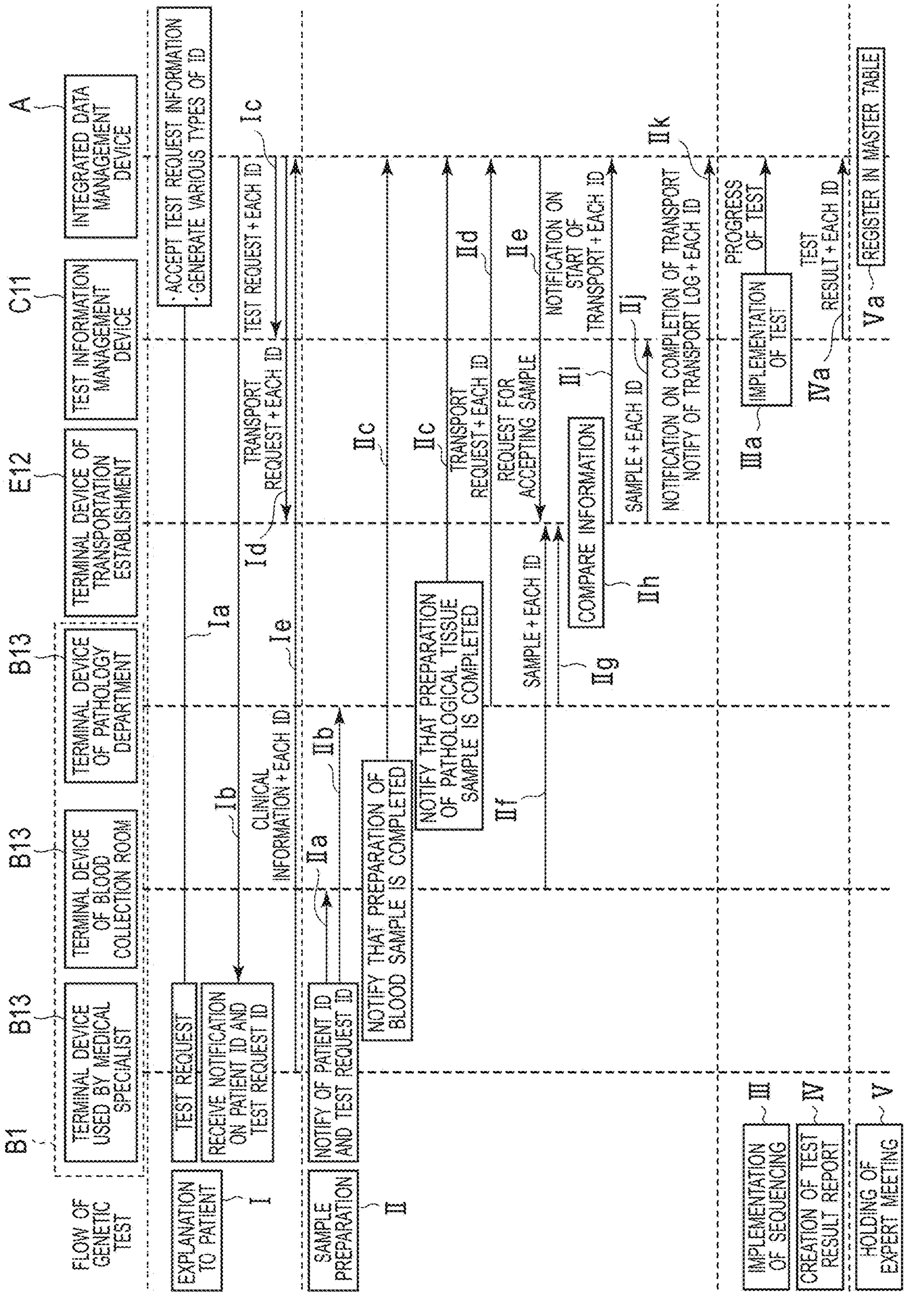
FIG. 4 is a diagram illustrating an example of a flow of a genetic test to which an information management system according to one or more aspects is applied.

Next, the flow of a genetic test using the information management system 100 is described with reference to FIG. 4. FIG. 4 is a diagram illustrating an example of the flow of a genetic test using the information management system 100. Note that FIG. 4 illustrates the flow of a genetic test corresponding to steps I to IV illustrated in FIG. 1. Hereinafter, description is provided as an example for the case where the medical facility B1 requests a gene panel test to the test facility C1.

<Step Ia>

Step Ia is a step in which the integrated data management device A accepts a request for a gene panel test from the terminal device B13 used by the doctor-in-charge H1*a*.

Figures 5, 6:
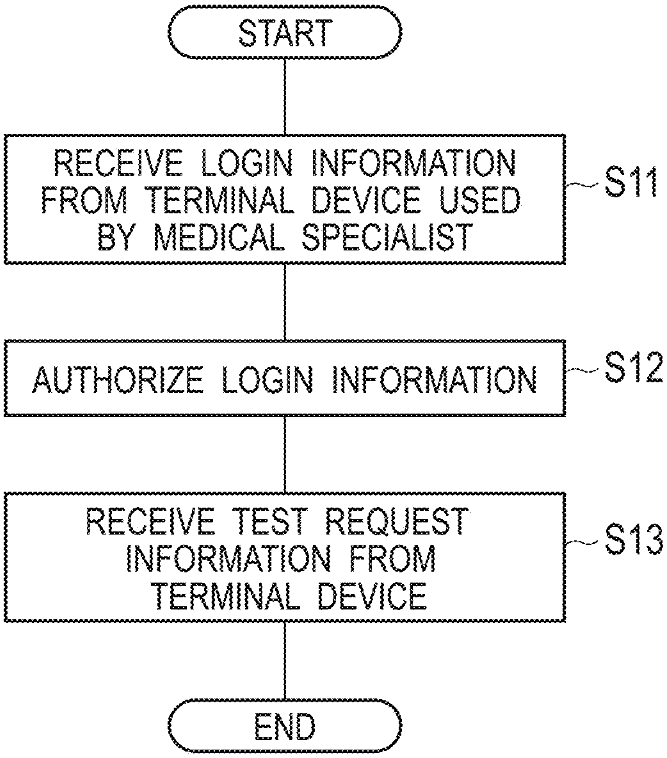
FIG. 5 is a flow diagram illustrating an example of the processing of a test request reception step.
FIG. 6 is a diagram illustrating an example of an authentication table.

The processing in step Ia or the test request reception step is described with reference to FIG. 5. FIG. 5 is a flow diagram illustrating an example of the processing of the test request reception step.

In step Ia, the doctor-in-charge H1*a* first uses the terminal device B13 in the medical facility B1 to start a program for logging in to the information management system 100, and inputs login information.

The integrated data management device A receives login information including a login password and the like from the terminal device B13 (step S11), and refers to an authentication table 38 stored in the integrated database 302 of the integrated data management device A to authorize the login from the terminal device B13 used by the doctor-in-charge H1*a* (step S12).

FIG. 6 is a diagram illustrating an example of the authentication table 38. As illustrated in FIG. 6, in the authentication table 38, a set of an authentication login password set for each user and a user ID of each user is stored.

When the login is authorized by the integrated data management device A, the controller 10 of the integrated data management device A displays a GUI (Graphical User Interface) 130 for inputting test request information illustrated in FIG. 7 on the display unit of the terminal device B13. The controller 10 receives the test request information from the terminal device B13 in response to the input of the doctor-in-charge H1*a* to the GUI 130 (step S13).

[GUI 130 for Inputting Test Request Information]

Description is provided for the GUI 130 displayed on the display unit of the terminal device B13 whose login has been authorized by the integrated data management device A in order for the doctor-in-charge H1*a* to input test request information. FIG. 7 is a diagram illustrating an example of the GUI 130 displayed on the display unit of the terminal device B13 for inputting test request information.

The GUI 130 includes a region R1 for accepting the input of information on the medical facility B1 as a request source facility that requests a test, a region R2 for accepting the input of test request information, and a request button R3 for accepting an instruction to transmit test request information from the terminal device B13 to the integrated data management device A.

The region R1 is provided with, for example, entry fields or sections for accepting inputs of "Facility Name," "Facility ID," "Address," and "Contact Information" as information on the medical facility B1.

Here, the "Facility Name" is the name of the medical facility B1 as the test requester or the request source facility. The "Facility ID" is identification information assigned to each medical facility B1. The integrated data management device A may refer to the medical facility table 21, which is illustrated in FIG. 8 and stored in the integrated database 302, and automatically display the facility ID corresponding to the inputted facility name in the facility ID field.

FIG. 8 is a diagram illustrating an example of the medical facility table 21 stored in the integrated database 302. In the medical facility table 21, multiple facility IDs and the facility names corresponding to the facility IDs are stored in association with each other.

The controller 10 of the integrated data management device A refers to the medical facility table 21 in response to the input of the request source facility name via the GUI 130, and searches for the facility ID corresponding to the inputted facility name. When there is no facility ID corresponding to the inputted request source facility name, the integrated data management device A may newly generate a facility ID of the inputted request source facility, and store the facility name and the generated facility ID in the medical facility table 21 in association with each other.

Alternatively, the controller 10 of the integrated data management device A may be configured to notify the administrator of the integrated data management device A that there is no facility ID corresponding to the inputted facility name. In this case, the administrator of the integrated data management device A sets a facility ID corresponding to the inputted facility name, and newly stores the facility name and the facility ID in the medical facility table 21 in association with each other.

Back to FIG. 7, the "Address" inputted in the region R1 for accepting the input of information on the request source facility is the address of the medical facility B1 that is the facility as the test request source. In addition, the "contact information" is a telephone number or an e-mail address of the medical facility B1 that is the facility as the test request source.

The region R2 is provided with, for example, entry fields or sections for accepting inputs of "Test Type," "Doctor-in-Charge of Patient," "User ID of Doctor-in-Charge," "Patient ID," "Consent of Patient," "Patient's Full Name," "Patient's Gender," "Date of Birth of Patient," "Test Facility," "Test Request Date," "Facility for Interpreting Test Result," and "ID of Facility for Interpreting Test Result" as the test request information.

Here, "Test Type" is information on the type of the requested gene panel test. The type of gene panel test may be, for example, the name of the test, or the name of the gene panel used for the requested gene panel test.

The controller 10 of the integrated data management device A may refer to the gene panel table 22 stored in the integrated database 302, and display a list of the gene panel names assumed to be used in the information management system 100 on the display unit of the terminal device B13 of the medical facility B1. The doctor-in-charge H1*a* can select a gene panel for test request as the test type from the list.

FIG. 9 is a diagram illustrating an example of the gene panel table 22 stored in the integrated database 302. In the gene panel table 22, gene panel IDs and the gene panel names corresponding to the IDs are stored in association with each other. The controller 10 of the integrated data management device A refers to the gene panel table 22, and searches for the gene panel ID corresponding to the inputted gene panel name.

Back to FIG. 7, the "Doctor-in-Charge of Patient" inputted in the region R2 for accepting the input of test request information is the full name or personal name of the doctor-in-charge H1*a* of the patient P1.

In addition, the "User ID of Doctor-in-Charge" is identification information on the doctor-in-charge H1*a* of the patient P1. The user ID is medical specialist identification information for identifying a medical specialist. The controller 10 of the integrated data management device A may refer to the user registration table 23, which is illustrated in FIG. 10 and stored in the integrated database 302, and automatically display the user ID corresponding to the inputted full name of the doctor-in-charge H1*a* in the user ID field.

FIG. 10 is a diagram illustrating an example of the user registration table 23 stored in the integrated database 302. In the user registration table 23, the user IDs, the full names or personal names of the medical specialists, the contact information of the medical specialists, and the specialized fields of the medical specialists are stored in association with each other. Here, the specialized field of the medical specialist is, for example, a type of cancer specialized by medical specialist, such as "lung cancer" and "large intestine cancer".

The controller 10 of the integrated data management device A refers to the user registration table 23 in response to the input of the full name of the doctor-in-charge H1*a* via the GUI 130, and searches for the user ID corresponding to the inputted full name of the doctor-in-charge H1*a*. When there is no user ID corresponding to the inputted full name, the controller 10 may newly generate a user ID of the medical specialist, and store the full name and the generated user ID in the user registration table 23 in association with each other.

Alternatively, the controller 10 of the integrated data management device A may be configured to notify the administrator of the integrated data management device A that there is no user ID corresponding to the inputted full name. In this case, the administrator of the integrated data management device A sets a user ID corresponding to the full name of the medical specialist, and stores the full name and the user ID of the medical specialist in the user registration table 23 in association with each other.

Back to FIG. 7, the "Patient ID" inputted in the region R2 for accepting the input of test request information is identification information given to the patient P1. The patient ID may be a patient ID that is individually assigned to each patient P1 by the medical facility B1 as the test request source. Alternatively, before inputting test request information, the patient ID generated by the controller 10 of the integrated data management device A may be notified from the controller 10 to the terminal device B13 installed in the medical facility B1.

The "Patient's Full Name" inputted in the region R2 is the full name or personal name of the patient P1. The "Patient's Gender" is the gender of the patient P1. The "Date of Birth of Patient" is the date of birth of the patient P1. Here, an entry field of "Age of Patient" may be displayed on the GUI 130 to input the age of the patient P1.

The "Test Request Date" inputted in the region R2 is a date when the test request is transmitted from the terminal device B13 installed in the medical facility B1 to the integrated data management device A. For example, the configuration may be such that, when the GUI 130 for inputting the test request information is displayed on the display unit of the terminal device B13, the date of the day is automatically inputted as the test request date.

The "Test Facility" inputted in the region R2 is the name of the test facility C1 for performing a gene panel test. Instead of the name, a test facility ID corresponding to the test facility C1 may be inputted.

Figures 11, 12:
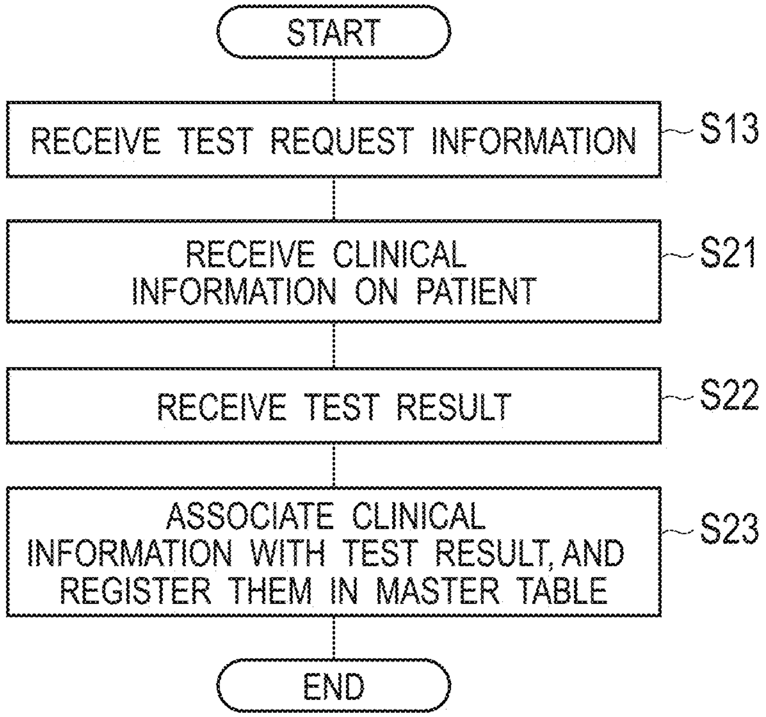
FIG. 11 is a diagram illustrating an example of a test facility table.
FIG. 12 is a diagram illustrating an example of a flow of the processing in a combining step.

The controller 10 of the integrated data management device A may refer to the test facility table 24, which is illustrated in FIG. 11 and stored in the integrated database 302, in response to the input of the test facility name via the GUI 130, and display a list of the test facility names capable of test request on the display unit of the terminal device B13 of the medical facility B1. The doctor-in-charge H1*a* can select a facility name for test request from the list.

FIG. 11 is a diagram illustrating an example of the test facility table 24 stored in the integrated database 302. In the test facility table 24, test facility IDs and the test facility names corresponding to the test facility IDs are stored in association with each other.

Back to FIG. 7, the "Facility for Interpreting Test Result" or "Facility for Expert Meeting" inputted in the region R2 for accepting the input of test request information is the name of the facility where to hold the expert meeting for interpreting the test results of a gene panel test. Note that the medical facility B1 as the test requester may hold an expert meeting by itself, or may apply to participate in an expert meeting which will be held in another medical facility B2.

The "ID of Facility for Interpreting Test Result" inputted in the region R2 for accepting the input of test request information is identification information corresponding to the name of the test facility for interpreting the test results. The controller 10 of the integrated data management device A may refer to the medical facility table 21 stored in the integrated database 302, and automatically display the facility ID corresponding to the facility name for interpreting the inputted test results in the facility ID field.

When there is no facility ID corresponding to the facility name inputted as the facility for interpreting the test results, a facility ID generated by the controller 10 may be stored in the medical facility table 21 in association with the facility name. Alternatively, the controller 10 may notify the administrator of the integrated data management device A that there is no facility ID corresponding to the name of the facility for interpreting the test results.

In addition, the configuration may be such that, for all patients P1 whose test using the information management system 100, the controller 10 of the information management system 100 automatically gives each patient an individual patient ID and sample ID, and gives each test request a test request ID, which is individual test request identification information. Note that, instead of automatically giving the patient ID and the test request ID, the controller 10 of the integrated data management device A may allow the doctor-in-charge H1*a* to input the test request information. For example, the doctor-in-charge H1*a* may be allowed to input the patient ID, the sample ID, and the test request ID given according to the rules determined in advance at the medical facility B1.

Modified Example of GUI for Inputting Test Request Information

FIG. 13 is a diagram illustrating an example of the GUI 130*a* including entry fields or sections R22 and R23 for inputting the disease name and disease ID of the patient P1. As above, instead of the GUI 130 for inputting the test request information illustrated in FIG. 7, an field R22 for inputting the disease name of the patient P1 and an field R23 for inputting the disease ID may be provided in the region R2, and the GUI 130*a* that allows the doctor-in-charge H1*a* to input the disease name and disease ID of the patient P1 may be displayed on the display unit of the terminal device B13 installed in the medical facility B1.

<Step Ib>

Back to FIG. 4, step Ib is a step in which the integrated data management device A notifies the terminal device B13 installed in the medical facility B1 that the test request has been accepted.

In step Ib, the controller 10 of the integrated data management device A transmits the patient ID, the test request ID, and the like to the terminal device B13. Note that when the patient ID is not inputted in step Ia, the integrated data management device A may create a patient ID and notify the terminal device B13 of the patient ID.

<Step Ic>

Step Ic is a step in which the integrated data management device A notifies the test information management device C11 of the test facility C1 that the test request has been accepted. In step Ic, the controller 10 of the integrated data management device A transmits information, such as the patient ID, the test request ID, the test request date, the gene panel name, the gene panel ID, and the disease ID of the patient P1 to the test information management device C11.

<Step Id>

Step Id is a step in which the integrated data management device A transmits a sample transport request to the collection/delivery management device E11 of the transportation establishment E1.

In step Id, the controller 10 of the integrated data management device A transmits the patient ID, the test request ID, the test facility for performing the test, the date for performing the test, and the like to the terminal device E12 of the transportation establishment E1.

<Step Ie>

Step Ie is a step in which the integrated data management device A accepts clinical information on the patient P1 corresponding to the test request from the terminal device B13 installed in the medical facility B1.

In step Id, the doctor-in-charge H1*a* uses the terminal device B13 to read the clinical information on the patient from the electronic medical record management device B11, and transmits the clinical information to the integrated data management device A together with the patient ID, the test request ID, and the like.

Note that the configuration may be such that, instead of the doctor-in-charge H1*a* transmitting the clinical information on the patient P1, the controller 10 of the integrated data management device A automatically acquires the clinical information on the patient P1 from the electronic medical record management device B11.

<Step IIa>

Step IIa is a step of instructing, in the medical facility B1, the preparation of the blood sample of the patient P1 from the terminal device B13 used by the doctor-in-charge H1*a* to another terminal device B13 used by a nurse or the like in the blood collection room in the medical facility B1. The instruction transmitted by the terminal device B13 used by the doctor-in-charge H1*a* includes the patient ID and the test request ID.

When the preparation of the blood sample in this step is completed, the nurse or the like in the blood collection room transmits information, such as the date and time of the completion of blood collection, from the terminal device B13 in the blood collection room to the electronic medical record management device B11, and updates the electronic medical record of the patient P1.

<Step IIb>

Step IIb is a step of instructing, in the medical facility B1, the preparation of the pathological tissue sample of the patient P1 from the terminal device B13 used by the doctor-in-charge H1*a* to another terminal device B13 of the pathology department in the medical facility B1. The instruction transmitted by the terminal device B13 used by the doctor-in-charge H1*a* includes the patient ID and the test request ID.

When the preparation of the pathological tissue sample in this step is completed, the pathologist H1*b* transmits information, such as the date and time of the completion of pathological tissue sample preparation, from the terminal device B13 of the pathology department to the electronic medical record management device B11, and updates the electronic medical record of the patient P1.

<Step IIc>

Step IIc is a step in which the integrated data management device A receives a notification that the preparations of the blood sample and the preparation of the pathological tissue sample are completed together with the patient ID, the test request ID, and the like.

In step IIc, the controller 10 of the integrated data management device A accepts a notification that the preparation of the sample of the patient P1 is completed from the terminal devices B13 used by the nurse in the blood collection room and the pathologist H1*b* in the pathology department. Not limited to this, the electronic medical record management device B11 may notify the integrated data management device A that the preparation of blood and pathological tissue samples is completed.

Note that the configuration may be such that the integrated data management device A periodically monitors the electronic medical record management device B11, and detects an update of information on the preparation status of the blood sample and the pathological tissue sample in the electronic medical record management device B11 of the patient P1. In addition, the configuration may be such that, even when the sample preparation is not completed, the integrated data management device A is notified of information indicating the sample preparation status. For example, when the sample preparation is not completed, the terminal device B13 or the electronic medical record management device B11 used by the nurse in the blood collection room and the pathologist H1*b* in the pathology department transmits information "Preparing Sample" to the integrated data management device A.

<Step IId>

Step IId is a step in which the integrated data management device A receives a pathological image and the like of the patient P1 together with the patient ID, the test request ID, and the like from the terminal device B13 used by the pathologist H1*b*.

In this step, the controller 10 of the integrated data management device A acquires information, such as a pathological image obtained by capturing the pathological tissue sample of the patient P1, the date of collecting the pathological tissue sample, the collected site, and pathologist opinions, from the pathological image management device B12.

Note that the pathologist H1*b* may be allowed to transmit information, such as a pathological image of the patient P1, to the integrated data management device A. In this case, the pathologist H1*b* uses the terminal device B13 to read the pathological image and the like of the patient P1 from the pathological image management device B12 via the in-medical-facility LAN, and transmits the information to the integrated data management device A together with the patient ID and the test request ID.

<Step IIe>

Step IIe is a step in which the integrated data management device A requests the transporter of the transportation establishment E1 to transport the pathological tissue sample and the blood sample. The step provides a notification from the integrated data management device A to the collection/delivery management device E11 of the transportation establishment E1 that the preparation of the blood sample and pathological tissue sample in the medical facility B1 is completed and that transportation from the medical facility B1 to the test facility C1 is possible, together with the patient ID and the test request ID.

<Steps IIf and IIg>

Steps IIf and IIg are steps in which the blood sample and the pathological tissue sample are passed over from the blood collection room and the pathology department of the medical facility B1 to the transporter of the transportation establishment E1.

RFID tags are attached to the sample container for storing the blood sample and the pathological tissue sample, and a package of the sample container. The RFID tags store information indicating the medical facility B1 as sample sender, information indicating the test facility C1 as the sample delivery destination, the patient ID of the patient P1 subjected to sample collection, the test request ID of the gene panel test to be performed, and the like. Alternatively, as an alternative to RFID, a sticker or a label may be provided, on which a bar code is printed to allow reading of information indicating the medical facility B1, information indicating the test facility C1, patient ID, test request ID, and the like.

<Step IIh>

In step IIh, the terminal device E21 possessed by the transporter of the transportation establishment E1 reads information indicating the medical facility B1, information indicating the test facility C1, patient ID, test request ID, and the like from the RFID tag or barcode on the package of the blood sample and the pathological tissue sample received from the medical facility B1. Then, the terminal device E12 of the transportation establishment E1 compares the read information with the information notified in advance in step Id.

For example, the transporter of the transportation establishment E1 receives from the medical facility B1 the blood sample and the pathological tissue sample for which the information stored in the RFID tag matches the information notified in step Id. Thereafter, the transporter inputs the completion of the reception to the own terminal device E12, and the terminal device E12 of the transportation establishment E1 transmits a reception completion notification to the collection/delivery management device E11.

<Step IIi>

Step IIi is a step in which the integrated data management device A receives a notification from the collection/delivery management device E11 that the sample reception is completed by the transportation establishment E1 and the transport to the test facility C1 has been started, together with the patient ID, the test request ID, and the like.

<Step IIj>

Step IIj is a step in which the transporter of the transportation establishment E1 transports the sample received from the medical facility B1 to the test facility C1.

The test facility C1 that has received the sample from the transporter confirms that the information stored in the RFID tag of the blood sample and the pathological tissue sample matches the information notified in step III. After confirming the receipt of the correct sample, the collection/delivery management device E11 is notified from the terminal device E12 possessed by the transporter of the transportation establishment E1 that the sample transport is completed.

<Step IIk>

Step IIk is a step in which the integrated data management device A receives a notification from the collection/delivery management device E11 that the sample transport is completed, together with the patient ID, the test request ID, and the like.

The controller 10 of the integrated data management device A may acquire, from the collection/delivery management device E11, transport log data including time taken to transport the sample, temperature management information during storage and transport of the sample, and the like. In this case, the transporter of the transportation establishment E1 transmits the transport log data collected in the transport of the sample from the terminal device E12 possessed by the transporter to the collection/delivery management device E11, and the transport log data is stored in advance. Note that, since the transport log data indicates the state of the sample to be subjected to the gene panel test and relates to the reliability of the test results, the transport log information can be referred to at the expert meeting.

<Step IIIa>

Step IIIa is a step of performing a gene panel test using a blood sample and a pathological tissue sample in the test facility C1.

The gene panel test includes, for example, a pretreatment step including DNA extraction from a sample and the like, a sequencing step of reading a base sequence by a next-generation sequencer, and a mutation extraction step in a pathological tissue. In addition, the test information management device C11 of the test facility C1 may give an annotation to the extracted mutation based on information acquired from the mutation information management device F11, the medicament information management device F21, and the academic paper information management device F31. Thereby, the test results of the requested gene panel test are obtained.

In step IIIa, the test information management device C11 of the test facility C1 notifies the integrated data management device A of the test progress information indicating to which step the gene panel test is completed, together with the patient ID, the test request ID, and the like.

<Step IVa>

Step IVa is a step in which the integrated data management device A receives the results of the test performed at the test facility C1 together with the patient ID, the test request ID, and the like from the test information management device C11 of the test facility C1.

Note that the clinical laboratory technician H3 may be allowed to transmit the test results to the integrated data management device A. In this case, the clinical laboratory technician H3 uses the terminal device C14 of the test facility C1 to read the test results from the test information management device C11 via the in-test-facility LAN, and transmits the test results to the integrated data management device A together with the patient ID and the test request ID.

The test result of the gene panel test may be put together or created as a test result report including related information, such as mutation information, medicament information, and academic paper information.

<Step Va>

Step Va is a step in which the integrated data management device A associates the test request information acquired in step Ia, the clinical information on the patient P1 acquired in step Ie and step IId, and the test results acquired in step Iva, and stores them in the master table 25 of the integrated data management device A.

Hereinafter, description is provided with reference to FIG. 12 for the flow of the processing in the integration step of integrating data acquired in steps Ia, Ie, IId, and Va. FIG. 12 is a diagram illustrating an example of the processing flow of the integration step performed by the controller 10 of the integrated data management device A.

In step Ia described above, the integrated data management device A receives the test request information from the terminal device B13 of the medical facility B1 (see step S13, FIG. 5). Subsequently, in step Ie described above, the clinical information on the patient P1 related to the test request is received from the terminal device B13 of the medical facility B1 (step S21). In addition, in step IId described above, the test results for the test request are received from the terminal device C14 of the test facility C1 (step S22).

Then, the controller 10 of the integrated data management device A stores the received clinical information on the patient P1 in the master table 25 of the integrated database 302 in association with the test request ID. In addition, the controller 10 of the integrated data management device A stores the received test results of the patient P1 in the master table 25 of the integrated database 302 in association with the test request ID. Thereby, the clinical information on the patient P1 and the test results of the patient P1 are associated with each other through the test request ID and stored in the master table 25 (step S23).

In an embodiment, although an example has been shown in which the controller 10 of the integrated data management device A acquires the clinical information on the patient P1 from the medical facility B1 at the time of requesting a test, the timing of acquiring clinical information and test request information is not limited thereto. The configuration may be such that the doctor-in-charge H1*a* of the medical facility B1 transmits the test request information and the clinical information together to the integrated data management device A at the time of test request, or the integrated data management device A receives clinical information from the medical facility B1 after the test is performed based on the test request information and before the expert meeting is held.

[Master Table 25]

FIG. 14 is a diagram illustrating an example of the master table 25 stored in the integrated database 302. As illustrated in FIG. 14, "Patient ID," "Sample ID," "Test Request ID," "Gene Panel ID," "Patient's Full Name," "Patient's Gender," "Date of Birth of Patient," "Consent of Patient," "Test Request Date," "User ID of Medical Specialist," "Full Name of Medical Specialist," "Group ID," "Test Progress Information," "Clinical Information," "Test Result," "Facility for Expert Meeting," and "Date and Time of Expert Meeting" are stored in the master table 25.

The "Patient ID," "Patient's Full Name," "Patient's Gender," "Date of Birth of Patient," "Consent of Patient," "Test Request Date," "User ID of Medical Specialist," "Full Name of Medical Specialist," and "Facility for Expert Meeting" are information inputted by the doctor-in-charge H1*a* using the GUI 130 illustrated in FIG. 7. Note that the "Full Name of Medical Specialist" is the full name inputted in the "Doctor-in-Charge of Patient" field of the region R2 of the GUI 130. In addition, the "User ID of Medical Specialist" is the user ID of the medical specialist inputted in the "User ID of Doctor-in-Charge" field in the region R2 of the GUI 130.

The information on the "Consent of Patient" in the region R2 of the GUI 130 includes, but is not limited to, consent to the test, providing of the anonymized test results to a third party institution, and a combination thereof. The information on the "Consent of Patient" in the region R2 of the GUI 130 may be displayed so as to allow selection by a pull-down menu or a radio button, or may be displayed so as to allow selection of an arbitrary combination from the list.

The master table 25 stores the content selected in the "Consent of Patient" of the region R2 of the GUI 130 as information on the "Consent of Patient." In addition, the master table 25 may store a link to the scan data of the patient's consent form as information on the "Consent of Patient."

The "Test Request ID" is identification information generated individually for each test request by the controller 10 of the integrated data management device A in response to receiving the test request information from the terminal device B13. Note that the "Test Request ID" may be issued individually by the numbering system owned by the facility that has accepted the test request, or may be arbitrarily issued by the staff of the facility that has received the test request, and is not limited thereto.

The "Sample ID" is sample identification information given to each sample prepared in the medical facility B1. In step IIc of FIG. 4, the controller 10 of the integrated data management device A receives from the terminal device B13 of the medical facility B1 that has prepared the sample of the patient together with a notification that the preparation of the sample is completed. Note that, as the sample ID, an ID common to both the blood sample and the pathological tissue sample may be generated, or an individual ID may be generated for each of the blood sample and the pathological tissue sample. In addition, the sample ID may be issued by the test facility C1 that conducts the test. In that case, the clinical laboratory technician H3 who is a medical specialist in the test facility C1 may store the issued sample ID in association with the test request ID in the master table 25, which is illustrated in FIG. 14 and stored in the integrated database 302 of the integrated data management device A.

The "Gene Panel ID" is identification information given for each type of gene panel used for gene panel test. The controller 10 of the integrated data management device A refers to the gene panel table 22 illustrated in FIG. 9 and extracts gene panel identification information corresponding to the gene panel name inputted in the "Test Type" field of the region R2 of the GUI 130.

The "Group ID" is group identification information given to each group including medical specialists to participate in the expert meeting. First, the controller 10 of the integrated data management device A refers to the test facility table 24 illustrated in FIG. 11, and specifies the facility ID corresponding to the facility name inputted in the "Facility for Interpreting Test Result" field of the region R2 of the GUI 130. Subsequently, the controller 10 of the integrated data management device A refers to the group table 26 illustrated in FIG. 17, and specifies the group ID corresponding to the specified facility ID. Note that, regarding the "Group ID" in the master table 25 illustrated in FIG. 14, the group ID may be extracted by extracting the expert meeting date and time information stored in association with the test request ID and referring to the expert meeting schedule table 27 illustrated in FIG. 18.

The "Test Progress Information" is information on the progress status of the test, which is received by the controller 10 of the integrated data management device A from the test information management device C11 of the test facility C1 in step IIIa of FIG. 4.

The "Test Progress Information" may include information on the preparation status of the sample to be subjected to the test, the transport status of the sample, the completion status of each step of the test, and the like. Examples of the "Test Progress Information" that can be used include "Preparing Sample," "Transporting Sample," "Pretreatment Step: Not Completed," "Pretreatment Step: Completed," "Sequence Step: Not Completed," "Sequence Step: Completed," "Mutation Analysis Step: Not Completed," and "Mutation Analysis Step: Completed." The "Preparing Sample" indicates a stage where the test request by the medical specialist is completed, but the acquisition of the sample is yet to be completed. The "Transporting Sample" indicates a stage where the transportation establishment E1 has completed the reception of the sample from the medical facility B1, but has not yet completed the transportation to the test facility C1. The "Pretreatment Step: Not Completed" indicates a stage where the transportation establishment E1 has delivered the sample to the test facility C1, but has not yet completed the sample pretreatment step. The "Pretreatment Step: Not Completed," "Pretreatment Step: Completed," the "Sequence Step: Not Completed," the "Sequence Step:

Completed," the "Mutation Analysis Step: Not Completed," and the "Mutation Analysis Step: Completed" indicate stages before and after the pretreatment step, before and after the sequence step, and before and after the mutation analysis step of the test in the test facility C1, respectively.

The "Clinical Information" may include, for example, information included in the electronic medical records of the patient, pathological images at the pathology department, and the like. When accepting the test request via the GUI 130 illustrated in FIG. 7, the controller 10 of the integrated data management device A extracts the patient ID included in the test request. Based on the extracted patient ID, the controller 10 of the integrated data management device A acquires the clinical information on the patient from the electronic medical record management device B11 and the pathological image management device B12 of the medical facility B1, and sets an individual folder in the integrated database 302 and stores the information therein. Back to FIG. 14, the controller 10 of the integrated data management device A may store link information to the file data of the clinical information as "Clinical Information" in the master table 25 in association with the patient ID and the test request ID.

The "Test Result" is the test result of the gene panel test, which are received by the controller 10 of the integrated data management device A from the test information management device C11 of the test facility C1 in step Iva of FIG. 4. The test result of the gene panel test include, but are not limited to, a summary report, a sequence report, a QC report, and a test report. In addition, the summary report and the test report may include, but are not limited to, "Sample Type (such as, FFPE and fresh frozen sample)," "Timing (initial or recurrent) and Site (primary/metastasis) of Sample Collection," "Pathological Diagnosis Name," "Pathological Sample Number," "Ratio of Tumor Cells in Sample (%)," "Quantity and Quality of DNA," "Reception Date," "Report Date," "Method of Panel Test," "Type of Gene Mutation and Clinical Significance," "Type and Version of Reference Database of Annotation Information," and the like. The controller 10 of the integrated data management device A stores the test results of the patients' gene panel tests acquired from the test information management device C11 of the test facility C1 in the individual folders provided in the integrated database 302 of the integrated data management device A. The controller 10 of the integrated data management device A may store the link information to the file data of the test results stored in the folders in the master table 25 as the "Test results." Note that the clinical laboratory technician H3 may be allowed to transmit the "Test Result" from the terminal device C14 used by the clinical laboratory technician H3 of the test facility C1 to the integrated data management device A.

In addition, the "Test Result" may be transmitted together with the "Test Request ID" from the test facility C1 and received by the controller 10 of the integrated data management device A. In this case, the controller 10 of the integrated data management device A may refer to the master table 25 when receiving the "Test Result" and store the "Test Result" in association with the record corresponding to the received "Test Request ID"

Note that the test facility C1 may store information on the "Amount of Sample Remaining" in the master table 25 in association with one or both of the "Test Request ID" and the "Sample ID." In addition, the test facility C1 may store information on the "Location of Residual Sample" in the master table 25 in association with one or both of the "Test Request ID" and the "Sample ID." Note that, here, although an example has been shown in which the test facility C1 relates to the "Amount of Sample Remaining" and the "Location of Residual Sample," the doctor-in-charge H1*a* of the medical facility B1 who has received the return of the remaining sample may store in the master table 25, and the example is not limited thereto.

The "Date and Time of Expert Meeting" is, for example, information on the scheduled date of the newly registered expert meeting and the schedule of the already held expert meeting. For example, when registration, change, and deletion of the scheduled date and time are inputted on the terminal device used by the medical specialist who has the authority to decide the scheduled date for an expert meeting, the controller 10 stores the inputted scheduled date and time in the master table 25.

Note that the scheduled date and time of the expert meeting may be decided and registered by adjusting the schedule among the medical specialists making up the group. Alternatively, a medical specialist having the authority to set up an expert meeting may register any scheduled date and time.

In addition, the master table 25 may store information on the meeting requirements indicating whether or not participation of medical specialists necessary for the expert meeting is confirmed. For example, assume that the expert meeting is required to (1) include one or more doctor-in-charges of the target patient to be tested, (2) include two or more pathologists, (3) include two or more cancer pharmacotherapy specialists, (4) include one or more bioinformatics experts, (5) include one or more genetic counselors, (6) include one or more molecular genetics researchers, and (7) include one or more genetic medicine specialists.

In that case, the integrated database of the integrated data management device A may store the requirements (1) to (7) in association with the expert meeting schedule table 27 illustrated in FIG. 18. Specifically, for the schedule of each expert meeting, the information stored may be such that (1) necessary number of participating doctor-in-charges (role ID: R01): 1, and hereinafter similarly, (2) pathologist (role ID: R02): 2, (3) cancer pharmacotherapy specialist (role ID: R03): 2, (4) bioinformatics expert (role ID: R04): 1, (5) genetic counselor (role ID: R05): 1, and (6) molecular genetics researcher (role ID: R06): 1, (7) genetic medicine specialist (role ID: R07): 1. Note that these numerical values are an example, and are not limited to these.

When receiving approval for schedule adjustment from the medical specialists regarding a predetermined expert meeting, the controller 10 of the integrated data management device A refers to the user registration table 23, which is illustrated in FIG. 10 and stored in the integrated database, and extracts the role IDs stored in association with the medical specialists having given approval. Next, the controller 10 of the integrated data management device A refers to the expert meeting schedule table 27 illustrated in FIG. 18, and performs the following processing for the above described requirements (1) to (7) stored in association with the schedule of the expert meeting.

Specifically, for example, when the role ID of a medical specialist who has approved the schedule adjustment is R05, that is, a genetic counselor, the numerical value 1 stored in the (5) genetic counselor (role ID: R05) stored in the expert meeting schedule table 27 is subtracted from 1 to obtain 0. This confirms that sufficient number of genetic counselors is participating in the schedule of the expert meeting. The controller 10 of the integrated data management device A performs the same process for other medical specialists.

The controller 10 of the integrated data management device A confirms that all the numbers of (1) to (7) are 0. When all the numbers are 0, the controller 10 may store "Meeting Can Be Held" as "Information on Meeting Requirements" in the master table 25. When not all of the numbers are 0, "Additional Call Is Required" can be stored. Note that, when not all of the numbers are 0, the controller 10 may display an icon 170 illustrated in FIG. 33 on the GUI 160 in order to alert the user.

Figure 15:
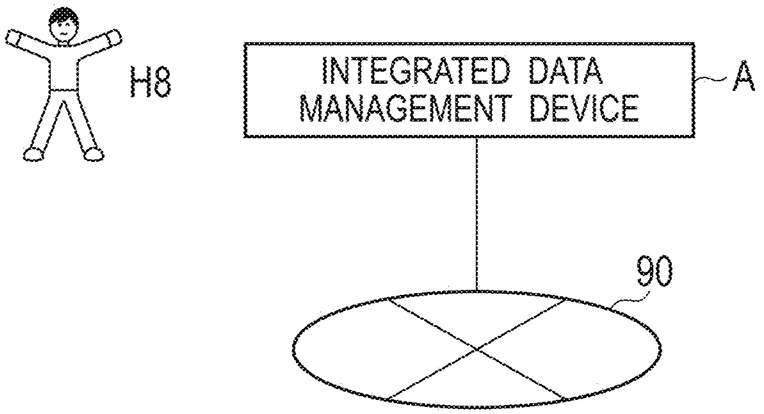
FIG. 15 is a diagram illustrating a configuration example in a case where there is an administrator who has management authority for an integrated data management device.

For example, the master table 25 may be managed such that it can be manually updated by an administrator H8 given the management authority for the integrated data management device A. FIG. 15 is a diagram illustrating a configuration example in the case where there is an administrator H8 who has the management authority for the integrated data management device A. Before the controller 10 of the integrated data management device A receives the test request information from the doctor-in-charge H1*a*, the administrator H8 may use the integrated data management device A to create the master table 25 based on the notified patient ID, patient full name, gender, date of birth of the patient, and the like. Note that, when the integrated data management device A is installed in the medical facility B1 (see FIG. 54), the medical specialist may be given the management authority for the integrated data management device A. For example, a medical specialist, such as the doctor-in-charge H1*a* of a patient, may input patient information into the master table 25.

[Association of Patient with Group to Participate in Expert Meeting]

Figure 16:
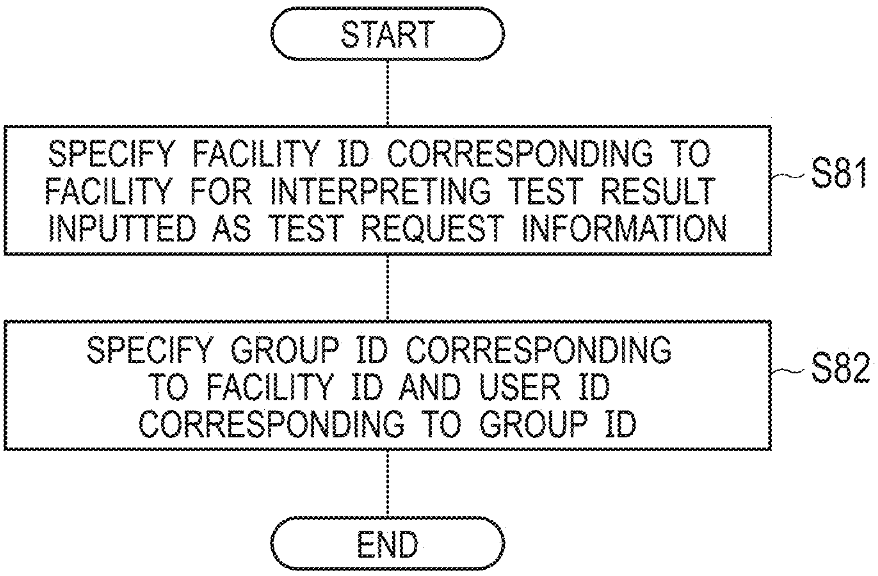
FIG. 16 is a flow diagram illustrating an overview of the processing in which a controller associates a patient with an expert who participates in an expert meeting.

The controller 10 may associate a patient with a group to participate in an expert meeting for determining the treatment policy for the patient. FIG. 16 is a flow diagram illustrating an overview of the processing in which the controller 10 associates a patient with an expert who participates in the expert meeting.

First, the controller 10 refers to the medical facility table 21 stored in the integrated database 302, and specifies the facility ID corresponding to the facility for interpreting the test results inputted as the test request information (step S81). Next, the controller 10 refers to the group table 26 stored in the integrated database 302, and specifies the group ID corresponding to the specified facility ID and the user ID corresponding to the group ID (step S82).

FIG. 17 is a diagram illustrating an example of the group table 26. As illustrated in FIG. 17, the group table 26 stores a set of a group ID, a facility ID, and multiple user IDs.

Here, taking the record M1 illustrated in FIG. 14 as an example, description is provided for the processing in which the controller 10 associates a patient with a group to participate in an expert meeting. The controller 10 refers to the medical facility table 21, and specifies the facility ID "F01" corresponding to the facility "xx Cancer Research Center" for interpreting the test results inputted as the test request information. Next, the controller 10 refers to the group table 26, and specifies the group ID "G01" or "G02" corresponding to the facility ID "F01." When the controller 10 specifies the group ID "G01," the user IDs "U01, U02, U03, U04, U05" corresponding to the group ID "G01" are specified. As described above, when there are multiple user IDs corresponding to the specified group ID, the controller 10 may associate the multiple user IDs with the patient ID included in the inputted test request information. Note that "specify" and "extract" have substantially the same meaning.

Note that, when there are multiple group IDs corresponding to the specified facility ID, the controller 10 may select one group at random from those groups. Alternatively, the controller 10 may refer to the expert meeting schedule table 27 stored in the integrated database 302, and preferentially select a group with a smaller number of registered expert meetings (that is, a schedule with more vacancy).

[Expert Meeting Schedule Table 27]

FIG. 18 is a diagram illustrating an example of the expert meeting schedule table 27. As illustrated in FIG. 18, the expert meeting schedule table 27 stores the group ID, the facility ID, the scheduled date and time of an expert meeting, and the allowable patient count. The allowable patient count is the upper limit of the number of patients for whom determination of treatment method is discussed at the expert meeting. The allowable patient count may be set depending on the length of time for which the expert meeting is held. For example, in the expert meeting schedule table 27 illustrated in FIG. 18, the allowable patient count is set to "4" when the expert meeting is scheduled for 4 hours (for example, "1:00 μm to 5:00 μm"), and set to "3" when scheduled for 3 hours (for example, "3:00 μm to 6:00 μm").

Taking the record M1 illustrated in FIG. 14 as an example, description is provided for a step in which the controller 10 specifies one of the multiple group IDs. The controller 10 refers to the medical facility table 21, and specifies the facility ID "F01" corresponding to the facility "xx Cancer Research Center" for interpreting the test results inputted as the test request information. Next, the controller 10 refers to the group table 26, and specifies group IDs "G01" and "G02" corresponding to the facility ID "F01." Next, the controller 10 refers to the expert meeting schedule table 27, compares the number of registrations in the expert meeting having the group ID "G01" with the number of registrations in the expert meeting having the group ID "G02," and specifies the group ID having the smaller number of registrations.

[Integrated ID]

The controller 10 may automatically generate an integrated ID (third identification information) each time the test request information is accepted. The controller 10 associates the clinical information on the patient and the test result of the gene panel test using the generated integrated ID for each test request information accepted. The integrated ID is identification information used for integrating information for test request information acquired each time by the controller 10. Note that the integrated ID may be issued by a numbering system different from the controller 10.

For example, the controller 10 may generate an integrated ID by a random combination of alphanumeric characters. Note that the controller 10 may generate a new integrated ID so as not to overlap with the previously generated integrated IDs, and the characters and the number of characters used to generate an integrated ID may be arbitrary.

The integrated ID may be associated with the patient ID and the test request ID. In this case, the controller 10 stores the generated integrated ID in the integrated ID table 28 stored in the integrated database 302. For example, FIG. 19 is a diagram illustrating an example of the integrated ID table 28. As illustrated in FIG. 19, in the integrated ID table 28, an integrated ID "oXy796K" is generated and stored for the data of the patient "PA01" and the test request ID "T01."

Alternatively, the integrated ID may be associated with the patient ID, the facility ID, and the test request ID. In this case, the controller 10 stores the generated integrated ID in the integrated ID table 28*a* stored in the integrated database 302. For example, FIG. 20 is a diagram illustrating an example of the integrated ID table 28*a*. As illustrated in FIG. 20, in the integrated ID table 28*a*, an integrated ID "MyiYAm2" is generated and stored for the data of the patient "PA04" and the test request ID "T04." The controller 10 stores the information accepted by the controller 10 for managing the sample transport status in the master table 25. It is required that the blood samples and pathological tissue samples be transported so as not to affect the success or failure of the test conducted at the test facility as well as the quality and reliability of the test results. This configuration makes it possible to confirm whether or not the blood sample and the pathological tissue sample transported from the medical facility B1 to the test facility C1 have been transported correctly under designated conditions.

(Management of Various Datasets Stored in Integrated Database 302)

The controller 10 may give a data ID and a data type ID to each of the patient information, the clinical information on the patient, and the data related to the test results accepted by the integrated data management device A from the terminal device B13, the electronic medical record management device B11, the pathological image management device B12, and the test information management device C11, and the like, and store the data ID and the data type ID in the integrated database 302. In addition, the controller 10 may give a data ID and a data type ID to each set of related information obtained by searching the servers of the information management facility group F, and store the data ID and the data type ID in the integrated database 302.

The data ID is an ID given to each dataset. On the other hand, the data type ID is an ID given to distinguish the data type. Examples of the data type ID include the following.

- "PA": ID given to the patient information accepted by the controller 10 from the terminal device B13, the electronic medical record management device B11, and the like.
- "IM": ID given to the pathological image data of the patient accepted by the controller 10 from the terminal device B13, the pathological image management device B12, and the like.
- "TEST": ID given to the data of the test results accepted by the controller 10 from the test information management device C11.
- "ANN": ID given to the annotation information acquired by the controller 10 from the mutation information management device F11, the medicament information management device F21, and the academic paper information management device F31

Note that the data type ID may be given so as to more finely classify multiple datasets included in the data type. For example, the controller 10 may give "ANN01" to the annotation information acquired from the mutation information management device F11, give "ANN02" to the annotation information acquired from the medicament information management device F21, and give "ANN03" to the annotation information acquired from the academic paper information management device F31. As described above, by subdividing the assignment of the data type ID, the controller 10 is allowed to perform more detailed access management.

<Patient Information Table 31>

FIG. 21 is a diagram illustrating an example of the patient information table 31 including the patient information accepted from the terminal device B13 by the controller 10 of the integrated data management device A in step Ia of FIG. 4. As illustrated in the patient information table 31 in FIG. 21, each of the patient information records stores a set of a patient's gender, age, disease ID, disease status (degree of development of the disease, and represented by stages I to IV in the case of cancer, for example), treatment history (regimen information), and the like, and the set of these datasets is associated with the data ID and the data type ID. Note that the patient information table 31 may include information on the patient's date of birth, disease name, reaction (side effects) to medicaments used in the past, and the like.

The controller 10 may allow the doctor-in-charge H1*a* to input the gender, age, disease status, treatment history, and the like of the patient, on the terminal device B13. Alternatively, the controller 10 may extract them from the clinical information on the patient accepted from the electronic medical record management device B11.

For example, the controller 10 may cause the terminal device B13 to display the GUI 130*a* having a field R22 for entering the patient's disease name and a field R23 for displaying the disease ID, and allow the doctor-in-charge H1*a* to input the patient's disease name (see FIG. 13). The configuration may be such that the controller 10 refers to the disease table 32 stored in the integrated database 302, and automatically displays the disease ID corresponding to the disease name inputted in the patient disease name field R22 in the disease ID field R23. FIG. 22 is a diagram illustrating an example of the disease table 32. As illustrated in FIG. 22, the disease table 32 stores a correspondence relationship between a disease ID and ar4 disease name corresponding to the disease ID. The controller 10 refers to the disease table 32, and searches for the disease ID corresponding to the inputted disease name. For example, according to the patient information table 31, the patient given the data ID "PA01" and the data type ID "PA" is a male of 52 years old suffering from lung cancer, and the patient given the data ID "PA03" and the data type ID "PA" is a female of 81 years old suffering from colon (large intestine) cancer.

<Pathological Image Table 33>

FIG. 23 is a diagram illustrating an example of the pathological image table 33 including the pathological image accepted by the controller 10 from the pathological image management device B12 in step IId of FIG. 4. As illustrated in the pathological image table 33 of FIG. 23, each of the pathological image records stores a set of sample collection date, collection site, link information to pathological image file data, pathologist opinions, and the like, and the set of these datasets is associated with the data ID and the data type ID. For example, according to the pathological image table 33, the pathological image given the data ID "IM01" and the data type ID "IM" relates to a pathological tissue sample collected on YYYY/MM/DD, and the pathological image data is managed as "Image 01." Note that a pathological image file may be stored in the integrated database 302 of the integrated data management device A, or one stored in the pathological image management device B12 may be referred to.

<Test Result Table 34>

FIG. 24 is a diagram illustrating an example of the test result table 34 including the test results accepted by the controller 10 from the test information management device C11 in step IVa of FIG. 4. As illustrated in the test result table 34 of FIG. 24, each of the test result records stores a set of link information to the test result report file data, mutation information, therapeutic agent information, gene panel ID, disease ID, sample quality information, DNA amount, and the like, and the set of these datasets is associated with the data ID and the data type ID.

As illustrated in FIG. 24, the test result table 34 includes the link to a report, mutation information, therapeutic agent information, disease ID, sample quality information, and DNA amount information.

The link to a report is link information to the test result report file data created by the clinical laboratory technician H3 and the like of the test facility C1.

The mutation information is information on the mutation detected by the gene panel test. For example, the data "EGFR T790M" in the test result table 34 illustrated in FIG. 24 indicates that, in the amino acid sequence of the protein EGFR, the 790th amino acid residue, which is threonine in the wild type, is mutated to methionine. Meanwhile, the data "BRAF V600E" indicates that, in the amino acid sequence of the protein BRAF, the 600th amino acid residue, which is valine in the wild type, is mutated to glutamic acid.

The therapeutic agent information is information on the therapeutic agent associated with the mutation detected by the gene panel test. For example, for example, "Medicament A" is shown for the data "EGFR T790M" and "Medicament B" is shown for the data "BRAF V600E" in the test result table 34 illustrated in FIG. 24.

The gene panel ID is identification information indicating the type of the gene panel used in the gene panel test. The controller 10 may search for and specify the gene panel ID by referring to, for example, the gene panel table 22 illustrated in FIG. 9.

The disease ID is identification information corresponding to the disease name for each patient. For example, the data "LUNG2 illustrated in FIG. 24 indicates that the patient's disease is lung cancer, and the data "COLON" indicates that the patient's disease is large intestine (colon) cancer (see FIG. 22).

The sample quality information is information on the quality of the patient sample delivered from the medical facility B1 to the test facility C1. The sample quality information may be, for example, "Excellent," "Good," and "Fair," and the like. Here, "Excellent" and "Good" indicate that a sufficient amount of DNA can be extracted from the pathological tissue of the patient in the pretreatment step of a gene panel test, and "Fair" indicates that the degradation of DNA is confirmed to be in progress, but there is no problem in conducting a gene panel test. Note that the sample state information "Failing" may be given in the case where the degradation of the DNA has progressed considerably, or the case where a sufficient amount of DNA for conducting a gene panel test cannot be extracted.

The DNA amount is information on the amount of DNA extracted from the pathological tissue of the patient in the pretreatment step of the gene panel test. The amount of DNA may be, for example, the weight (ng) of DNA extracted per 1 mg of pathological tissue.

<Annotation Information Table 35>

FIG. 25 is a diagram illustrating an example of the annotation information table 35 including the annotation information acquired by the controller 10 from the servers of the information management facility group F. As illustrated in the annotation information table 35 of FIG. 25, each of the annotation information records stores a set of annotation type, link information to the information source of related information, link information to data, text information, and the like, and the set of these datasets is associated with the data ID and the data type ID. For example, according to the annotation information table 35, the annotation information given the data ID "ANN01" and the data type ID "ANN" relates to mutation, the link information to the information source of related information is "https://xxx.yyy.com," and the data related to the related information is managed as "Data A01."

<Role Table 36>

When medical specialists belonging to medical facilities B1 and B2, the test facilities C1 and C2, and the external facilities D1 and D2 apply for the use of the information management system 100, the controller 10 generates user IDs for the medical specialists. Here, the controller 10 may generate role IDs together with the user IDs by referring to the role table 36 stored in the integrated database 302 for the medical specialists. Note that role IDs may be generated for employees of the transportation establishment group E included in the information management system 100. In addition, the generated role IDs may be stored in association with the user IDs of the user registration table 23 illustrated in FIG. 10.

FIG. 26 is a diagram illustrating an example of the role table 36. As illustrated in FIG. 26, the role table 36 stores a correspondence relationship between a role ID and a role name corresponding to the role ID. The controller 10 refers to the role table 36, and searches for the role ID corresponding to each medical specialist based on the information inputted when the medical specialists apply for the use of the information management system 100. Examples of the inputted information include the name of the belonging facility and the specialized field. For example, the controller 10 generates a role ID "R01" for the doctor-in-charge H1*a* of the patient P belonging to the medical facility B1, and generates a role ID "R08" for the clinical laboratory technician at the laboratory C1. For example, the controller 10 generates a role ID "R04" for the medical specialist who is a bioinformatics expert belonging to the external facility D1. Meanwhile, in the information management system 100, the controller 10 generates a role ID "R09" for the employee of the transportation establishment group E in charge of sample transport.

<Access Authority Management Table 37>

For example, the controller 10 may restrict data that can be viewed and used by the medical specialists and the employees of the transportation establishment E1 by referring to the access authority management table 37 stored in the integrated database 302.

FIG. 27 is a diagram illustrating an example of the access authority management table 37. As illustrated in FIG. 27, the access authority management table 37 stores a correspondence relationship between a role ID and a data type ID of data permitted to be accessed by a person corresponding to the role ID. The controller 10 refers to the access authority management table 37, and restricts the data type ID of data permitted to be accessed in response to an access request from the terminal devices B13, B23, C14, C24, D11, D21, E12, and the like.

[Access Restriction for Employees at Transportation Establishment E]

In step IIe of FIG. 4, after the sample reception request is notified from the controller 10 to the collection/delivery management device E11, the integrated data management device A may be accessible from the terminal device E12 used by the employees, for example. Note that, since the employees are not medical specialists, it is desirable that the employees be permitted only to use some of the functions of all information handled by the integrated data management device A. In light of the above, the controller 10 refers to the access authority management table 37, and restricts the data type ID of data permitted to be accessed by the employees based on the fact that the role ID of the employee who has transmitted an access request on the terminal device E12 is R07.

For example, when an employee logs in to the integrated data management device A, the terminal device E12 displays a screen 140 as illustrated in FIG. 28. FIG. 28 is a diagram illustrating an example of a screen displayed on the terminal device E12 of the transportation establishment. For example, the terminal device E12 displays a list of test requests accepted by the integrated data management device A. The employee can confirm the date on which the integrated data management device A accepted the screen test request, the test request ID, the sample preparation status, the test request source (for example, the name of the medical facility), and the test facility for performing the test (for example, the name of the test facility).

Note that the configuration may be such that the sample preparation status can be updated on the terminal device E12 by accepting an operation of selecting (for example, an operation of clicking) information displayed in the "Sample Preparation Status" on the screen 140. For example, the employee may be able to use the terminal device E12 to input information such as "Transporting Sample" and "Sample Transport Completed." In this case, a candidate list of "Sample Preparation Status" that can be inputted on the terminal device E12 may be displayed in the form of pull-down at the selected "Sample Preparation Status" position.

(Expert Meeting Schedule Management)

<Reservation of Expert Meeting>

When a medical specialist requests a test to be performed at the test facility C1, the information management system 100 can also make a reservation for an expert meeting for determining a treatment method for a patient based on the results of the test.

For example, as an alternative to the GUI 130 illustrated in FIG. 7, the controller 10 may display the GUI 150 illustrated in FIG. 29 that accepts the input of a reservation for an expert meeting. FIG. 29 is a diagram illustrating an example of the GUI 150 displayed on the terminal device B13 in order to accept the input of a reservation for an expert meeting.

The GUI 150 includes a region R1 that receives the input of information on a request source facility requesting a test, a region R2 that receives the input of test request information, a region R4 that accepts the input of a reservation for an expert meeting, and a request button R3 that accepts an instruction to transmit test request information from the terminal device B13 to the controller 10 of the integrated data management device A.

The region R4 may be provided with a list of scheduled dates and time or time periods for expert meetings in the facility (and facility ID) inputted in the region R2 as "Facility for Interpreting Test Result" and check boxes each for selecting the scheduled date and time period. For example, the controller 10 refers to the expert meeting schedule table 27 (see FIG. 18) stored in the integrated database 302, and causes the region R4 to display the scheduled date and time period of the expert meeting to be held at the facility "xx Cancer Research Center" inputted in the region R2 as "Facility for Interpreting Test Result."

For example, a medical specialist who wishes to reserve an expert meeting scheduled for 10:00 to 12:00 on Jan. 7, 2019 may click on the corresponding check box as illustrated. The regions R1 to R3 are substantially the same as those in the GUI 130 illustrated in FIG. 7.

For example, the controller 10 may display in the region R4 only the scheduled dates and time periods of the expert meetings scheduled to be held a predetermined period (such as one month) or more ahead of the test request date.

The controller 10 may refer to the expert meeting schedule table 27 as illustrated in FIG. 18, specify the group ID associated with the scheduled date and time period of the expert meeting selected by the medical specialist, and manage the schedule of the expert meeting. That is, the controller 10 refers to the group table 26 illustrated in FIG. 17, and extracts the user ID corresponding to the specified group ID.

Next, the controller 10 refers to the user registration table 23 as illustrated in FIG. 10, specifies the contact information of the medical specialist of each specified user ID, and transmits a notification of the expert meeting at the date and time to each medical specialist. This makes it possible for the integrated data management device A to accept the input of test request information by the doctor-in-charge H1*a* as well as the input of a reservation for an expert meeting that interprets the test results of the test performed at the test facility C1. Moreover, the integrated data management device A is allowed to transmit a notification that the expert meeting is scheduled to be held to each medical specialist to participate in the expert meeting who has accepted the reservation.

<Processing of Transmitting Notification of Reserved Expert Meeting to Each Medical Specialist>

Figure 31:
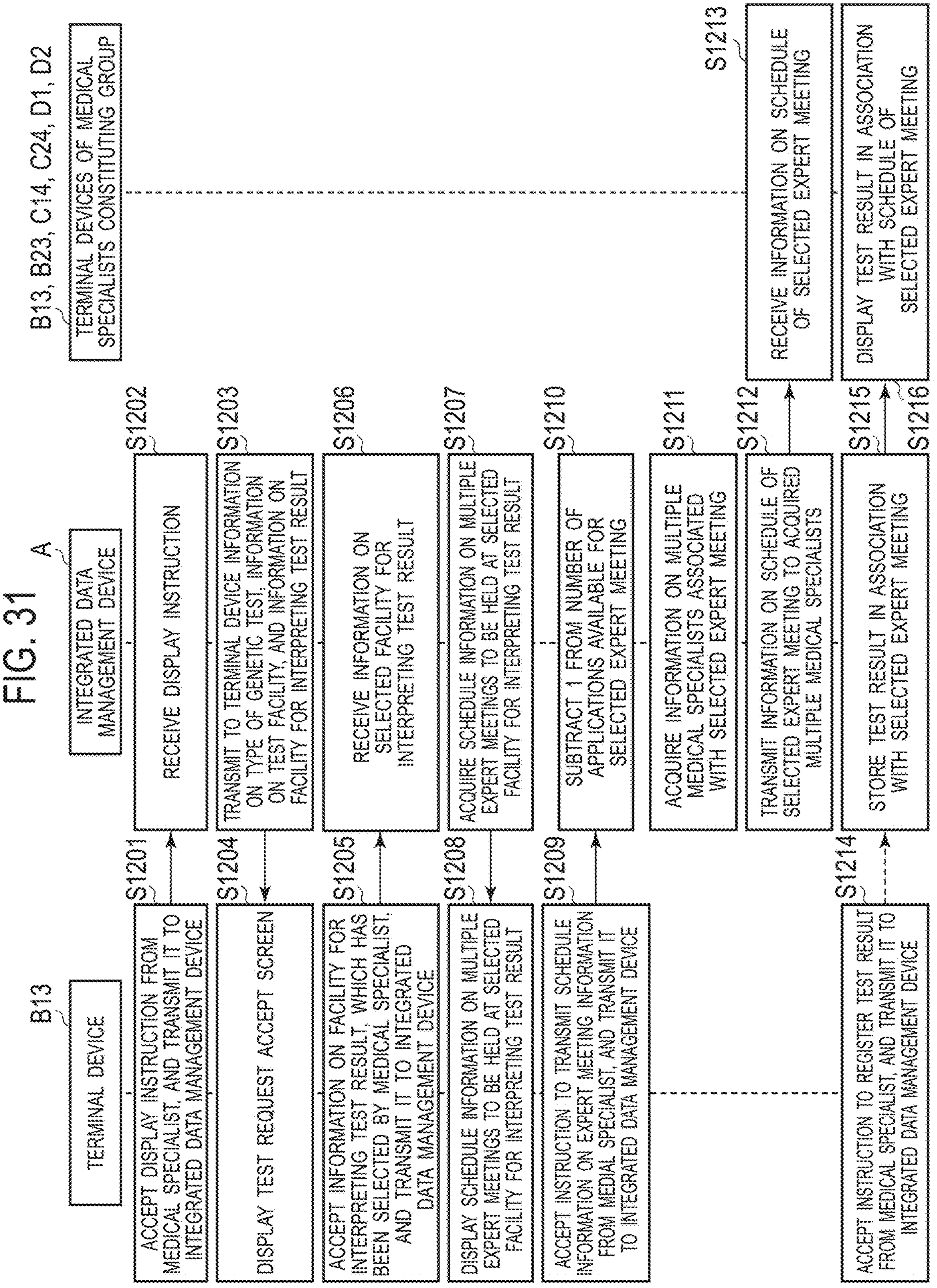
FIG. 31 is a diagram illustrating an example of a flow of the processing of transmitting a notification of a reserved expert meeting to each medical specialist.

Subsequently, with reference to FIG. 31, description is provided for an example of the flow of the processing of transmitting information on the schedule of an expert meeting reserved by medical specialists and the test results associated with the schedule to each of the medical specialists constituting or included in the group. FIG. 31 is a diagram illustrating an example of the flow of the processing of transmitting a reserved expert meeting notification to each medical specialist.

First, the terminal device B13 accepts a display instruction for a test request accept screen from a medical specialist, and transmits the display instruction to the integrated data management device A (step S1201). The test request accept screen may be, for example, the GUI 150 illustrated in FIG. 29.

The integrated data management device A receives the display instruction from the terminal device B13 (step S1202), acquires information on the type of a genetic test, information on the test facility, and information on the facility for interpreting the test results from the integrated database 302, and transmits the information to the terminal device B13 (step S1203).

The terminal device B13 displays a test request accept screen based on the information received from the integrated data management device A (step S1204).

Next, the terminal device B13 accepts information on the facility for interpreting the test results for the test request, which has been selected by the medical specialist on the test request accept screen, and transmits the information to the integrated data management device A (step S1205). The selection of information on the facility for interpreting the test results for the test request may be made from a list or a pull-down menu displayed based on the information acquired by the controller 10 of the data management device A in step S1203, but is not limited thereto.

The integrated data management device A receives information on the facility for interpreting the test results for the test request (step S1206), acquires schedule information on multiple expert meetings to be held at the facility from the expert meeting schedule table 27, and transmits the information to the terminal device B13 (step S1207).

The terminal device B13 receives schedule information on multiple expert meetings from the integrated data management device A, and displays the information in the region R4 of the GUI 150 (step S1208).

Next, the terminal device B13 accepts selection of one expert meeting from the medical specialist. In addition, the terminal device B13 accepts an instruction for notifying the selected expert meeting to multiple medical specialists to participate in the expert meeting, and transmits the instruction to the integrated data management device A (step S1209).

The integrated data management device A accepts schedule information on the one selected expert meeting. The integrated data management device A determines whether or not an application can be accepted for the selected expert meeting schedule. Specifically, the integrated data management device A acquires the allowable patient count of the selected expert meeting schedule from the expert meeting schedule table 27, and determines whether or not the number is 1 or more. When the allowable patient count is 1 or more, the application of the selected expert meeting schedule is accepted, and 1 is subtracted from the allowable patient count at that time (step S1210). The integrated data management device A acquires contact information on the multiple medical specialists associated with the selected expert meeting from the group table 26 (step S1211), and transmits a meeting notification including information on the schedule of the selected expert meeting to the acquired contact information used by the multiple medical specialists (step S1212).

Then, the terminal devices B13, B23, C14, C24, D11, and D21 used by the medical specialist receive the notification on the expert meeting (step S1213).

Next, the medical specialist registers the test results of the test request for the genetic information on the patient in the applied expert meeting on the screen of GUI 160 illustrated in FIG. 33 as an example. Specifically, the medical specialist refers to the GUI 160 displayed on the terminal device B13, and confirms the status of the own requested test in the "Sample Preparation and Test Status" field. When the test is completed, a hyperlink attached to the character string "Unregistered" displayed in the registration status of the test results is clicked to display the registration screen of the test results. The medical specialist registers the test results by dragging and dropping the test result report file onto the displayed registration screen of the test results. The terminal device B13 accepts a test result registration request from a medical specialist, and transmits the request to the integrated data management device A (step S1214). Note that the test result registration request may be received from the test information management device C11 of the test facility C1, and is not limited thereto. When the test result registration request is received from the test information management device C11 of the test facility C1, the controller 10 of the integrated data management device A stores the test result of the patient's gene panel test, acquired from the test information management device C11 of the test facility C1, in an individual folder provided in the memory 30 of the integrated data management device A. The controller 10 of the integrated data management device A stores link information to the folders in the master table 25, which is illustrated in FIG. 14 and stored in the integrated database 302 of the integrated data management device A.

Figure 45:
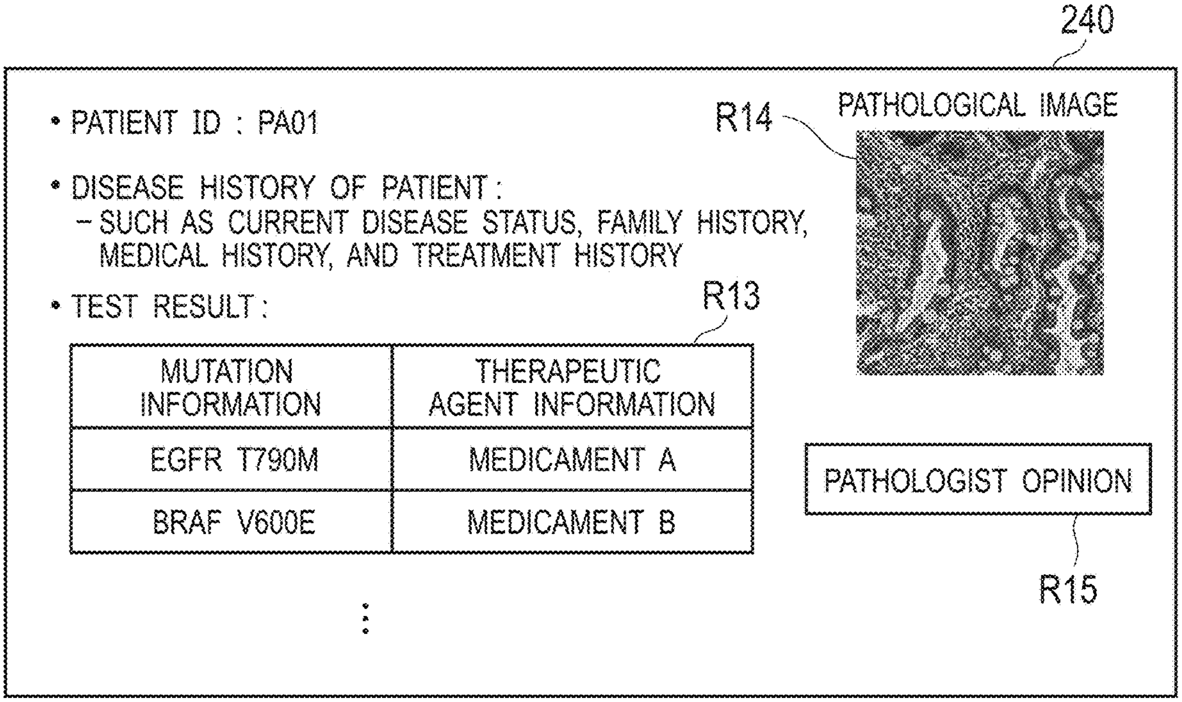
FIG. 45 is a diagram illustrating an example of a screen displayed by a controller on a terminal device in response to a reception of an information acquisition request.

The integrated data management device A stores the test results accepted from the terminal device B13 in the corresponding record of the master table 25. Thereby, the schedule of the expert meeting and the test results are stored in association with each other (step S1215). Then, when each medical specialist clicks on the "Display Related information" in the "Related information" field of the GUI 210, which is illustrated in FIG. 38 and displayed on the used terminal devices B13, B23, C14, C24, D11, and D21, the GUI 240, such as illustrated in FIG. 45, including the test results stored in association with the schedule of the expert meeting in step S1215 is displayed (step S1216).

Figure 32:
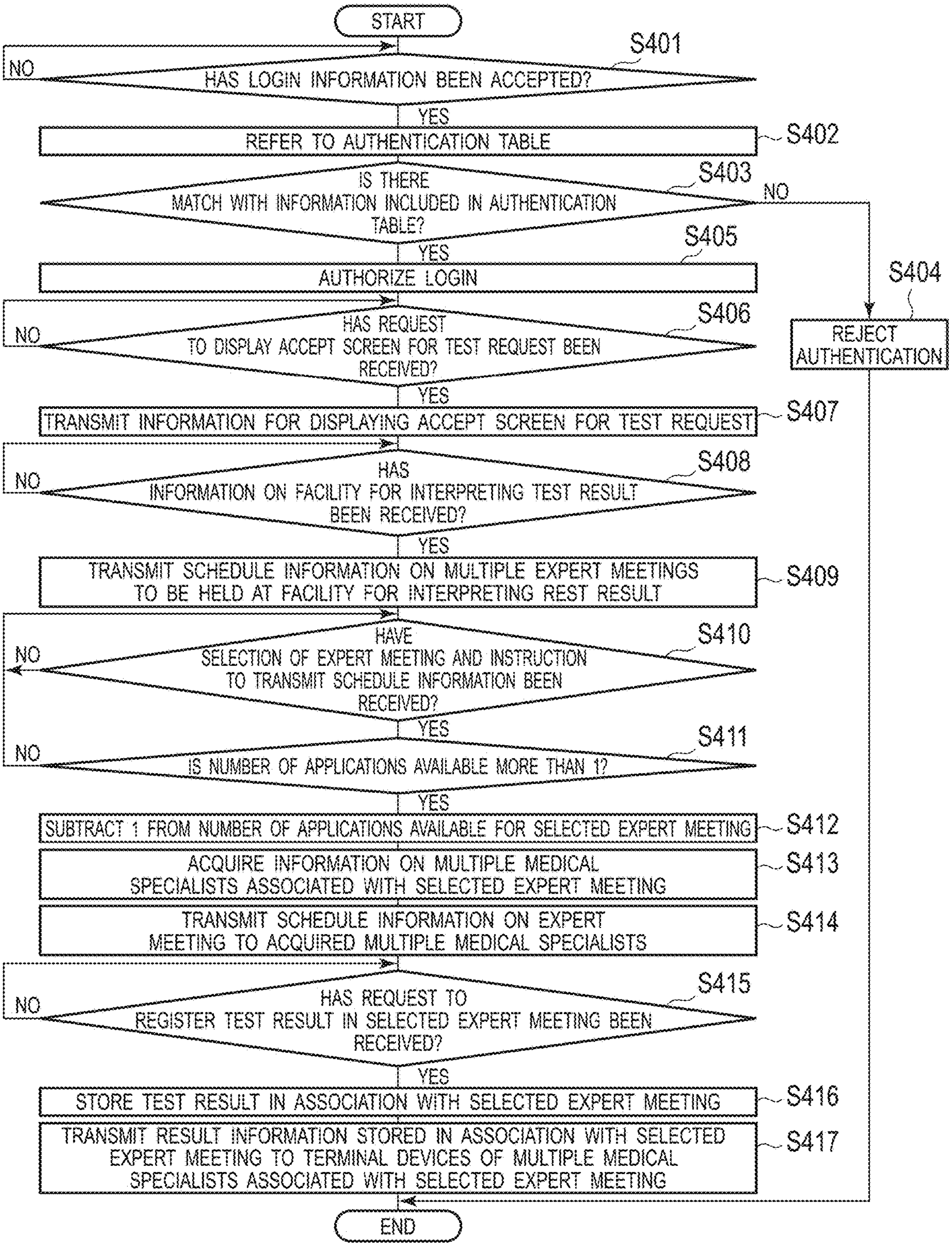
FIG. 32 is a diagram illustrating an example of a flow of the processing performed by a controller of an integrated data management device in order to transmit information on a schedule of an expert meeting to a terminal device of each medical specialist.

Next, with reference to FIG. 32, description is provided for an example of the flow of the processing performed by the controller 10 of the integrated data management device A in order to transmit the information on the schedule of the expert meeting and the test results associated with the schedule to the terminal devices B13, B23, C14, C24, D11, and D21 of the medical specialists.

The controller 10 of the integrated data management device A determines whether or not the login information inputted when the medical specialist makes an authentication request on the terminal device B13 has been accepted (step S401). When the login information is accepted (YES in step S401), the authentication table 38, which is illustrated in FIG. 6 and stored in the integrated database 302 of the integrated data management device A, is referred to (step S402). Here, the login information is described by taking the combination of a user ID and a login password as an example, but a medical specialist may be authenticated by fingerprint or face, and is not limited thereto.

Subsequently, the controller 10 determines whether or not the accepted login information matches the information included in the authentication table 38 (step S403). For example, when the login information includes a login password, the controller 10 determines whether or not the login password corresponding to the user ID included in the authentication table 38 matches the login password included in the accepted login information. In the case of mismatch (NO in step S403), the controller 10 rejects the login authentication (step S404). On the other hand, in the case of match (YES in step S403), the login is authenticated (step S405).

After authenticating or authorizing the login, the controller 10 determines whether or not a request to display the accept screen for the test request has been received (step S406). When receiving the display request (YES in step S406), the controller 10 transmits information for displaying on the terminal device B13 the accept screen for the test request illustrated in the GUI 150 of FIG. 29 (step S407). Note that the information, transmitted by the controller 10, for displaying a predetermined screen on the terminal device B13 includes, but is not limited to, HTML (Hyper Text Markup Language), XML (Extensible Markup Language), and JavaScript (registered trademark) data.

Next, the controller 10 determines whether or not the information on the facility for interpreting the test results has been received (step S408). When the information on the facility for interpreting the test results is received (YES in step S408), the schedule information on multiple expert meetings to be held at the facility for interpreting the test results is transmitted to the terminal device B13 (step S409).

Specifically, the controller 10 refers to the expert meeting schedule table 27, which is illustrated in FIG. 18 and stored in the integrated database 302 of the integrated data management device A, based on the received information on the facility for interpreting the test results. The controller 10 extracts the received schedule information on the multiple expert meetings to be held at the facility for interpreting the test results. Note that the controller 10 may refer to the allowable patient counts stored in association with the extracted expert meetings, and transmit the information to the terminal device B13 except for the expert meetings having an allowable patient count of 0.

Next, the controller 10 determines whether or not the selection of an expert meeting and a meeting notification instruction have been received (step S410). When the selection of an expert meeting and the meeting notification instruction have been received (YES in step S410), the controller 10 determines whether or not the selected expert meeting can accept an application (step S411). Specifically, the controller 10 refers to the expert meeting schedule table 27, which is illustrated in FIG. 18 and stored in the integrated database 302 of the integrated data management device A, and refers to the allowable patient count stored in association with the selected expert meeting. When the allowable patient count is 1 or more (YES in step S411), an application for the selected expert meeting is accepted. Here, the controller 10 decreases (decrements) by 1 the value of the allowable patient count stored in association with the selected expert meeting (step S412). In addition, when the allowable patient count stored in association with the selected expert meeting is 0 (NO in step S411), the controller 10 returns to step S410, and determines whether or not the selection of another expert meeting and a meeting notification instruction have been received.

In addition, after deciding whether or not the selected expert meeting can accept an application (step S411), the controller 10 may determine whether or not the approval of the application for the expert meeting has been received from the medical specialist having the authority to set up an expert meeting. Specifically, when the application for the selected expert meeting is made by a medical specialist having no authority to set an expert meeting, such as a doctor-in-charge H1*a* belonging to the medical facility B1, the medical specialist having the authority to set up an expert meeting, such as a medical specialist belonging to the medical facility B2, approves the application. The medical specialist belonging to the medical facility B2 approves the application for the expert meeting on the terminal device B23. The terminal device B23 transmits the approval information to the integrated data management device A. When receiving the approval information, the controller 10 of the integrated data management device A decreases (decrements) by 1 the value of the allowable patient count stored in association with the selected expert meeting (step S412). Note that the doctor-in-charge H1*a* belonging to the medical facility B1 may propose (apply) multiple expert meeting candidates to the medical specialists belonging to the medical facility B2, and the medical specialists belonging to the medical facility B2 may select one of the expert meeting candidates to approve the application for the expert meeting.

Next, the controller 10 acquires contact information for the multiple medical specialists associated with the selected expert meeting (step S413). That is, the controller 10 refers to the expert meeting schedule table 27, which is illustrated in FIG. 18 and stored in the integrated database 302 of the integrated data management device A, and extracts the group ID stored in association with the selected expert meeting. Next, the controller 10 refers to the group table 26, which is illustrated in FIG. 17 and stored in the integrated database 302 of the integrated data management device A, and extracts the user IDs of the users who constitute the group stored in association with the extracted group ID. Next, the controller 10 refers to the user registration table 23, which is illustrated in FIG. 10 and stored in the integrated database 302 of the integrated data management device A, and acquires contact information stored in association with the extracted user IDs. Note that, although an example has been shown here which refers the expert meeting schedule table 27 and the user registration table 23, the master table 25 and the user registration table 23 may be referred to, or another table combining the expert meeting schedule table 27 and the user registration table 23 may be created, but is not limited thereto.

Next, the controller 10 transmits the information on the schedule of the selected expert meeting to the contact information of the acquired multiple medical specialists (step S414).

Moreover, controller 10 determines whether or not a test result registration request for the selected expert meeting has been received (step S415). When the test result registration request is received (YES in step S415), the received test results and the selected expert meeting are stored in association with each other in the master table 25, which is illustrated in FIG. 14 and stored in the integrated database 302 of the integrated data management device A (step S416). Note that the test result registration request may be received from the test information management device C11 of the test facility C1, and is not limited thereto. When the test result registration request is received from the test information management device C11 of the test facility C1, the controller 10 of the integrated data management device A stores the test result of the patient's gene panel test acquired from the test information management device C11 of the test facility C1 in an individual folder provided in the memory 30 of the integrated data management device A. The controller 10 of the integrated data management device A stores link information to the folders in the master table 25, which is illustrated in FIG. 14 and stored in the integrated database 302 of the integrated data management device A.

In the selected expert meeting, when each medical specialist to attend the expert meeting displays the GUI 210 illustrated in FIG. 38 on the terminal devices B13, B23, C14, C24, D11, and D21, and clicks on the "Display Related information" in the "Related information" field, the controller 10 transmits result information including the test results associated with the expert meeting (step S417). The terminal devices B13, B23, C14, C24, D11, and D21 that have received the result information display the GUI 240 illustrated in FIG. 45.

Note that the controller 10 may be configured to detect that a medical specialist, such as the doctor-in-charge H1*a* registers patient information on the patient P, and to notify the detected patient information to multiple medical specialists. This makes it possible to appropriately notify the registration status of patient information referred to at the expert meeting to multiple medical specialists, and appropriately support discussion at the expert meeting.

As described above, in addition to the input of the test request information by the doctor-in-charge H1*a*, the integrated data management device A can accept the input of the reservation for an expert meeting for interpreting the test results of a test performed at the test facility C1. Moreover, the integrated data management device A can transmit a notification that the expert meeting is scheduled to be held to the terminal devices B13, B23, C14, C24, D11, and D21 of the medical specialists to attend the expert meeting who have has accepted the reservation.

<Display of Schedule of Expert Meeting>

For example, the controller 10 of the integrated data management device A may cause the terminal devices B13, B23, C14, C24, D11, and D21 used by the medical specialists to participate the expert meeting to display the test request information accepted by the controller 10 and information regarding the schedule of the expert meeting. FIG.

33 is an example of the GUI 160 that causes the terminal devices B13, B23, C14, C24, D11, and D21 used by the medical specialists to display a list of test requests and information on the schedules of expert meetings as a screen. The controller 10 causes the display units of the terminal devices B13, B23, C14, C24, D11, and D21 to display the GUI 160 as a test progress screen that simultaneously shows the test progress information and the schedule information.

The GUI 160 includes a region R5 for displaying a list of test requests and a region R6 for displaying the schedules of expert meetings.

For example, the region R5 displays "Request Date," "Patient ID," "Sample Preparation and Test Status," "Registration Status of Patient Information," and "Registration Status of Test Result." Note that the "Test Request ID" may be displayed in the region R5. The patient information and the test result information are both information that is referred to by multiple medical specialists at the expert meeting.

Display examples of the "Sample Preparation and Test Status" include "Preparing Sample," "Sample Preparation Completed," "Transporting Sample," "Sample Transport Completed," "Acquire Sample Again," "Test Canceled," "DNA Extraction Completed," "Pretreatment Completed," "Sequencing Completed," "Sequence Analysis Completed," and "Test Completed." The expected date and time of completion of test may be displayed.

Display examples of the "Registration Status of Patient Information" include "Unregistered," "Partially Registered," and "Registration Completed." Note that the "Partially Registered" is a situation in which, for example, a patient's electronic medical record has been registered, but a pathological image or the like is not registered.

Display examples of the "Registration Status of Test Result" include "Unregistered" and "Registration Completed."

In response to the registration of patient information, test results, and the like referred to by multiple medical specialists at an expert meeting from the medical facility B1 and the test facility C1 into the integrated data management device A, the registration status may be notified to the terminal devices B13, B23, C14, C24, D11, D21, and the like corresponding to the multiple medical specialists.

Meanwhile, for example, the region R6 displays "Facility for Expert Meeting," "Status," and "Meeting Date and Time."

The "Status" displays information indicating the setting status of the expert meeting. For example, "Already Set" is displayed in the "Status" when the schedule of the expert meeting is fixed and the notification of the schedule to the medical specialists to participate in the expert meeting is completed. In addition, when the schedule of the expert meeting is unfixed, or the notification to the medical specialists to participate in the expert meeting is not completed, "Unset" is displayed.

The "Meeting Date and Time" displays, for an expert meeting whose "Status" is "Already Set," the expert meeting to be held or the schedule having been held in the form of date and time. The "Meeting Date and Time" displays, for an expert meeting whose "Status" is "Unset," that the setting is yet to be completed. Whether the "Status" is "Already Set" or "Unset," it is possible to newly set an expert meeting and update the status of the expert meeting in response to a click on the display.

The controller 10 of the integrated data management device A accepts selection of information attributes, such as "Test Request ID," "Test Result," and "Date and Time of Expert Meeting," stored in the integrated database 302 via the GUI 160, reads information corresponding to the selected attribute from the integrated database 302, and outputs the information.

The controller 10 may acquire a record ID, which is record identification information for identifying each record of the attribute information to be outputted, for each record. In this case, the controller 10 outputs the record ID and the selected attribute information in association with each other.

The controller 10 may display an icon 170 for alerting the user on the GUI 160. For example, when there is a high possibility that the test will not be completed by the scheduled date and time of the expert meeting, or when the "Status" of the expert meeting is "Unset" even though the test is almost completed or the test is completed, the controller 10 displays the icon 170 on the GUI 160 when a delay in performing the test is expected in consideration of the sample preparation and test status. Note that the case where a delay in performing the test is expected in consideration of the sample preparation and test status is, for example, the case of "Test Canceled," "Acquire Sample Again," "Test Canceled," and the like.

Note that the icon 170 is not limited to "!" as long as it is an icon that can draw attention to medical specialists. In addition, instead of displaying the icon 170, the display of the expert meeting and the meeting date and time may be displayed in a different font and color from the others.

More specifically, the controller 10 of the integrated data management device A displays the icon 170 on the GUI 160 in the case where (1) the "Sample Preparation and Test Status" is the "Acquire Sample Again," (2) the "Sample Preparation and Test Status" is the "Test Canceled," (3) "Sample Preparation and Test Status" is not "Test Completed" and the date of the expert meeting is one week or less ahead, (4) the "Sample Preparation and Test Status" is the "Test Completed" and the "Status" of the expert meeting is "Unset," or (5) the "Sample Preparation and Test Status" has reached the "Sequence Reading Completed" and the "Status" of the expert meeting is "Unset."

Based on the information stored in the master table 25 of the integrated data management device A, the controller 10 can determines whether or not the above conditions (1) to (5) are satisfied, and can display the icon 170 on the GUI 160.

<Flow of Processing of Displaying GUI 160>

Figure 34:
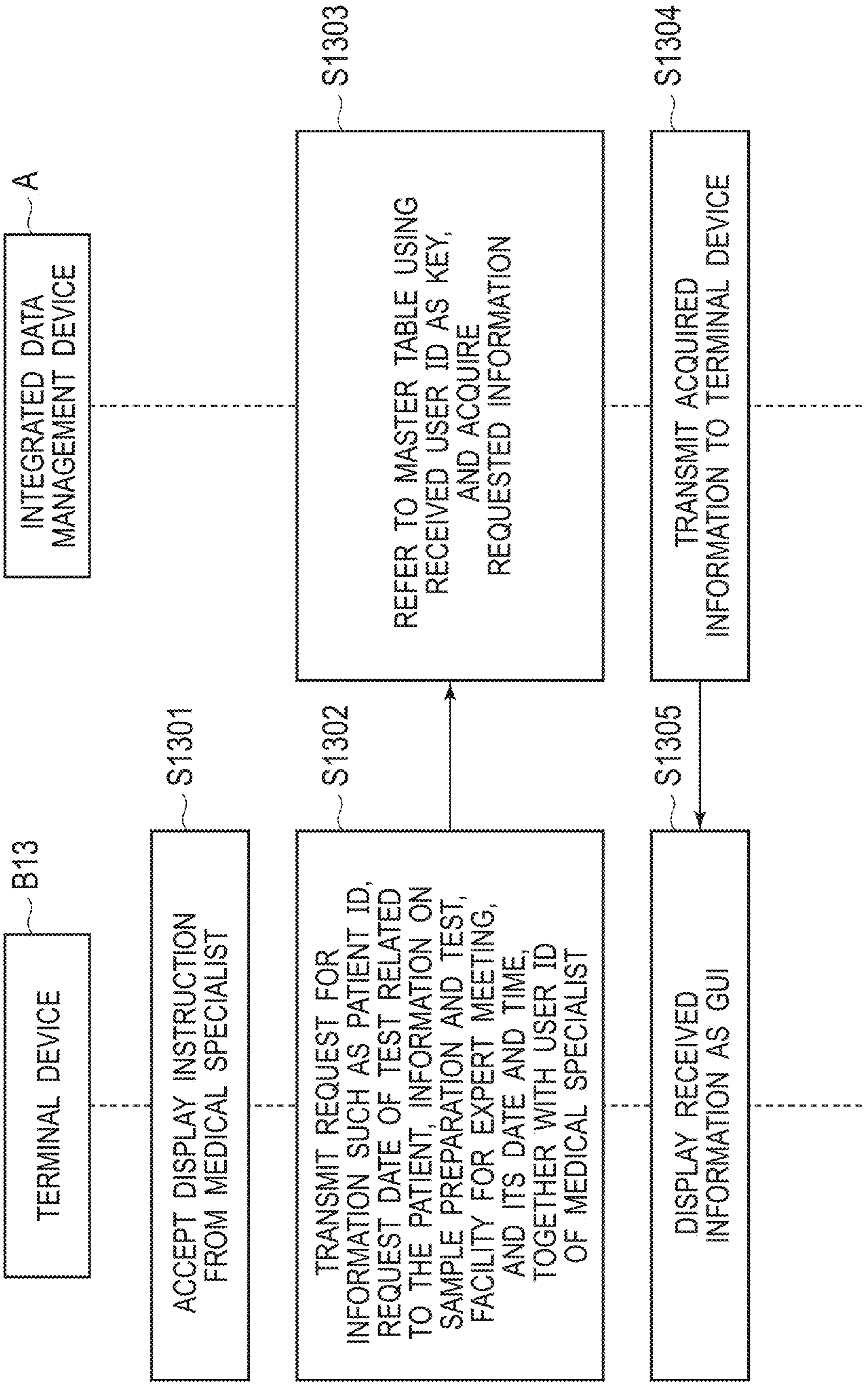
FIG. 34 is a diagram illustrating an example of a flow of the processing of causing a terminal device to display a list of test requests, related to a patient attended to by a medical specialist, and information on a schedule of an expert meeting.

Here, with reference to FIG. 34, description is provided for the flow of the processing of displaying the GUI 160 including information on a list of test requests and the schedules of expert meetings on the terminal device B13 used by the medical specialists at the medical facility B1. FIG. 34 is a diagram illustrating an example of the flow of the processing of causing the terminal device B13 to display a list of test requests related to the patients in charge by medical specialists and information on the schedules of expert meetings.

First, the terminal device B13 accepts an instruction to display the schedule of an expert meeting from a medical specialist belonging to the medical facility B1 (step S1301). Next, together with the user ID of the medical specialist, the terminal device B13 transmits to the integrated data management device A a request for information such as the patient ID of the patient taken care or attended to by the medical specialist, the test date of the test request related to the patient, information on sample preparation and test, the facility for the expert meeting, and its date and time (step S1302).

Next, the controller of the integrated data management device A refers to the master table 25 stored in the memory 30 using the received user ID as a key, and acquires the requested information (step S1303). The integrated data management device A transmits the acquired information to the terminal device B13 (step S1304).

Next, the terminal device B13 displays the information received from the integrated data management device A as the GUI 160 on the display unit of the terminal device B13 (step S1305).

With reference to FIG. 35, description is provided for the details of the processing performed by the integrated data management device A in order to display the GUI 160 on the terminal device B13 used by a medical specialist. FIG. 35 is a diagram illustrating an example of the flow of the processing performed by the controller 10 of the integrated data management device A in order to display information, formed by associating information on the progress of the test with information on the schedule of an expert meeting, on the terminal device B13 of a medical specialist.

The controller 10 of the integrated data management device A determines whether or not login information has been accepted from the terminal device B13 (step S501). When the login information has been accepted (YES in step S501), the authentication table 38 stored in the integrated database 302 of the integrated data management device A is referred to (step S502). Subsequently, it is determined whether or not the login password corresponding to the user ID included in the authentication table 38 matches the login password included in the accepted login information (step S503). In the case of mismatch (NO in step S503), the controller 10 rejects the login authentication (step S504). On the other hand, in the case of match (YES in step S503), the login is authenticated (step S505).

Next, the controller 10 determines whether or not a request to display information on the patient taken care by the authenticated medical specialist and information on the expert meeting has been received (step S506). When the display request is received (YES in step S506), information on the test associated with the user ID of the authenticated medical specialist and information on the expert meeting are extracted from the master table 25 (step S507).

Next, the controller 10 extracts test progress information associated with the extracted test information (step S508).

Next, the controller 10 associates information on the progress of the test with information on the expert meeting, and transmits them to the terminal device B13 (step S509).

<Registering Schedule of Expert Meeting>

When the input of the reservation for an expert meeting is accepted via the GUI 150, which is illustrated in FIG. 29 and displayed on the terminal device B13 of the medical facility B1 in order to accept the input of the reservation for the expert meeting, the controller 10 of the integrated data management device A registers the information inputted as the reservation for the expert meeting in the master table 25 of the patient related to the inputted test request information.

In addition, the controller 10 of the integrated data management device A extracts the information displayed in the "Date and Time of Expert Meeting" of the facility inputted as the facility for interpreting the test results from the expert meeting schedule table 27 (see FIG. 18) stored in the integrated database 302 of the integrated data management device A.

The controller 10 generates a list of scheduled dates and time periods of expert meetings based on the extracted information, and causes the terminal devices B13, B23, C14, C24, D11, D21, and the like used by medical specialists to display the GUI 160 illustrated in FIG. 33.

Note that, when the controller 10 of the integrated data management device A extracts the meeting date and time from the expert meeting schedule table 27 as a candidate schedule of the expert meeting to be held at the facility inputted as the "Facility for Interpreting Test Result," the extraction conditions may be changed according to the "Sample Preparation and Test Status."

Examples of the extraction conditions include the following conditions (1) to (5).

(1) When the "Sample Preparation and Test Status" is the "Test Completed," a two-week list of scheduled dates and time periods, when expert meetings are to be held on days following the current date and time, is displayed, for example.

(2) When the "Sample Preparation and Test Status" is "Acquire Sample Again," a two-week list of scheduled dates and time periods, when expert meetings are to be held after a predetermined number of days (for example, 40 days) from the current date and time, is displayed, for example.

(3) When the "Sample Preparation and Test Status" is any of the "Sample Preparation Completed," the "Transporting Sample," and the "Sample Transport Completed," a two-week list of scheduled dates and time periods, when expert meetings are to be held after a predetermined number of days (for example, 30 days) from the current date and time, is displayed, for example.

(4) When the "Sample Preparation and Test Status" is either the "DNA Extraction Completed" or the "Pretreatment Completed," a two-week list of scheduled dates and time periods, when expert meetings are to be held after a predetermined number of days (for example, 15 days) from the current date and time, is displayed, for example.

(5) When the "Sample Preparation and Test Status" is either the "Sequence Reading Completed" or the "Analysis Completed," a two-week list of scheduled dates and time periods, when expert meetings are to be held after a predetermined number of days (for example, 10 days) from the current date and time, is displayed, for example.

Note that the conditions for extracting candidate schedules of an expert meeting are not limited to this, and can be appropriately changed according to the operation of the medical facilities B1 and B2.

<Notification to Medical Specialists of Schedule of Expert Meetings>

The controller 10 of the integrated data management device A can notify medical specialists based not only on the "Sample Preparation and Test Status" but also on the "Registration Status of Patient Information" and the "Registration Status of Test Information."

For example, in response to the patient information and the test results being registered in the master table 25, the controller 10 transmits a notification on an expert meeting to medical specialists to participate in the expert meeting for interpreting the test results.

For example, when the condition for displaying the icon 170 is satisfied, the controller 10 transmits a notification that the schedule of the corresponding expert meeting may change to the medical specialists to participate in the expert meeting. This notification may be a notification that prompts the medical specialists to early set a date and time of an expert meeting, or a notification that prompts to reset the date and time of the expert meeting or to cancel the schedule of the expert meeting.

[GUI 180 for Accepting Input of Selection Information on Experts to Participate in Expert Meeting]

The controller 10 of the integrated data management device A may cause the terminal devices B13, B23, C14, C24, D11, and D21 to display the GUI 180 for accepting the input of selection information on experts to participate in the selected expert meeting in response to the expert meeting being selected from the list of the scheduled dates and time periods of expert meeting and to the reservation for the expert meeting being entered in the region R4 of the GUI 150 illustrated in FIG. 29.

Figure 36:
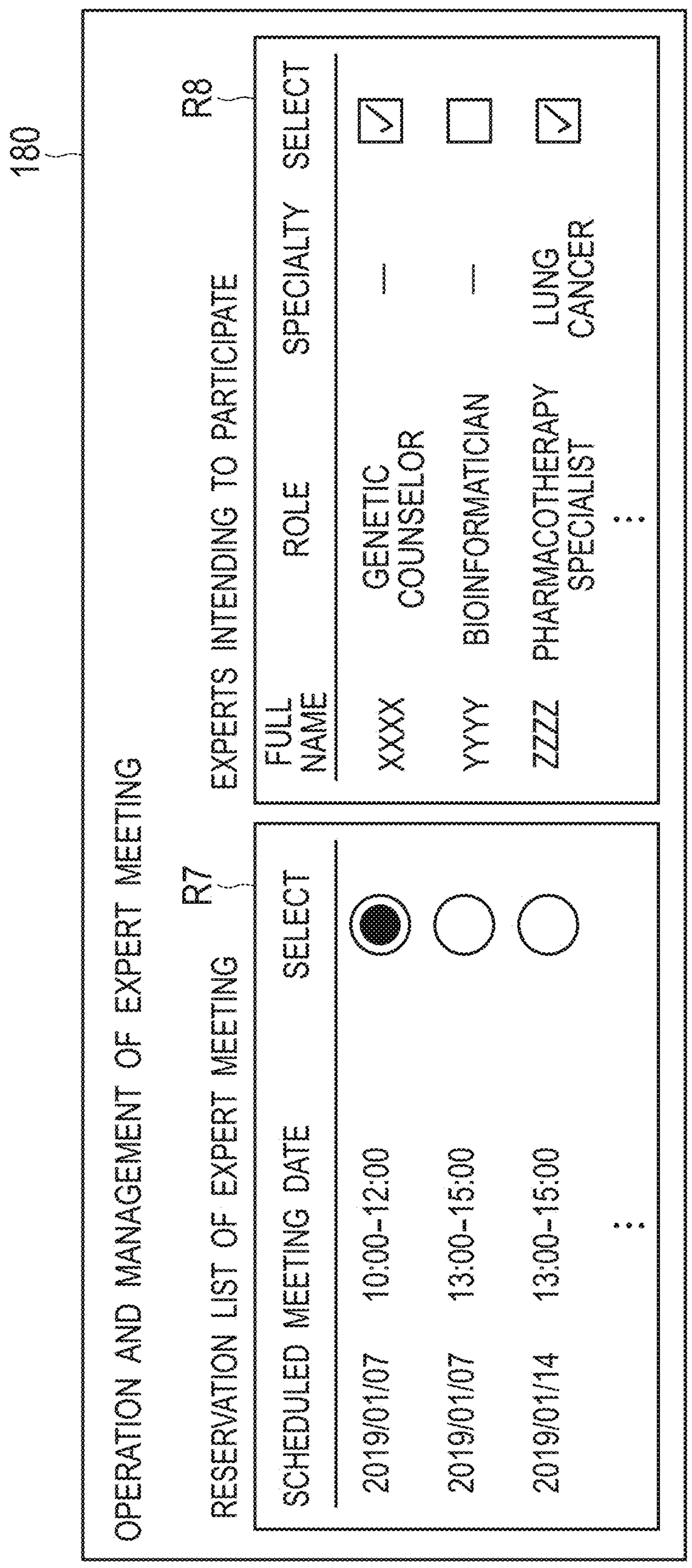
FIG. 36 is a diagram illustrating an example of a GUI displayed on a terminal device in order to receive an input of selection information on experts to attend an expert meeting.

FIG. 36 is a diagram illustrating an example of the GUI 180 displayed on the terminal devices B13, B23, C14, C24, D11, and D21 in order to accept an instruction of selecting experts to participate in an expert meeting. The GUI 180 includes a region R7 for accepting selection of the scheduled dates and time periods when expert meetings are to be held, and a region R8 for accepting an instruction to select experts to participate in the expert meetings.

The region R7 displays a list of reservations (schedule candidates) for the expert meetings scheduled to be held in the facility selected in the region R4 of the GUI 150 illustrated in FIG. 29, and is provided with selection entries each for selecting an expert meeting.

In addition, the region R8 is provided with selection entries each for selecting a full name, a role, a specialized field, and each medical specialist as a candidate expert being a medical specialist capable of participating in the expert meeting selected in the region R7. For example, the candidate expert capable of participating in the expert meeting selected may be a medical specialist who has a vacancy in the schedule of the date and time of the selected expert meeting, such as a medical specialist who is not going to participate in another expert meeting at that date and time.

In the example illustrated in FIG. 36, the expert meeting scheduled to be held at "10:00 to 12:00" on "Jan. 7, 2019" in the region R7 is selected, and in the region R8, a list of candidates of medical specialists to participate in the selected expert meeting is displayed. Moreover, the genetic counselor "XXXX" and the medical specialist "ZZZZ" specialized in lung cancer are selected as participants in the expert meeting.

For example, the controller 10 refers to the earliest date and time from the expert meeting schedule table 27 among the expert meetings scheduled to be held after a predetermined number of days (for example, 30 days) from the date indicated by the "Test Request Date" data in the master table 25 stored in the integrated database of the integrated data management device A. Note that the time period of the meeting date to be set is set every hour between, for example, 9:00 and 17:00.

The controller 10 refers to the inputted test request information to specify the patient ID corresponding to the "Test Request Date" in the master table 25 and the user ID corresponding to the test request ID and the like. The controller 10 refers to the expert meeting schedule table 27 and extracts the "Date and Time of Expert Meeting" associated with the group ID corresponding to the specified user ID.

As illustrated in FIG. 18, "Allowable Patient Count" is set beside the meeting date and time of each expert meeting in the expert meeting schedule table 27 stored in the integrated database 302 of the integrated data management device A.

For example, when accepting selection of the meeting date and time of an expert meeting as an expert meeting schedule for determining the treatment method for a predetermined patient, the controller 10 decreases by 1 (decrements) the value of the allowable patient count of the expert meeting.

When the allowable patient count of the expert meeting whose selection has been accepted is "0," the controller 10 may accept that a candidate has been selected for an expert meeting, the expert meeting being scheduled to be held after the above expert meeting and having the next earliest meeting date and time. The controller 10 notifies the medical specialists of the date and time of the accepted expert meeting.

[Cooperation with Known Applications]

The controller 10 of the integrated data management device A may have a function of cooperating with known applications installed in the terminal devices B13, B23, C14, C24, D11, D21, and the like used by medical specialists. Examples of the applications include schedule management applications such as Microsoft Outlook (registered trademark).

In this case, the controller 10 may not only display information on the meeting date and time of the expert meeting on the screens of the terminal devices B13, B23, C14, C24, D11, and D21 logged in to the integrated data management device A, but also transmit a notification for known applications installed in the terminal devices. The notification for known applications may be a notification for prompting a new setting or change of the schedule of the expert meeting. For example, the controller 10 may transmit information on the meeting date and time of the expert meeting to the schedules of accounts managed by Microsoft Outlook (registered trademark) installed in the terminal devices B13, B23, C14, C24, D11, D21, and the like of medical specialists, and register it in the schedules. Such notification is transmitted from the controller 10 of the integrated data management device A in a file format compatible with the schedule management application installed in the terminal devices B13, B23, C14, C24, D11, and D21 of the medical specialists.

Note that, even when the allowable patient count of an expert meeting whose selection has been accepted is "0" or insufficient, the controller 10 can also permit the reservation of the expert meeting to a patient who satisfies a specific condition. Here, the patient who satisfies a specific condition is a patient who needs immediate action, such as a patient who requires immediate determination of a treatment method. In this case, it is only necessary to provide an entry field that allows a medical specialist to input the presence or absence of urgency when inputting test request information.

[Setting Date of Expert Meeting Based on Expected Date and Time of Test Completion]

The controller 10 of the integrated data management device A may receive information on the expected date and time of test completion from the test information management device C11 of the test facility C1 for performing the test of the patient's genetic information such as a gene panel test, and may set the meeting date and time of an expert meeting based on the information.

For example, the meeting date and time closest to the expected date and time of test completion received from the test information management device C11 may be referred to from the expert meeting schedule table 27, and the meeting date and time of the corresponding expert meeting may be set.

In response to the update of the master table 25 from the terminal device C14 of the test facility C1, the controller 10 of the integrated data management device A may automatically set the expected test completion date. Note that the controller 10 may immediately update the master table 25 at the timing when information is received from the test information management device C11. In this case, in the integrated database of the controller 10, a default value of the number of days required for each test step is set, for example. For example, 20 days are set for the pretreatment step, 1 day for the sequence step, and 1 day for the mutation analysis step.

The controller 10 adds the number of days formed by summing the default values of the number of days required for the steps to the day indicated by the "Test Request Date" data in the master table 25, and sets the initial value of the expected test completion date. Thereafter, the controller 10 updates the expected test completion date in response to the update of the master data.

For example, the controller 10 sums the default values of the number of days required for the steps registered as completed in the "Progress Status of Test" of the master table 25. Thereafter, the controller 10 compares the date calculated by adding the sum value to the test request date with the date when the master table 25 is updated. For example, when the date of update of the master table 25 is later than the date calculated by adding the sum value to the test request date, the controller 10 adds the number of days corresponding to the difference between the two dates to the latest expected test completion date.

Specifically, when the test step is delayed more than expected, the controller 10 adds the number of days corresponding to the difference between the two dates to the latest expected test completion date. Note that, for example, when the date of update of the master table 25 is before or on the same day as the date calculated by adding the sum value to the test request date, the controller 10 does not change the expected test completion date. Specifically, the controller 10 does not change the expected test completion date when there is no delay in the test step.

Note that, when the test information management device C11 installed in the test facility C1 notifies the controller 10 of the expected test completion date, the master table 25 does not have to include the test progress information.

When the expected test completion date is updated, the controller 10 resets the date and time with vacancy for the allowable patient count which are the meeting date and time of the most recent expert meeting from the expert meeting schedule table 27 as the meeting date and time of the expert meeting. The date and time with vacancy for the allowable patient count is the date and time when the allowable patient count is not "0." The controller 10 notifies the terminal devices B13, B23, C14, C24, D11, D21, and the like used by the medical specialists of information on the date and time of the reset expert meeting. The controller 10 resets the meeting date and time of the expert meeting, and increases (increments) by 1 the allowable patient count corresponding to the meeting date and time of the expert meeting before the resetting.

<GUI 190 for Accepting Expert Meeting Settings>

The controller 10 of the integrated data management device A may cause the terminal device B13 of the medical facility B1 to display the GUI 190 for setting the meeting date and time of an expert meeting for determining the treatment method for the patient P1. For example, the controller 10 may display the GUI 150*a* illustrated in FIG. 30 on the terminal device B13 used by a specific medical specialist having the authority to set up an expert meeting.

The GUI 150*a* is provided with a "Meeting Setup" button R23. The terminal device B13 may display a GUI 190 (FIG. 37) for setting an expert meeting in response to the "Meeting Setup" button R23 being pressed by a medical specialist.

FIG. 37 is a diagram illustrating an example of the GUI 190 displayed on the terminal devices B13 and B23, the terminal devices C14 and C24, the terminal devices D11 and D21, and the like in order to accept the settings on the schedule of an expert meeting.

The GUI 190 includes a region R9 for accepting the input of patient information, a region R10 for displaying a list of medical specialists to participate in the expert meeting, a region R11 for accepting the settings on the schedule of an expert meeting, and a "Meeting Notification" button.

The region R9 is provided with an entry field for accepting the input of patient information such as the patient's full name, the patient's gender, and the patient's date of birth. The region R10 displays the full names and the like of the medical specialists to participate in the expert meeting selected in the region R11. The region R12 displays a "Meeting Notification" button for accepting an operation for notifying the medical specialists displayed in the region R10 of the meeting date and time of the selected expert meeting.

The controller 10 may give the authority to set up an expert meeting only to a predetermined medical specialist in the group (for example, main staff of the group) to participate in the expert meeting to be held at a facility for interpreting the test results on the patient. In this case, a role ID corresponding to a role in the group may be given to each medical specialist in the group.

In response to the pressing of the "Meeting Notification" button in the region R12, the controller 10 transmits the notification on the meeting date and time of an expert meeting selected from the meeting date and time of the expert meetings displayed in the region R11 to the terminal devices B13, B23, C14, C24, D11, D21, and the like of the medical specialists displayed in the region R11.

The notification is transmitted by e-mail. Alternatively, information on the meeting date and time of the expert meeting may be transmitted to the schedules of accounts managed by Microsoft Outlook (registered trademark) installed in the terminal devices B13, B23, C14, C24, D11, D21, and the like of medical specialists, and registered in the schedules.

<GUI 210 for Searching for Information on Expert Meeting>

The controller 10 of the integrated data management device A may cause the terminal devices B13, B23, C14, C24, D11, and D21 of the medical specialists to display a schedule of an expert meeting related to a patient taken care by each medical specialist and information on each expert meeting.

FIG. 38 is a diagram illustrating an example of a GUI 210 including patient IDs, test IDs, schedules of expert meetings, and information on each expert meeting in the terminal devices B13, B23, C14, C24, D11, and D21 of medical specialists.

The GUI 210 displays entry fields or sections of "Patient ID" of the patient taken care by the medical specialist who has logged in to the integrated data management device A, "Test Patient ID," "Patient's Full Name," "Gender," "Name of Facility for Expert Meeting," "Date and Time of Expert Meeting," and "Related information."

For example, the medical specialist can use the GUI 210 to confirm the patient ID, the test request ID, and the meeting date and time of the expert meeting associated with him/her. Note that the "Integrated ID" may be displayed as an alternative or addition to the "Patient ID" and "Test Request ID."

The display of the "Display Related information" in the "Related information" field is link information to information on the patient taken care by the medical specialist. For example, in response to a click on the "Display Related information" displayed in the "Related information" field of the GUI 210 by a medical specialist, the controller 10 of the integrated data management device A receives an information acquisition request from the terminal devices B13, B23, C14, C24, D11, D21, and the like. In response to receiving the information acquisition request, the controller 10 displays information on the expert meeting. The information on the expert meeting includes, for example, clinical information on the patient P1 discussed at the expert meeting, the test results, and the like. Therefore, the medical specialist who has logged in to the integrated data management device A can use the terminal device B13 to easily confirm, for example, information such as clinical information on the patient taken care by him/her and the test results.

The GUI 210 displays not only identification information on patient such as a patient ID, but also the meeting date and time of an expert meeting and the name of the facility for the expert meeting. Therefore, for example, the medical specialist who has logged in to the integrated data management device A can use the terminal device B13 to easily confirm information on where and when the expert meeting related to the patient taken care by him/her is going to be held.

Modified Example of GUI for Accepting Selection of Expert Meeting

Instead of the GUI 210 illustrated in FIG. 38, the controller 10 of the integrated data management device A may display the GUI 220 illustrated in FIG. 39 on the terminal devices B13, B23, C14, C24, D11, and D21 of medical specialists.

The GUI 220 displays information on the group to hold the expert meeting and the meeting date and time of the expert meeting on the terminal devices B13, B23, C14, C24, D11, and D21 of medical specialists.

The "Group" field of the GUI 220 displays summary information on a group including multiple medical specialists. Here, the summary information on a group may be information on the medical facility to which at least one medical specialist constituting the group belongs, or may be information on the facility for the expert meeting.

Alternatively, the summary information on a group may be information such as the facility ID associated with the "Group ID" in the group table 26. For example, in response to a click on the display of the "Group Information" field, the controller 10 may display information on the medical specialists constituting the group indicated by the "Group Information" data.

First, the GUI 220 allows a medical specialist to select information on the desired group. Subsequently, the controller 10 displays a GUI 230 including information on each expert meeting illustrated in FIG. 40.

In the GUI 230, a list of patient IDs related to the group selected in the GUI 220 is displayed. For example, when "XX Hospital Group A" is selected in the GUI 220 illustrated in FIG. 39, the controller 10 displays the GUI 230 including the patient IDs, test request IDs, patient full names, genders, and related information on the expert meeting for the patients taken care by the selected group.

Note that the group (and group ID) displayed by the controller 10 on the GUI 220 may be associated with the identification information on the facility to which at least one of the medical specialists constituting the group belongs.

<Flow of Processing of Displaying GUI 210>

Figure 41:
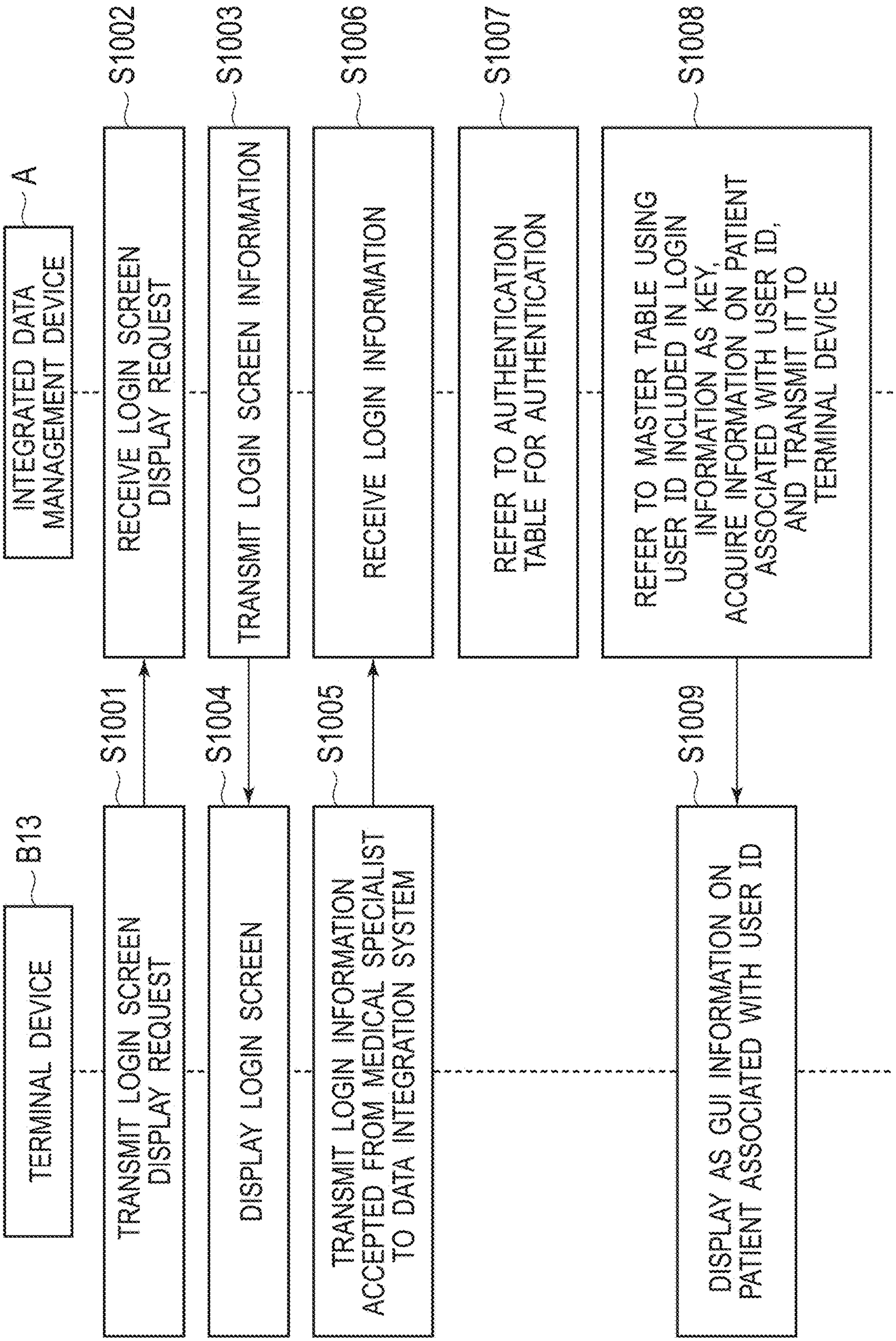
FIG. 41 is a diagram illustrating an example of a flow of the processing of causing a terminal device to display a schedule of an expert meeting related to a patient attended to by a medical specialist and information on each expert meeting.

Here, with reference to FIG. 41, description is provided for the flow of the processing of causing the terminal device B13 used by the medical specialist to display the GUI 210 (see FIG. 38) including patient information on the patient P1 and the meeting information on the expert meeting. FIG. 41 is a diagram illustrating an example of the flow of the processing of causing the terminal device B13 of a medical specialist to display a schedule of an expert meeting related to the patient P1 taken care by the medical specialist and information on each expert meeting.

First, the terminal device B13 transmits a login screen display request to the integrated data management device A (step S1001). The integrated data management device A receives a login screen display request from the terminal device B13 (step S1002), and transmits login screen information to the terminal device B13 (step S1003). The terminal device B13 receives the login screen information from the integrated data management device A, and displays the login screen (step S1004).

Next, the terminal device B13 transmits the login information accepted from the medical specialist to the integrated data management device A (step S1005). The login information includes, for example, user IDs of medical specialists.

Subsequently, the integrated data management device A receives the login information from the terminal device B13 (step S1006), and refers to the authentication table 38 stored in the integrated database 302 of the integrated data management device A to authenticate the login of the medical specialist (step S1007). Here, the authentication table 38 manages the user IDs of users who are permitted to log in to the integrated data management device A.

The integrated data management device A refers to the master table 25 using the user ID included in the login information as a key, acquires information on the patient associated with the user ID, and transmits it to the terminal device B13 (step S1008).

Next, the terminal device B13 displays as the GUI 210 the information on the patient associated with the user ID received from the integrated data management device A (step S1009).

Figure 42:
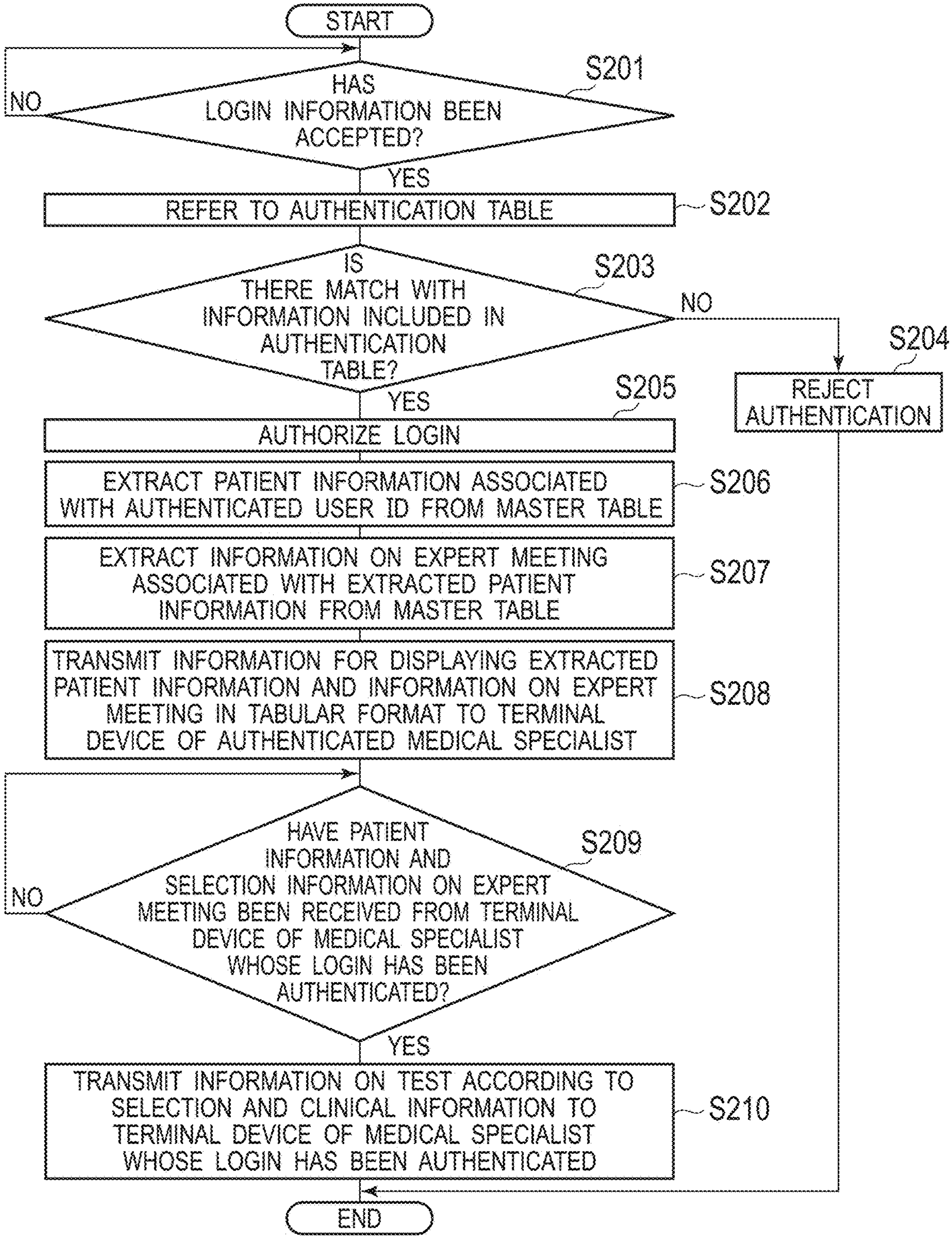
FIG. 42 is a diagram illustrating an example of a flow of the processing performed by a controller of an integrated data management device in order to display a schedule of an expert meeting related to a patient attended to by a medical specialist and information on each expert meeting on a terminal device of a medical specialist.

With reference to FIG. 42, description is provided for the details of the processing performed by the integrated data management device A in order to display the GUI 210 including the patient information on the patient P1 and the meeting information on the expert meeting on the terminal device B13 used by a medical specialist. FIG. 42 is a diagram illustrating an example of the flow of the processing performed by the controller 10 of the integrated data management device A in order to display a schedule of an expert meeting related to a patient taken care by the medical specialist and information on each expert meeting on the terminal device B13 of a medical specialist.

The controller 10 of the integrated data management device A determines whether or not login information has been accepted from the terminal device B13 (step S201). When the login information has been accepted (YES in step S201), the authentication table 38 stored in the integrated database 302 of the integrated data management device A is referred to (step S202). Subsequently, it is determined whether or not the login password corresponding to the user ID included in the authentication table 38 matches the login password included in the accepted login information (step S203). In the case of mismatch (NO in step S203), the controller 10 rejects the login authentication (step S204). On the other hand, in the case of match (YES in step S203), the login is authenticated (step S205).

Next, the controller 10 extracts the patient information associated with the user ID included in the authenticated login information from the master table 25 (step S206).

Next, the controller 10 extracts information on the expert meeting associated with the extracted patient information from the master table 25 (step S207).

Next, the controller 10 transmits files of HTML including the extracted patient information and information on the expert meeting and CSS (Cascading Style Sheets) for displaying these sets of information in a tabular format to the terminal of the authenticated user (step S208). Note that the controller 10 may transmit a JSON (JavaScript Object Notation) file including the extracted patient information and information on the expert meeting to the terminal device B13, and generate HTML and CSS using JavaScript provided in the terminal device B13.

Next, when receiving the patient information and the selection information on the expert meeting from the terminal device B13 of the medical specialist whose login has been authenticated (YES in step S209), the controller 10 transmits the information on the genetic test according to the selection and the clinical information on the patient to the terminal device B13 of the medical specialist whose login has been authenticated (step S210).

<Flow of Processing of Displaying GUI 240>

Figure 43:
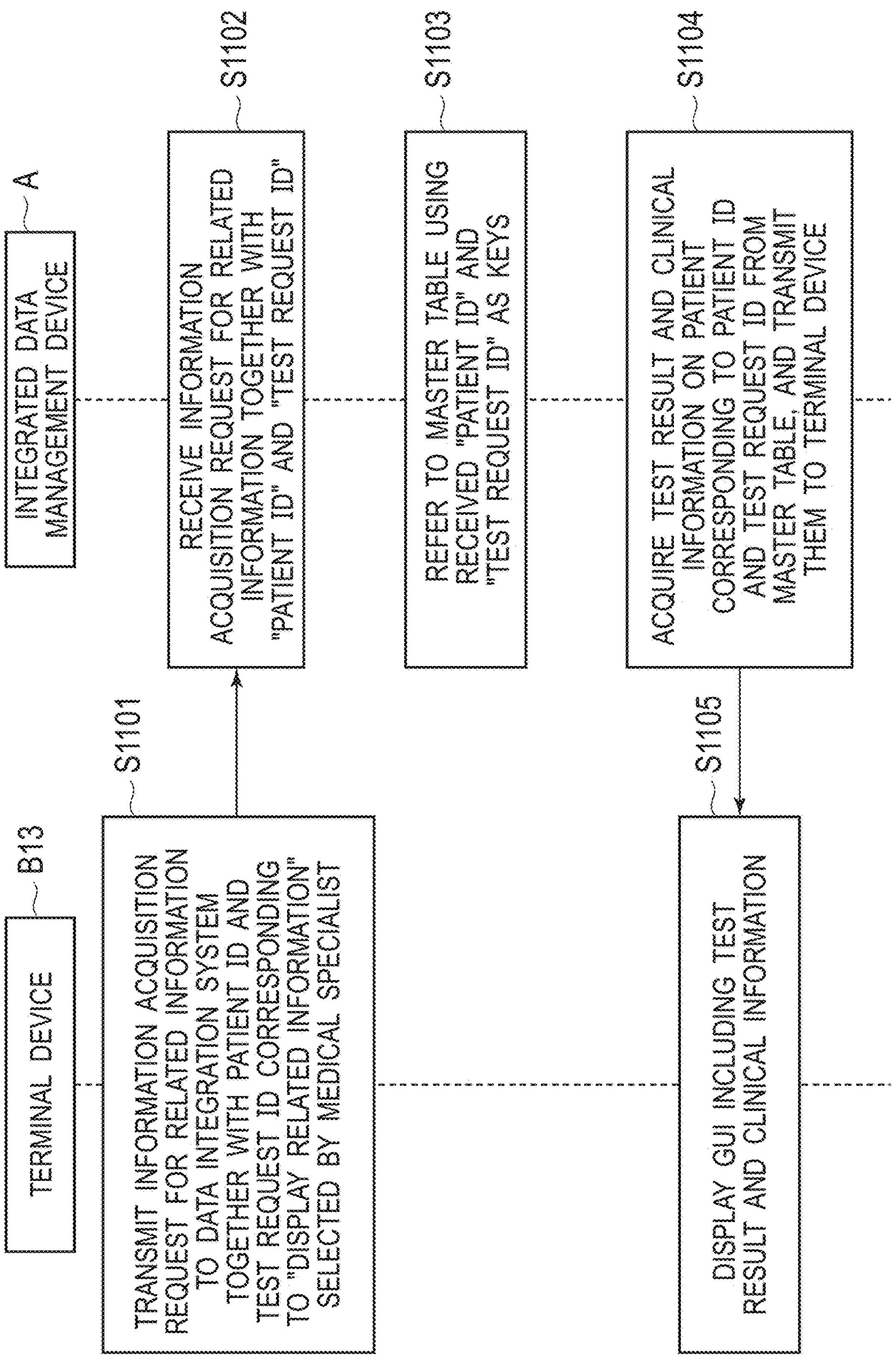
FIG. 43 is a diagram illustrating an example of a flow of the processing of displaying information on a patient attended to by a medical specialist.

Here, with reference to FIG. 43, description is provided for the flow of the processing of displaying the GUI 240 (see FIG. 45) on the terminal devices B13, B23, C14, C24, D11, D21, and the like of the medical specialists to participate in the expert meeting as a screen including test result information and clinical information on the patient P1. FIG. 43 is a diagram illustrating an example of the flow of the processing of displaying information on the patient taken care by the medical specialist.

First, the terminal device B13 installed in the medical facility B1 accepts an information acquisition request from a medical specialist via the GUI 210 illustrated in FIG. 38. The terminal device B13 transmits an information acquisition request for related information to the integrated data management device A together with the patient ID and the test request ID corresponding to the "Display Related information" having accepted a click operation by the medical specialist in the related information column of the GUI 210 (step S1101).

With reference to FIG. 43, the integrated data management device A receives an information acquisition request for related information together with the patient ID and the test request ID (step S1102). Next, the received patient ID and test request ID are used as keys to refer to the master table 25 stored in the integrated database of the integrated data management device A (step S1103). The integrated data management device A acquires the test results and the clinical information on the patient corresponding to the patient ID and the test request ID from the master table 25, and transmits them to the terminal device B13 (step S1104).

Next, the terminal device B13 of the medical facility B1 displays the patient's clinical information and test results received from the integrated data management device A as the GUI 240 (step S1105).

Figure 44:
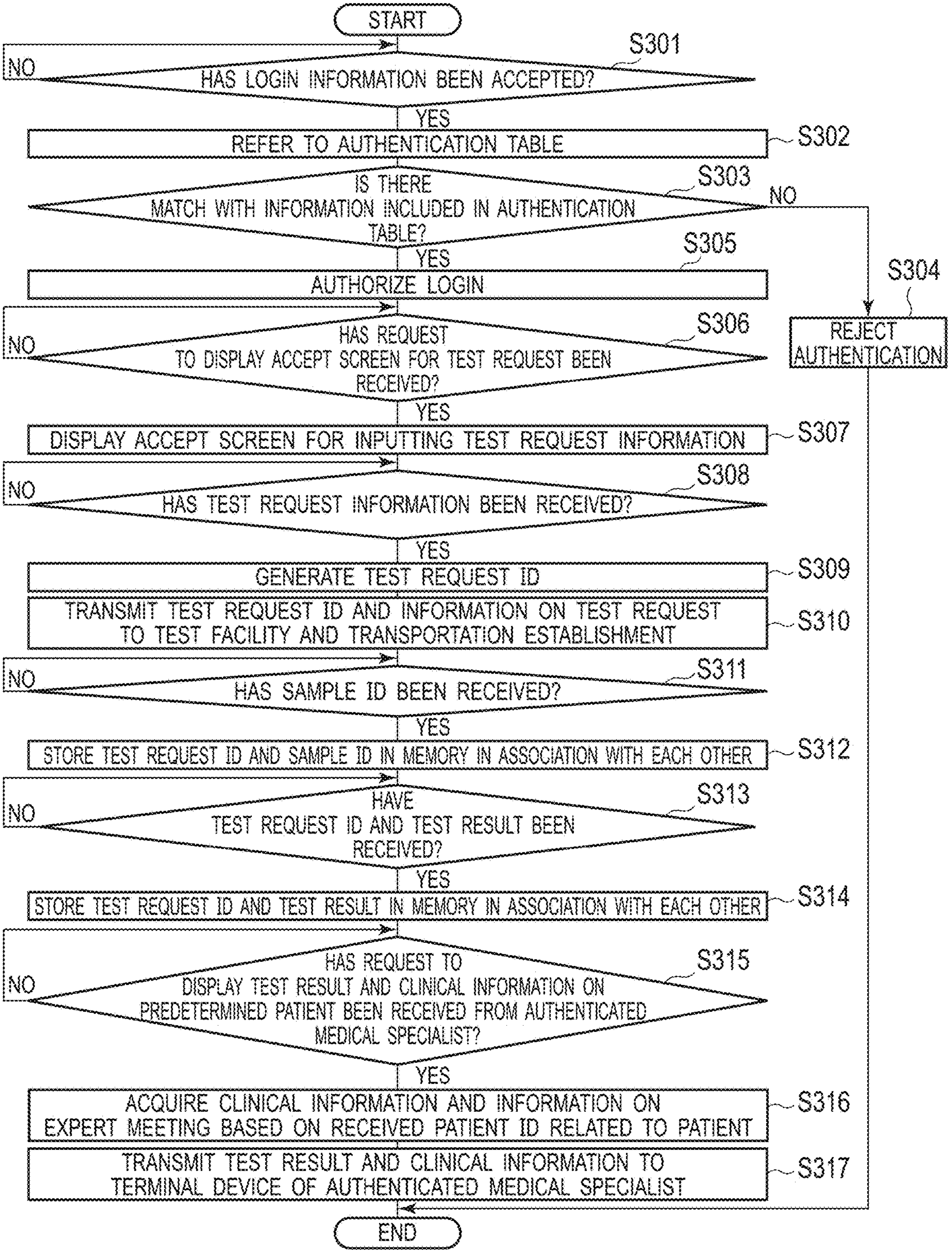
FIG. 44 is a diagram illustrating an example of a flow of the processing performed by a controller of an integrated data management device in order to display clinical information and test results of a patient, on a terminal device of a medical specialist.

With reference to FIG. 44, description is provided for the details of the processing performed by the integrated data management device A in order to display the GUI 240 including the test result information on the patient P1 and the clinical information on the patient P1 on the terminal device B13 used by a medical specialist. FIG. 44 is a diagram illustrating an example of the flow of the processing performed by the controller 10 of the integrated data management device A in order to display clinical information on the patient and the test results on the terminal device B13 of the medical specialist.

The controller 10 of the integrated data management device A determines whether or not login information has been accepted from the terminal device B13 of the medical facility B1 (step S301). When the login information has been accepted (YES in step S301), the authentication table 38 stored in the integrated database 302 of the integrated data management device A is referred to (step S302). It is determined whether or not the login password corresponding to the user ID included in the authentication table 38 matches the login password included in the accepted login information (step S303). In the case of mismatch (NO in step S303), the controller 10 rejects the login authentication (step S304). On the other hand, in the case of match (YES in step S303), the login is authenticated (step S305).

Next, the controller 10 determines whether or not a request to display the accept screen for the test request has been received from the terminal device B13 of the medical facility B1 (step S306). When the request to display the accept screen for the test request is received (YES in step S306), the accept screen for the test request is displayed on terminal device B13 (step S307).

Next, the controller 10 determines whether or not test request information has been received from the terminal device B13 of the medical facility B1 (step S308). When the test request information is received (YES in step S308), a test request ID corresponding to the test request is generated (step S309).

Next, the controller 10 associates the generated test request ID with the information on the test request, and transmits them to the terminal device C14 of the test facility C1 and the collection/delivery management device E11 of the transportation establishment E1 (step S310).

Next, the controller 10 determines whether or not the sample ID of the sample collected from the patient P1 has been received from the terminal device B13 of the medical facility B1 (step S311). When the sample ID is received (YES in step S311), the test request ID and the sample ID are associated with each other and stored in the integrated database 302 (step S312).

Next, the controller 10 determines whether or not the test request ID and the test results have been received from the terminal device C14 of the test facility C1 (step S313). When the test request ID and the test results are received (YES in step S313), the test request ID and the test results are associated with each other and stored in the integrated database 302 (step S314).

Here, the integrated database 302 associates the clinical information on the patient P1 with the test request ID, and stores them in the master table 25 of the integrated database 302 (step S21 in FIG. 12). Therefore, when the test request ID and the test results are associated with each other and stored in the integrated database 302, the clinical information on the patient P1 and the test results of the patient P1 are associated with each other via the test request ID, and stored in the master table 25 of the integrated database 302 (step S23 in FIG. 12).

With reference to FIG. 44, the controller 10 of the integrated data management device A determines whether or not a request to display the test results and clinical information on a predetermined patient P1 has been received from the authenticated medical specialist (step S315). When the request to display the test results and clinical information on a predetermined patient P1 is received (YES in step S315), the clinical information and the information on the expert meeting are acquired from the integrated database 302 of the integrated data management device A based on the received patient ID on the patient P1 (step S316).

Next, the controller 10 of the integrated data management device A transmits the test results of the patient P1 and the clinical information on the patient P1 to the terminal device B13 of the authenticated medical specialist (step S317).

<Screen Displayed in Response to Information Acquisition Request>

Next, with reference to FIG. 45, description is provided for a screen displayed by the terminal devices B13, B23, C14, C24, D11, D21, and the like used by the participants of an expert meeting in response to receiving an information acquisition request. FIG. 45 is a diagram illustrating an example of the GUI 240 displayed by the controller 10 of the integrated data management device A on the terminal devices B13, B23, C14, C24, D11, D21, and the like in response to the reception of an information acquisition request.

The GUI 240 displays "Patient ID," "Disease History of Patient," "Test Result," "Pathological Image," and "Pathologist Opinion". The disease history of patient includes, for example, information on the patient P1 such as the current disease status, family history, medical history, and treatment history of the patient P1.

In addition, as information on the test results such as "EGFR T790M," the "Test Result" displayed in the region R13 includes, for example, the presence/absence of a mutation in a base sequence, the position of the mutation, and the type of the mutation. In addition, as medicament information on the mutation detected by the gene panel test, the region R13 includes information on the therapeutic agent associated with each detected mutation, such as "Medicament A."

The region R14 displays a pathological image accepted by the integrated data management device A from the medical facility B1 related to the patient as clinical information on the patient P1. In addition, the region R15 displays a "Pathologist Opinion" button for inputting a screen transition instruction to the opinion of the pathologist H1*b* having performed a pathological diagnosis on the patient. By pressing the "Pathologist Opinion" button, it is possible to further confirm the opinion of the pathologist H1*b* based on the pathological image and the like inputted by the pathologist H1*b* as the clinical information on the patient P1.

When the multiple experts participating in the expert meeting are provided with the GUI 240 including the test results and clinical information on the patient P1 prior to the expert meeting and during the expert meeting, it is possible to collectively present information necessary for determining an optimal treatment policy for the patient P1. This makes it possible to facilitate the operation of the expert meeting, and to support discussion for determining a treatment policy for the patient.

<Association of Test Result with Information on Therapeutic Agent>

Figure 47:
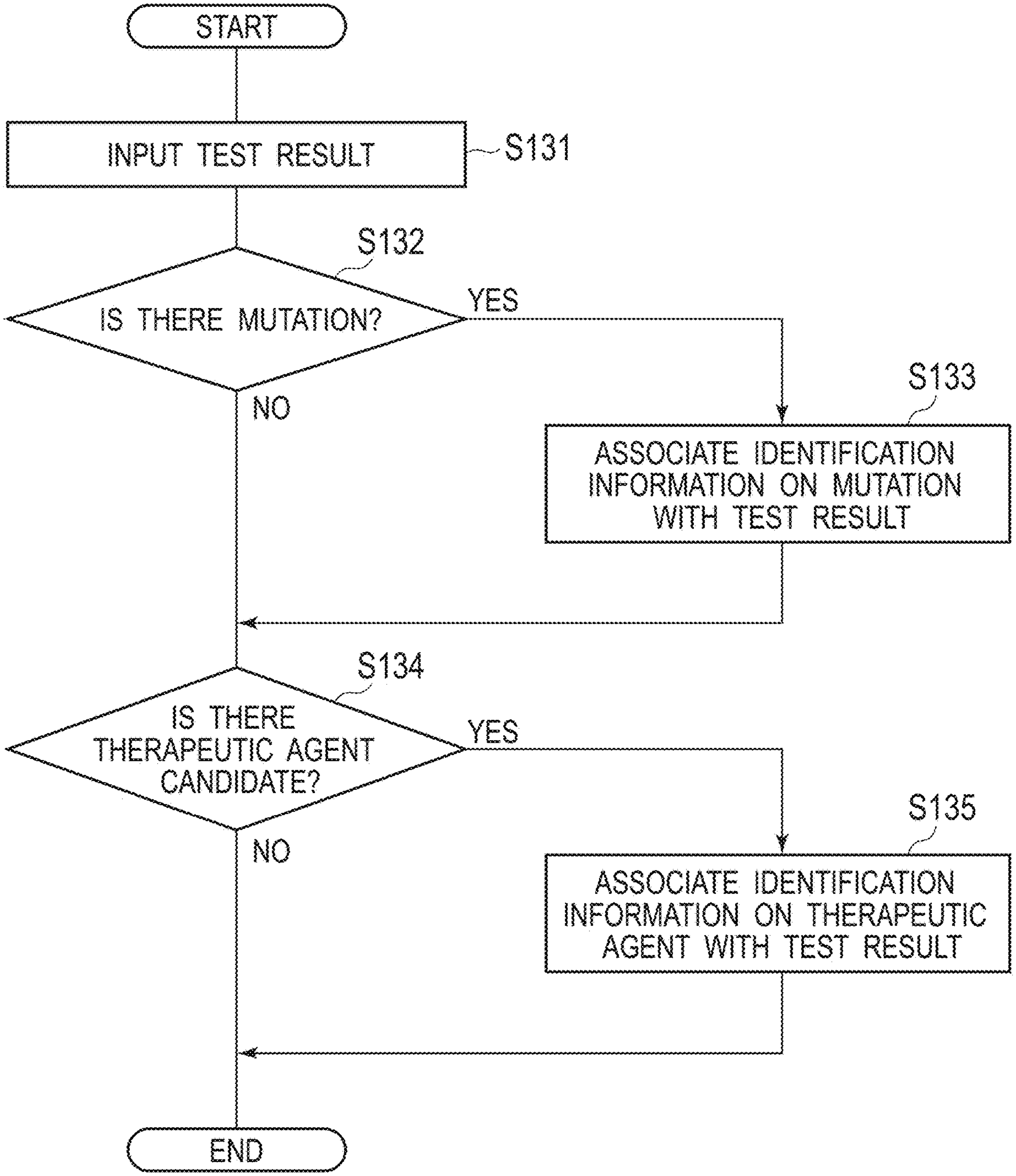
FIG. 47 is a flow diagram illustrating an example of the processing in which a controller associates information on a mutation detected by a test and information on a therapeutic agent with test results.

FIG. 47 is a flow diagram which explains an example of the processing in which the controller 10 of the integrated data management device A associates information on a mutation detected by a test and information on a therapeutic agent with the test results.

The controller 10 of the integrated data management device A accepts the input of the test results from the terminal device C14 of the test facility C1 (step S131), and determines whether or not there is a mutation detected in the detection results (step S132). When there is a mutation detected (YES in step S132), the mutation table 250 (FIG. 48) stored in the integrated database 302 is referred to, and identification information associated with each detected mutation (for example, a mutation name such as "EGFR T790M" or a mutation ID given for each mutation) is associated with the test results (step S133). After step S133, the presence or absence of a therapeutic agent candidate is checked (step S134).

When there is no mutation detected (NO in step S132), the controller 10 checks the presence or absence of a therapeutic agent candidate (step S134).

The controller 10 refers to the therapeutic agent table 260 (FIG. 49) stored in the integrated database 302, and determines whether or not there is a therapeutic agent candidate (step S134). When there is a therapeutic agent candidate (YES in step S134), identification information on the therapeutic agent candidate (for example, the name of the therapeutic agent, or medicament ID) is associated with the test results (step S135).

(Importing Annotation Information)

With reference to FIG. 2, the integrated data management device A supports acquisition of external information as annotation information serving as a reference in the expert meeting. For example, the integrated data management device A provides a link to an information search site managed by the mutation information management device F11, the medicament information management device F21, and the academic paper information management device F31.

Figure 50:
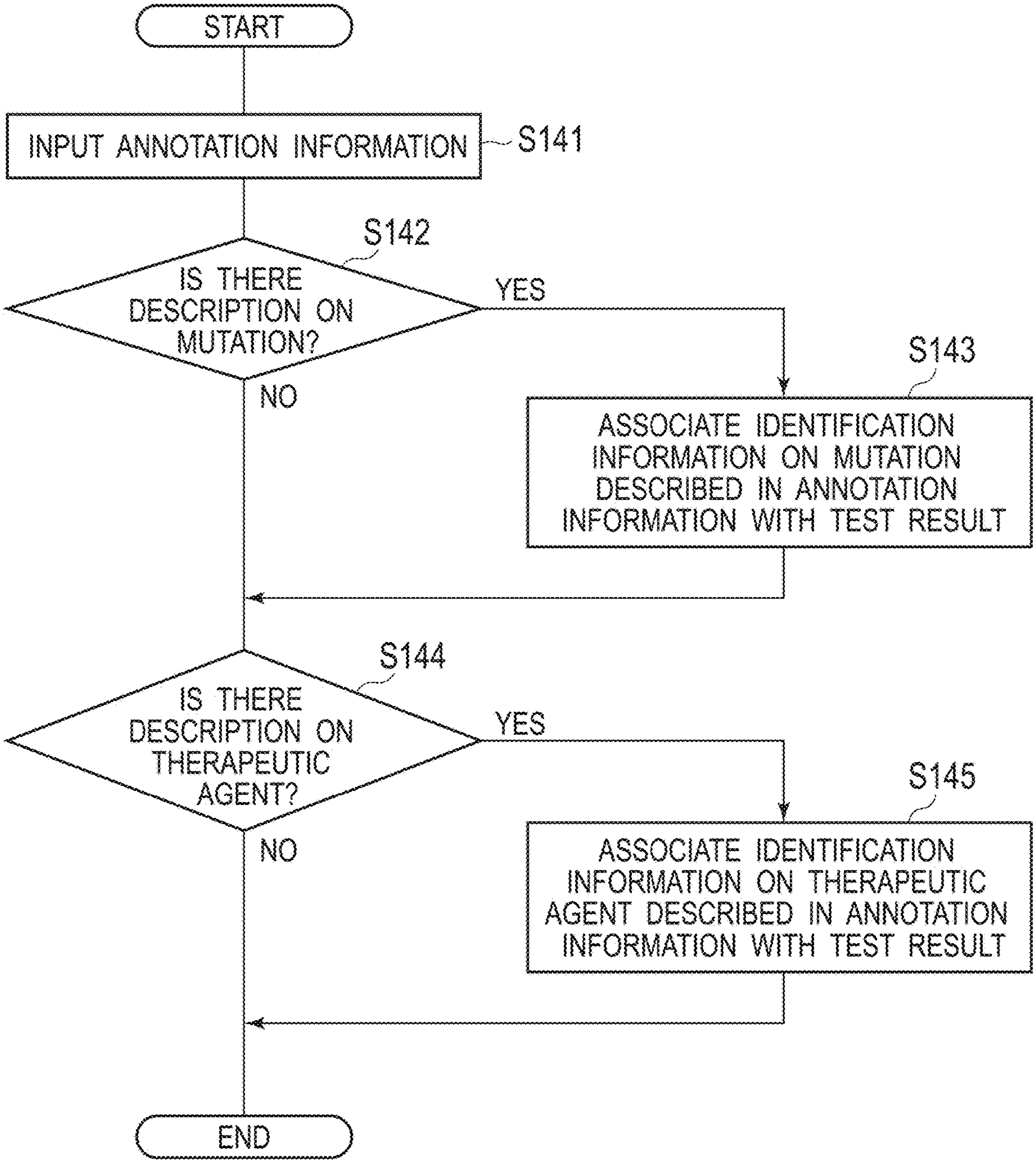
FIG. 50 is a flow diagram illustrating an example of the processing in which a controller associates inputted annotation information with test results.

FIG. 50 is a flow diagram illustrating an example of the processing in which the controller 10 of the integrated data management device A associates annotation information inputted from the mutation information management device F11, the medicament information management device F21, and the academic paper information management device F31 with the test results of the patient P1.

Figure 51:
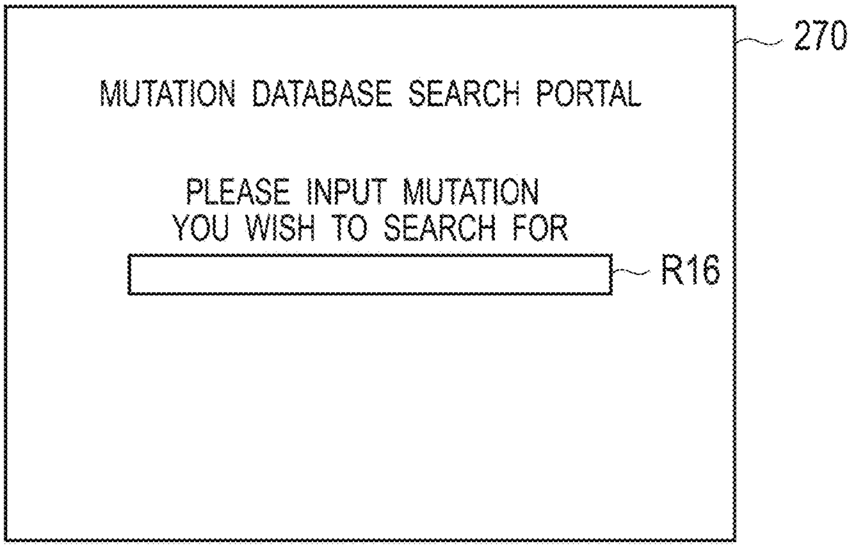
FIG. 51 is a diagram illustrating an example of a screen of a mutation database search portal.

First, the controller 10 accepts the input of annotation information from the terminal devices B13, B23, C14, C24, D11, and D21 used by the medical specialists (step S141), and determines whether or not there is a detected mutation in the test results of the patient P1 (step S142). When there is a detected mutation (YES in step S142), the identification information on the mutation described in the annotation information is associated with the mutation in the test results (step S143). After step S143, it is determined whether or not there is a description on the therapeutic agent (step S144). FIG. 51 is a diagram illustrating an example of the GUI 270 of a mutation database search portal for searching for mutation information. The GUI 270 is a search screen for searching for at least one of annotations associated with mutation information or therapeutic agent information associated with mutation, such as at least one of: annotations associated with mutation information; and therapeutic agent information associated with mutation. A region R16 is an entry field for inputting a mutation serving as a search key.

When there is no mutation detected (NO in step S142), the controller 10 determines whether or not there is a description on the therapeutic agent (step S144). When there is a description on the therapeutic agent (YES in step S144), the controller 10 associates the identification information associated with the annotation information on the therapeutic agent with the test results (step S145).

For example, the controller 10 adds the keyword used for search as meta information to the information acquired from the mutation information management device F11 and the medicament information management device F21. Examples of the keyword to be added as meta information include "EGFR T790M" and therapeutic agent names. The controller 10 performs name identification based on the added meta information. For name identification, reference is made to data related to mutations, therapeutic agents, and the like in the master table 25. The name identification method is the same as the name identification of the above-mentioned "Full Name," for example.

Figure 52:
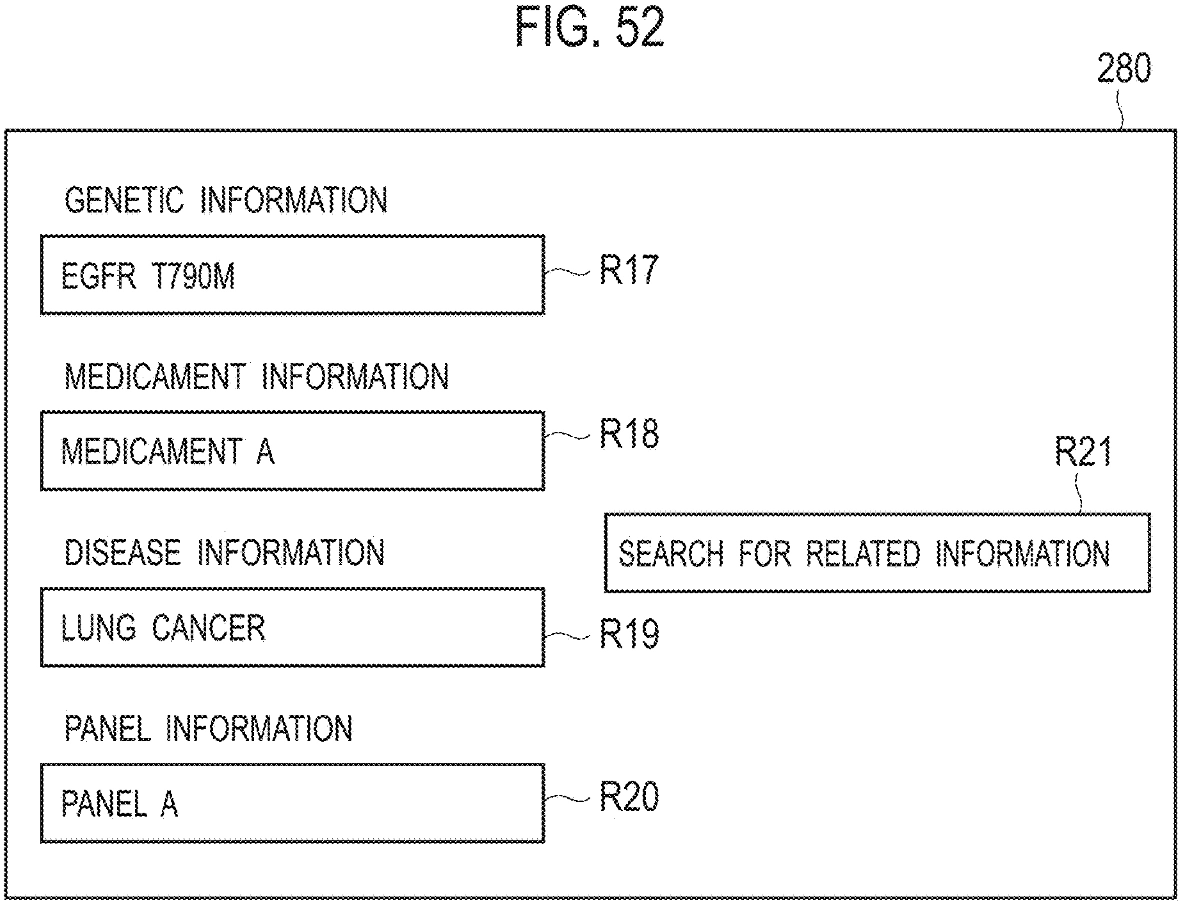
FIG. 52 is a diagram illustrating an example of a screen used to search for related information.

As described above, it is possible not only to search on the screen, but also to search for related information as a search key, such as "Genetic Information" to be inputted in the region R17, "Medicament Information" to be inputted in the region R18, "Disease Information" to be inputted in the region R19, and "Panel Information" to be inputted in the region R20 as illustrated in FIG. 52, for example.

The related information is not limited to the mutation information and medicament information managed by the mutation information management device F11 and the medicament information management device F21, and may be, for example, paper information by the academic paper information management device F31 or clinical trial information. The controller 10 executes a search in response to a click on the "Search for Related information" displayed in the region R21. Note that the "Panel Information" inputted in the region R20 corresponds to the gene panel ID, which is identification information indicating the type of the gene panel test and the reagent. It is possible to extract the test results given the gene panel ID corresponding to the information inputted as the panel information.

Modified Example 1

It has been described in the data integration processing in the integrated data management device A that an integrated ID is automatically generated every time the controller 10 of the integrated data management device A accepts the input of test request information, but the configuration may be such that the integrated ID is not automatically generated. In this case, the controller 10 may associate each dataset inputted as test request information with the data in the integrated database 302 by so-called "name identification."

Specifically, first, the controller 10 calculates an evaluation value based on an evaluation function corresponding to the matching degree between the name identification source and the name identification destination (master table 25) for each key item of the input data.

Figure 46:
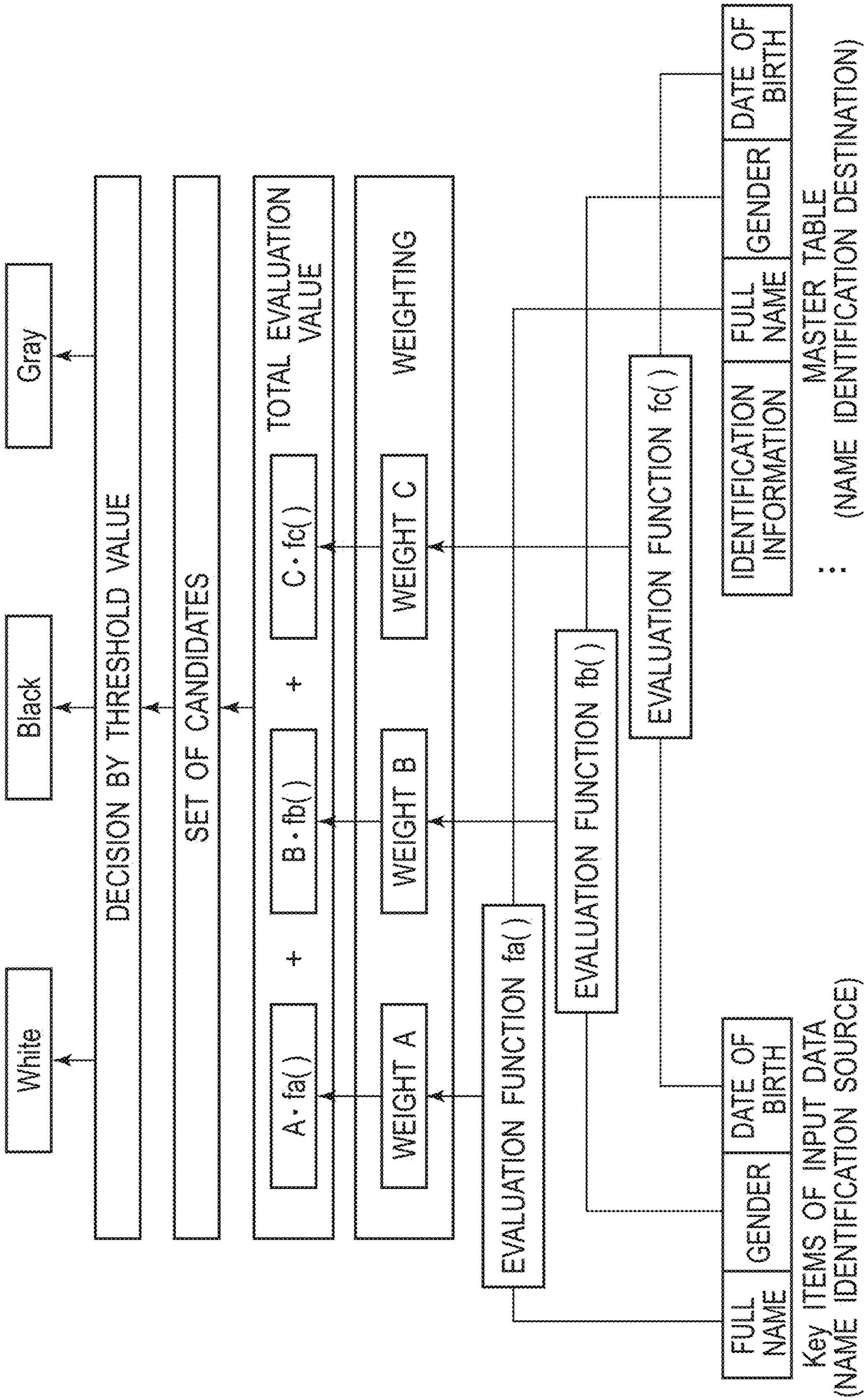
FIG. 46 is a diagram illustrating an example of a method in which a controller associates each dataset inputted as test request information with data in an integrated database.

For example, as illustrated in FIG. 46, when the input data includes key items of "Full Name," "Gender," and "Date of Birth," an edit distance (Levenshtein distance) function is used as an example of the evaluation function fa( ) of the "Name." Then, in the collation of the values of key item ("Full Name") of the name identification source and the name identification destination, an evaluation value corresponding to the minimum number of edits for transforming the character string of name identification destination into the character string of name identification source is calculated. For example, the evaluation function fa( ) returns an evaluation value "1" when editing is unnecessary, returns an evaluation value "0" when all characters need to be edited, and returns an evaluation value between 0 and 1 according to the number of edits when some of the characters need to be transformed.

In addition, as an example of the evaluation function fb( ) of the "Gender" and the evaluation function fc( ) of the "Date of Birth," a "perfect match" function is used. The perfect match function calculates an evaluation value indicating whether or not the key item values of the name identification source and the name identification destination perfectly match. For example, the perfect match function returns "1" when two values perfectly match, and returns an evaluation value "0" otherwise.

Next, the controller 10 weights each of the evaluation values calculated by the evaluation functions. In the example of FIG. 46, the evaluation value calculated by the evaluation function fa( ) is weighted by a weight A, the evaluation value calculated by the evaluation function fb( ) is weighted by a weight B, and the evaluation value calculated by the evaluation function fc( ) is weighted by a weight C.

Next, the controller 10 adds the weighted evaluation values to calculate a total evaluation value. Thereafter, the controller 10 classifies the candidates for which the total evaluation value has been calculated based on a predetermined threshold value. In the example of FIG. 46, the classification is made into three types ("White" (the total evaluation value is high), "Black" (the total evaluation value is low), and "Gray" (the total evaluation value is medium)).

The controller 10 may refer to the master table 25, and name-identify the mutation information and information on the therapeutic agent included in the test results. The name identification method is the same as the name identification related to the inputted data "Full Name" illustrated in FIG. 46, for example.

Modified Example 2

Figure 53:
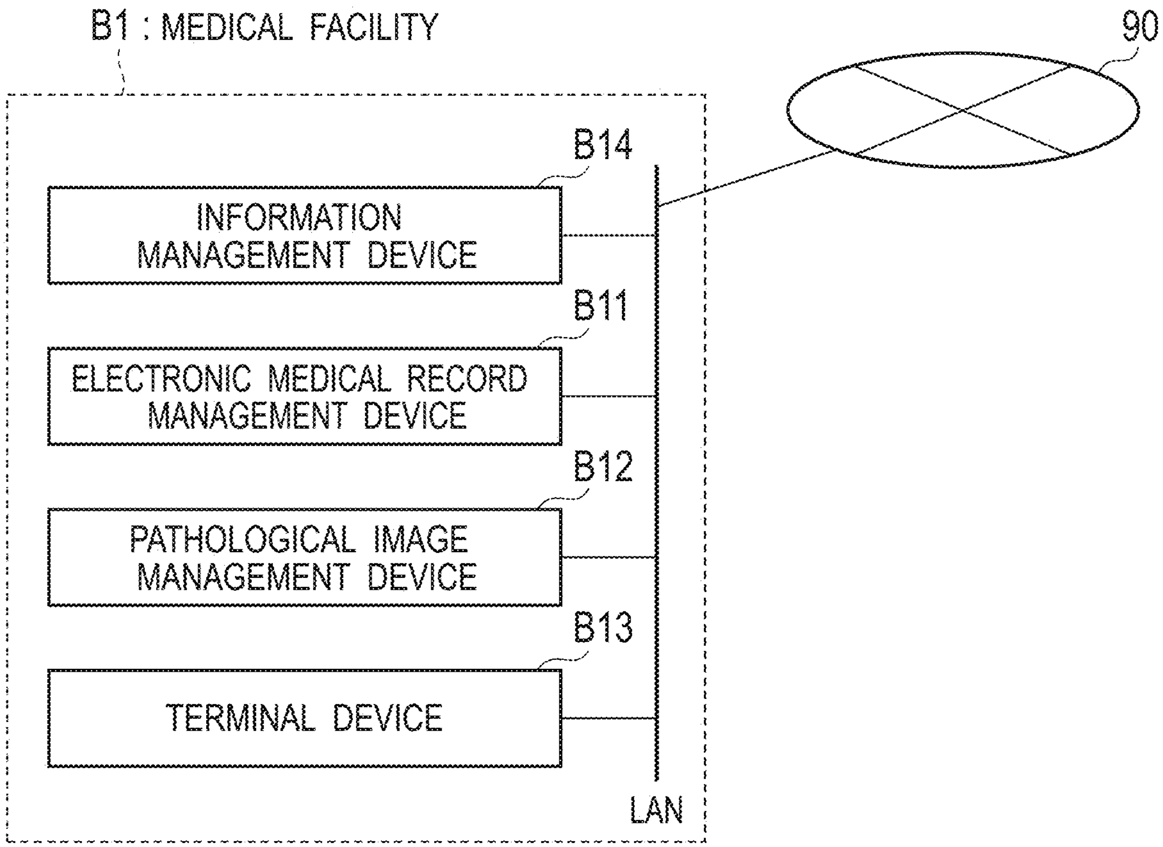
FIG. 53 is a diagram illustrating a configuration example of a medical facility that possesses an information management device.

With reference to FIG. 53, the in-medical-facility LAN may be further connected with an information management device B14 for managing data communication and various types of information on the electronic medical record management device B11, the pathological image management device B12, and the terminal device B13 in the medical facility B1. In this case, communication between the integrated data management device A and the electronic medical record management device B11, the pathological image management device B12, and the terminal device B13 installed in the medical facility B1 is performed via the information management device B14. FIG. 53 is a diagram illustrating a configuration example of the medical facility B1 including the information management device B14. The information management device B14 is a computer that executes processing of receiving various types of information arriving from the external device to the medical facility B1, and processing of transmitting various types of information transmitted from the medical facility B1 to the external device. Examples of the receiving processing include file extraction, sorting of received data, and return of a reception notification. Examples of the transmitting processing include collection, compression, and format conversion of data to be transmitted.

Modified Example 3

Figure 54:
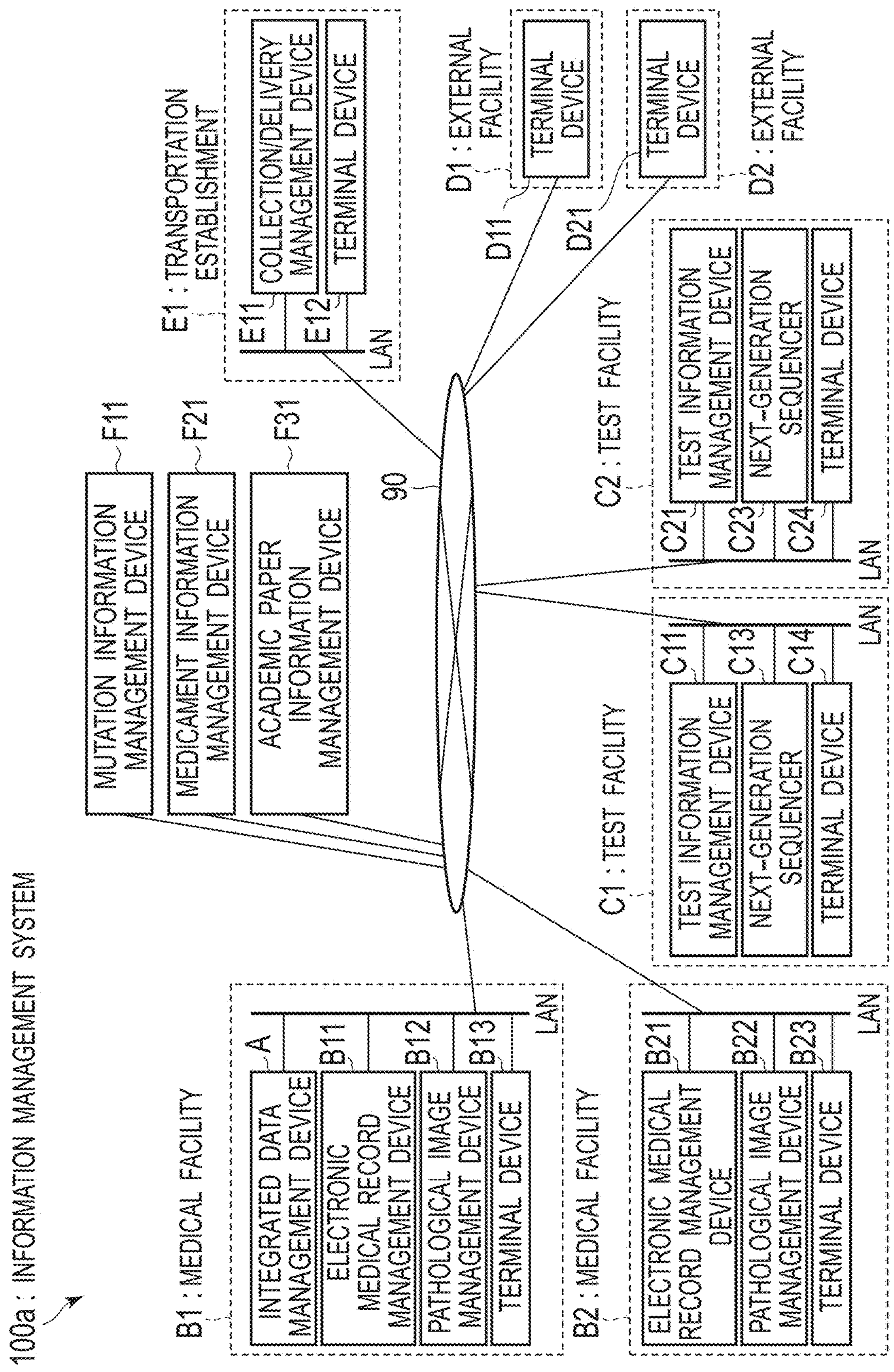
FIG. 54 is a diagram illustrating another example of a configuration of an information management system.

With reference to FIG. 54, the integrated data management device A is not necessarily a cloud server, and may be a server installed in the medical facility B1, for example. FIG. 54 is a diagram illustrating a configuration example of an information management system **100*a* according to one or more aspects. In this case, the terminal device of another medical facility B2, the terminal devices C14 and C24 of the test facilities C1 and C2, and the terminal devices D11 and D21 of the external facilities D1 and D2 communicate with the integrated data management device A installed in the medical facility B1 via the communication network 90**.

Note that, although FIG. 54 illustrates an example in which, for the integrated data management device A, the in-medical-facility LAN in the medical facility B1 is connected with the integrated data management device A, the configuration may be such that direct connection is established to the communication network 90 without going through the in-medical-facility LAN of the medical facility B1.

Modified Example 4

The integrated data management device A may be configured to have both the functions of the test information management devices C11 and C21.

[Configuration of Controller 10 of Integrated Data Management Device A]

The controller 10 of the integrated data management device A may be achieved by a logic circuit (hardware) formed in an integrated circuit (IC chip) or the like, or may be achieved by software.

In the latter case, the integrated data management device A includes a computer that executes an instruction by a program being software for achieving various functions. This computer includes, for example, one or more processors and a computer-readable storage medium storing the program.

Then, in the computer, the processor reads the program from the storage medium and executes the program, thereby achieving the object of one or more aspects. As the processor, a CPU (Central Processing Unit) can be used, for example. As the storage, it is possible to use a "non-temporary tangible medium" such as a ROM (Read Only Memory) as well as a tape, a disk, a card, a semiconductor memory, a programmable logic circuit, or the like. In addition, a RAM (Random Access Memory) for expanding the program may be further provided.

In addition, the program may be supplied to the computer via an arbitrary transmission medium capable of transmitting the program (such as a communication network or a broadcast wave). Note that one or more aspects can also be achieved in the form of a data signal embedded in a carrier wave, where the program is embodied by electronic transmission.

The present invention is not limited to the above-described embodiments, and various modifications can be made within the scope of the claims. Embodiments obtained by appropriately combining technical means disclosed in different embodiments are also included in the technical scope of the present invention.

The invention claimed is:

1. A method of supporting an expert meeting of medical specialists to interpret genetic information, comprising:

accepting a test request requesting a test for genetic information on a sample extracted from a patient;

extracting a plurality of test status information that are stored in association with the accepted test request and indicates status of the test for the test request, and schedule information on a schedule of the expert meeting to interpret the genetic information obtained in the test for the test request; and displaying the extracted plurality of test status information in a first display region and the extracted schedule information in a second display region, the first and the second display regions displayed side-by-side on one of the terminal devices of the medical specialists such that the test status information and the extracted schedule information for the patient appears on a same line, wherein the test status information comprises information on whether the test for the genetic information on the sample extracted from the patient is completed.

2. The method according to claim 1, wherein the displaying the plurality of test status information and the schedule information on the one of terminal devices of the medical specialists comprises displaying a test status screen simultaneously showing the plurality of test status information and the schedule information.

3. The method according to claim 1, further comprising:

accepting information on a preparation status of the sample for the test on the genetic information on the patient, wherein the plurality of test status information comprises the information on the preparation status of the sample.

4. The method according to claim 1, further comprising:

accepting information on a transport status of the sample for the test on the genetic information on the patient, wherein the plurality of test status information comprises the information on the transport status of the sample.

5. The method according to claim 1, further comprising:

accepting information on whether the test on the genetic information on the patient is completed.

6. The method according to claim 1, further comprising:

accepting information on a registration status of patient information on the patient, wherein the plurality of test status information comprises the information on the registration status of the patient information.

7. The method according to claim 6, further comprising:

detecting registration of the patient information; and notifying the one of terminal devices of the medical specialists of the detected patient information.

8. The method according to claim 1, further comprising:

accepting information on a setting status of the schedule of the expert meeting, wherein the schedule information comprises the information on the setting status of the schedule.

9. The method according to claim 1, further comprising:

accepting information that prompts at least one of setting, changing, or canceling of the schedule of the expert meeting, wherein the schedule information comprises the information that prompts at least one of setting, changing, or canceling of the schedule of the expert meeting.

10. The method according to claim 1, further comprising:

accepting information on a scheduled date of completing the test for the test request, wherein the plurality of test status information comprises the information on the scheduled date of completing the test.

11. The method according to claim 5, further comprising:

displaying a registration screen for registering a test result for the test request in response to an interaction with the displayed plurality of test status information, wherein the accepting the information on whether the test on the genetic information on the patient is completed comprises registering the test result by dragging and dropping a file of the test result onto the displayed registration screen.

12. An information management system that supports an expert meeting of medical specialists to interpret genetic information, comprising:

a terminal device comprising a display unit; and an integrated data management device comprising a controller and a memory, wherein the controller of the integrated data management device:

accepts a test request requesting a test for genetic information on a sample extracted from a patient;

extracts, from the memory, a plurality of test status information that are stored in association with the accepted test request and indicates status of the test for the test request, and schedule information on a schedule of the expert meeting to interpret the genetic information obtained in the test for the test request; and displays, on the display unit of the terminal device, the extracted plurality of test status information in a first display region and the extracted schedule information in a second display region, the first and the second display regions displayed side-by-side on the display unit such that the test status information and the extracted schedule information for the patient appears on a same line, and, the test status information comprises information on whether the test for the genetic information on the sample extracted from the patient is completed.

13. The information management system according to claim 12, wherein the controller of the integrated data management device displays, on the display unit of the terminal device, a test progress screen simultaneously showing the plurality of test status information and the schedule information.

14. The information management system according to claim 12, wherein the controller of the integrated data management device:

accepts information on a preparation status of the sample to be tested for the genetic information on the patient; and displays, on the display unit of the terminal device, the plurality of test status information comprising the information on the preparation status of the sample.

15. The information management system according to claim 12, wherein the controller of the integrated data management device:

accepts information on a transport status of the sample to be tested for the genetic information on the patient; and displays, on the display unit of the terminal device, the plurality of test status information comprising the information on the transport status of the sample.

16. The information management system according to claim 12, wherein the controller of the integrated data management device:

accepts the information on whether the test on the genetic information on the patient is completed.

17. The information management system according to claim 12, wherein the controller of the integrated data management device:

accepts information on a registration status of patient information on the patient; and displays, on the display unit of the terminal device, the plurality of test status information comprising the information on the registration status of the patient information.

18. The information management system according to claim 17, wherein the controller of the integrated data management device:

detects registration of the patient information; and notifies the terminal device of the detected patient information.

19. The information management system according to claim 12, wherein the controller of the integrated data management device:

accepts information on a setting status of the schedule of the expert meeting; and displays, on the display unit of the terminal device, the schedule information comprising the information on the setting status of the schedule.

20. The information management system according to claim 12, wherein the controller of the integrated data management device:

accepts information that prompts at least one of setting, changing, or canceling of the schedule of the expert meeting; and displays, on the display unit of the terminal device, the schedule information comprising the information that prompts at least one of setting, changing, or canceling of the schedule of the expert meeting.

21. The information management system according to claim 12, wherein the controller of the integrated data management device:

accepts information on a scheduled date of completing the test for the test request; and displays, on the display unit of the terminal device, the plurality of test status information comprising the information on the scheduled date of completing the test.

22. An integrated data management device that supports an expert meeting of medical specialists to interpret genetic information, comprising:

a controller; and a memory, wherein the controller:

accepts a test request requesting a test for genetic information on a sample extracted from a patient;

extracts, from the memory, a plurality of test status information that are stored in association with the accepted test request and indicates status of the test for the test request, and schedule information on a schedule of the expert meeting to interpret the genetic information obtained in the test for the test request; and transmits information to display the extracted plurality of test status information in a first display region and the extracted schedule information in a second display region, the first and the second display regions displayed side-by-side on one of terminal devices of the medical specialists such that the test status information and the extracted schedule information for the patient appears on a same line, and the test status information comprises information on whether the test for the genetic information on the sample extracted from the patient is completed.

23. The method according to claim 1, further comprising:

accepting information on a registration status of a result of the test, wherein the plurality of test status information comprises the information on the registration status of the result of the test.

* * * * *